US012643940B2

(12) United States Patent   (10) Patent No.: US 12,643,940 B2
Klein et al.   (45) Date of Patent: Jun. 2, 2026

(54) BROADLY NEUTRALIZING ANTIBODIES AGAINST HIV

(71) Applicant: Universität zu Köln, Cologne (DE)

(72) Inventors: Florian Klein, Cologne (DE); Henning Grüll, Cologne (DE); Philipp Frederik Schommers, Cologne (DE)

(73) Assignee: Universität zu Köln, Cologne (DE)

( * ) Notice: Subject to any disclaimer, the term of this patent is extended or adjusted under 35 U.S.C. 154(b) by 949 days.

(21) Appl. No.: 17/782,027

(22) PCT Filed: Dec. 2, 2020

(86) PCT No.: PCT/EP2020/084309
§ 371 (c)(1),
(2) Date: Dec. 15, 2022

(87) PCT Pub. No.: WO2021/110764
PCT Pub. Date: Jun. 10, 2021

(65) Prior Publication Data
US 2024/0376183 A1     Nov. 14, 2024

(30) Foreign Application Priority Data

Dec. 2, 2019   (EP) .................................... 19212986

(51) Int. Cl.
C07K 16/114     (2026.01)
A61K 39/00     (2006.01)
A61P 31/18     (2006.01)

(52) U.S. Cl.
CPC .......... C07K 16/1145 (2026.01); A61P 31/18 (2018.01); A61K 2039/505 (2013.01); C07K 2317/21 (2013.01); C07K 2317/76 (2013.01)

(58) Field of Classification Search
None
See application file for complete search history.

(56) References Cited

U.S. PATENT DOCUMENTS

| | | | |
|---|---|---|---|
| 9,695,230 | B2 | 7/2017 | Kwong et al. |
| 2015/0044137 | A1 | 2/2015 | Mascola et al. |
| 2015/0158934 | A1 | 6/2015 | McCoy et al. |
| 2018/0079801 | A1 | 3/2018 | Haynes et al. |

FOREIGN PATENT DOCUMENTS

| | | |
|---|---|---|
| JP | 2014-516527 A | 7/2014 |
| JP | 2015-534982 A | 12/2015 |
| WO | WO-2012/154312 A1 | 11/2012 |
| WO | WO-2012/158948 A1 | 11/2012 |
| WO | WO-2013/036130 A1 | 3/2013 |
| WO | WO-2013/142324 A1 | 9/2013 |
| WO | WO-2014/063059 A1 | 4/2014 |
| WO | WO-2016/149695 A1 | 9/2016 |
| WO | WO-2019/165122 A1 | 8/2019 |

OTHER PUBLICATIONS

Holt, 2003, TRENDS biotech. vol. 21: 484-490.*
Rabia et al. 2018, Biochem. Eng. J. vol. 137: 365-374.*
Hall, 1992, J. Immunol. vol. 149: 1605-1612 Dondelinger, Front. Immunol. vol. 9: 1-15.*
Burgers, 2005. Best. Pract. Res. Clin. Obst. Gyn. vol. 19: 277-291 Su et al., 2017, Scientific Reports pp. 1-7.*
Altschul, S.F. et al., Basic local alignment search tool, J. Mol. Biol., 215(3):403-10 (1990).
Altschul, S.F. et al., Gapped BLAST and PSI-BLAST: a new generation of protein database search programs, Nucleic Acids Res, 25(17):3389-402 (1997).
Anderson, J.P. et al., Testing the hypothesis of a recombinant origin of human immunodeficiency virus type 1 subtype E, J Virol., 74(22):10752-65 (2000).
Bonsignori, M. et al., Maturation Pathway from Germline to Broad HIV-1 Neutralizer of a CD4-Mimic Antibody, Cell, 165(2):449-63 (2016).
Dashti, A. et al., Broadly Neutralizing Antibodies against HIV: Back to Blood, Trends Mol Med., 25(3):228-240 (2019).
Decamp, A. et al., Global panel of HIV-1 Env reference strains for standardized assessments of vaccine-elicited neutralizing antibodies, J Virol., 88(5):2489-507 (2014).
Doria-Rose, N.A. et al., Mapping Polyclonal HIV-1 Antibody Responses via Next-Generation Neutralization Fingerprinting, PLoS Pathog., 13(1):e1006148 (2017).
Dosenovic, P. et al., Anti-idiotypic antibodies elicit anti-HIV-1-specific B cell responses, J Exp Med., 216(10):2316-2330 (2019).
Ehrhardt, S.A. et al., Polyclonal and convergent antibody response to Ebola virus vaccine rVSV-ZEBOV, Nat Med., 25(10):1589-1600 (2019).
Freund, N.T. et al., Coexistence of potent HIV-1 broadly neutralizing antibodies and antibody-sensitive viruses in a viremic controller, Sci Transl Med., 9(373):eaal2144 (2017).
Freund, N.T., et al., A New Glycan-Dependent CD4-Binding Site Neutralizing Antibody Exerts Pressure on HIV-1 In Vivo, PLoS Pathog., 11(10):e1005238 (2015).
Gaebler, C. et al., Combination of quadruplex qPCR and next-generation sequencing for qualitative and quantitative analysis of the HIV-1 latent reservoir, J Exp Med., 216(10):2253-2264 (2019).
Gruell, H. and Klein, F., Antibody-mediated prevention and treatment of HIV-1 infection, Retrovirology, 15(1):73 (2018).

(Continued)

*Primary Examiner* — Amy E Juedes

(74) *Attorney, Agent, or Firm* — Choate, Hall & Stewart LLP; Stephanie L. Schonewald; Dana M. Daukss

(57)   ABSTRACT

The present disclosure relates to monoclonal human antibodies or binding fragments thereof which are directed against the CD4 binding site of the human immunodeficiency virus HIV-1, a pharmaceutical composition comprising such monoclonal human antibodies or binding fragments thereof, a kit comprising such antibodies or binding fragments thereof, and the monoclonal antibodies or binding fragments thereof and the pharmaceutical composition and the kit for use as a medicament, and in the treatment or prevention of a disease caused by the human immunodeficiency virus HIV-1.

7 Claims, 16 Drawing Sheets

Specification includes a Sequence Listing.

(56) References Cited

OTHER PUBLICATIONS

Horwitz, J.A. et al., HIV-1 suppression and durable control by combining single broadly neutralizing antibodies and antiretroviral drugs in humanized mice, Proc Natl Acad Sci USA, 110(41):16538-43 (2013).

Horwitz, J.A. et al., Non-neutralizing Antibodies Alter the Course of HIV-1 Infection In Vivo, Cell, 170(4):637-648.e10 (2017).

Hraber, P. et al., Panels of HIV-1 Subtype C Env Reference Strains for Standardized Neutralization Assessments, J Virol., 91(19):e00991-17 (2017).

International Search Report for PCT/EP2020/084309, 6 pages (Feb. 11, 2021).

Karlin, S. and Altschul, S., et al., Applications and statistics for multiple high-scoring segments in molecular sequences, Proc Natl Acad Sci USA, 90(12):5873-7 (1993).

Klein, F. et al., HIV therapy by a combination of broadly neutralizing antibodies in humanized mice, Nature, 492(7427):118-22 (2012).

Kreer, C. et al., openPrimeR for multiplex amplification of highly diverse templates, J Immunol Methods, 480:112752 (2020).

Kryazhimskiy, S. et al., Microbial evolution. Global epistasis makes adaptation predictable despite sequence-level stochasticity, Science, 344(6191):1519-1522 (2014).

Lefranc, M.P. et al., IMGT, the international ImMunoGeneTics database, Nucleic Acids Res., 27(1):209-12 (1999).

Mendoza, P. et al., Combination therapy with anti-HIV-1 antibodies maintains viral suppression, Nature, 561(7724):479-484 (2018).

Pietzsch, J. et al., Human anti-HIV-neutralizing antibodies frequently target a conserved epitope essential for viral fitness, J Exp Med., 207(9):1995-2002 (2010).

Qiao, Y. et al., Isolation and characterization of a novel neutralizing antibody targeting the CD4-binding site of HIV-1 gp120, Antiviral Res., 132:252-61 (2016).

Sanders, R.W. et al., A next-generation cleaved, soluble HIV-1 Env trimer, BG505 SOSIP.664 gp140, expresses multiple epitopes for broadly neutralizing but not non-neutralizing antibodies, PLoS Pathog., 9(9):e1003618 (2013).

Sarzotti-Kelsoe, M. et al., Optimization and validation of the TZM-bl assay for standardized assessments of neutralizing antibodies against HIV-1, J Immunol Methods, 409:131-46 (2014).

Scheid, J.F. et al., HIV-1 antibody 3BNC117 suppresses viral rebound in humans during treatment interruption, Nature, 535(7613):556-60 (2016).

Schoofs, T. et al., Broad and Potent Neutralizing Antibodies Recognize the Silent Face of the HIV Envelope, Immunity, 50(6):1513-1529.e9 (2019).

Schoofs, T. et al., HIV-1 therapy with monoclonal antibody 3BNC117 elicits host immune responses against HIV-1, Science, 352(6288):997-1001 (2016).

Seaman, M.S. et al., Tiered categorization of a diverse panel of HIV-1 Env pseudoviruses for assessment of neutralizing antibodies, J Virol., 84(3):1439-52 (2010).

Sliepen, K. et al., Engineering and Characterization of a Fluorescent Native-Like HIV-1 Envelope Glycoprotein Trimer, Biomolecules, 5(4):2919-34 (2015).

Sok, D. and Burton, D.R., Recent progress in broadly neutralizing antibodies to HIV, Nat Immunol., 19(11):1179-1188 (2018).

Tiller, T. et al., Efficient generation of monoclonal antibodies from single human B cells by single cell RT-PCR and expression vector cloning, J Immunol Methods, 329(1-2):112-24 (2008).

Written Opinion for PCT/EP2020/084309, 7 pages (Feb. 11, 2021).

Wu, X. et al., Rational design of envelope identifies broadly neutralizing human monoclonal antibodies to HIV-1, Science, 329(5993):856-61 (2010).

Yang, X. et al., Characterization of stable, soluble trimers containing complete ectodomains of human immunodeficiency virus type 1 envelope glycoproteins, J Virol., 74(12):5716-25 (2000).

Ye, J. et al., IgBLAST: an immunoglobulin variable domain sequence analysis tool, Nucleic Acids Res., 41(Web Server issue):W34-40 (2013).

Yoon, H. et al., CATNAP: a tool to compile, analyze and tally neutralizing antibody panels, Nucleic Acids Res., 43(W1):W213-9 (2015).

Zhang, Y.J. et al., Envelope-dependent, cyclophilin-independent effects of glycosaminoglycans on human immunodeficiency virus type 1 attachment and infection, J Virol., 76(12):6332-43 (2002).

* cited by examiner

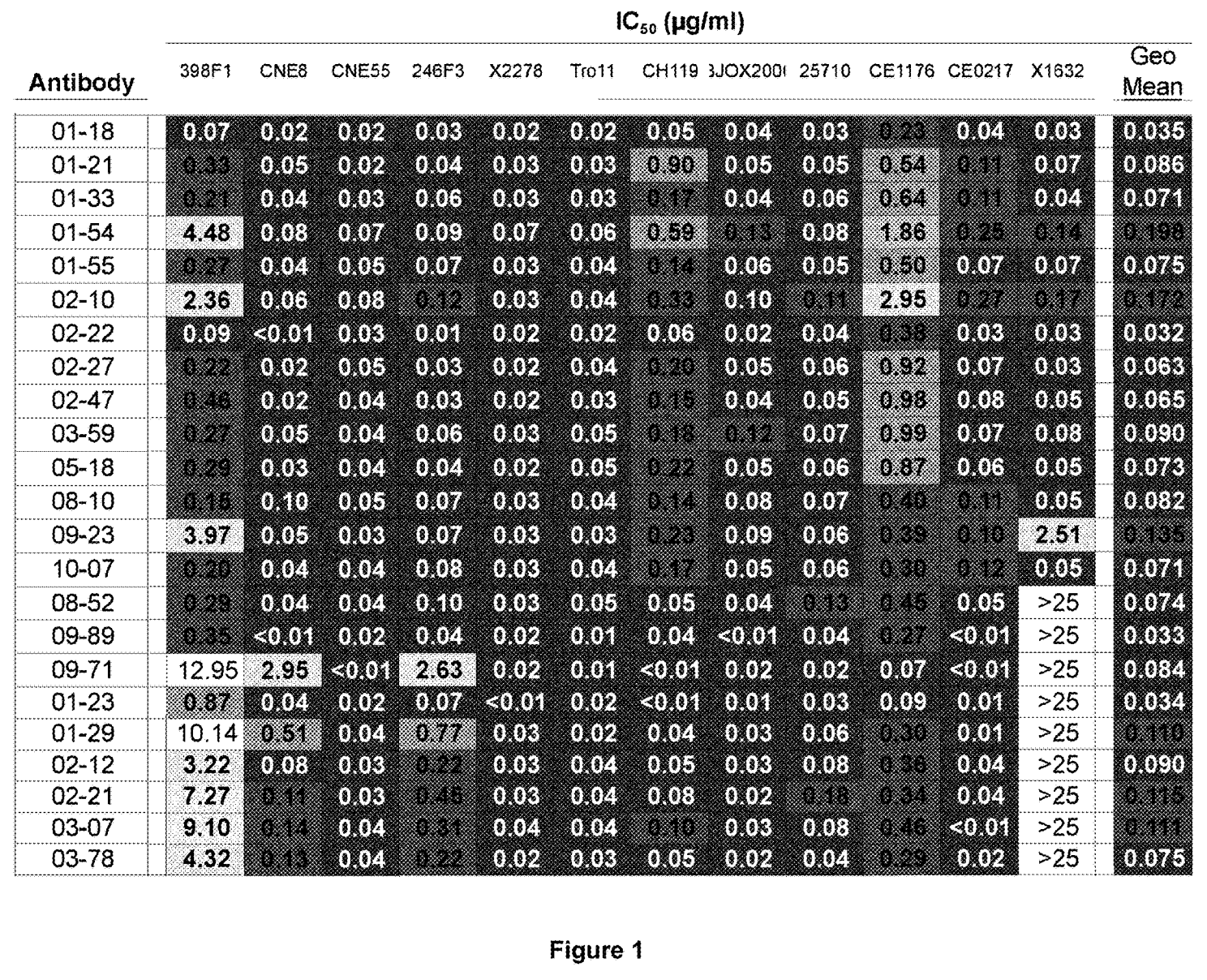

IC$_{50}$ (µg/ml)

| Antibody | 398F1 | CNE8 | CNE55 | 246F3 | X2278 | Tro11 | CH119 | 3JOX200i | 25710 | CE1176 | CE0217 | X1632 | Geo Mean |
|---|---|---|---|---|---|---|---|---|---|---|---|---|---|
| 01-18 | 0.07 | 0.02 | 0.02 | 0.03 | 0.02 | 0.02 | 0.05 | 0.04 | 0.03 | 0.23 | 0.04 | 0.03 | 0.035 |
| 01-21 | 0.33 | 0.05 | 0.02 | 0.04 | 0.03 | 0.03 | 0.90 | 0.05 | 0.05 | 0.54 | 0.11 | 0.07 | 0.086 |
| 01-33 | 0.21 | 0.04 | 0.03 | 0.06 | 0.03 | 0.03 | 0.17 | 0.04 | 0.06 | 0.64 | 0.11 | 0.04 | 0.071 |
| 01-54 | 4.48 | 0.08 | 0.07 | 0.09 | 0.07 | 0.06 | 0.39 | 0.13 | 0.08 | 1.86 | 0.25 | 0.14 | 0.198 |
| 01-55 | 0.27 | 0.04 | 0.05 | 0.07 | 0.05 | 0.04 | 0.14 | 0.06 | 0.05 | 0.50 | 0.07 | 0.07 | 0.075 |
| 02-10 | 2.36 | 0.06 | 0.08 | 0.12 | 0.03 | 0.04 | 0.33 | 0.10 | 0.11 | 2.95 | 0.27 | 0.17 | 0.172 |
| 02-22 | 0.09 | <0.01 | 0.03 | 0.01 | 0.02 | 0.02 | 0.06 | 0.02 | 0.04 | 0.38 | 0.03 | 0.03 | 0.032 |
| 02-27 | 0.22 | 0.02 | 0.05 | 0.03 | 0.02 | 0.04 | 0.10 | 0.05 | 0.06 | 0.92 | 0.07 | 0.03 | 0.063 |
| 02-47 | 0.46 | 0.02 | 0.04 | 0.03 | 0.02 | 0.03 | 0.15 | 0.04 | 0.05 | 0.98 | 0.08 | 0.05 | 0.065 |
| 03-59 | 0.27 | 0.05 | 0.04 | 0.06 | 0.03 | 0.05 | 0.18 | 0.12 | 0.07 | 0.99 | 0.07 | 0.08 | 0.090 |
| 05-18 | 0.29 | 0.03 | 0.05 | 0.04 | 0.03 | 0.05 | 0.22 | 0.05 | 0.06 | 0.87 | 0.06 | 0.05 | 0.073 |
| 08-10 | 0.15 | 0.10 | 0.02 | 0.07 | 0.03 | 0.04 | 0.25 | 0.08 | 0.07 | 0.46 | 0.11 | 0.05 | 0.082 |
| 09-23 | 3.97 | 0.05 | 0.04 | 0.07 | 0.02 | 0.03 | 0.17 | 0.09 | 0.06 | 0.39 | 0.10 | 2.51 | 0.105 |
| 10-07 | 0.20 | 0.04 | 0.04 | 0.08 | 0.03 | 0.04 | 0.17 | 0.05 | 0.06 | 0.46 | 0.12 | 0.05 | 0.071 |
| 08-52 | 0.29 | 0.04 | <0.01 | 2.63 | 0.02 | 0.05 | 0.05 | 0.04 | 0.04 | 0.45 | 0.05 | 0.05 | 0.074 |
| 09-89 | 0.35 | <0.01 | 0.02 | 0.07 | <0.01 | 0.01 | 0.04 | 0.02 | 0.02 | 0.27 | <0.01 | >25 | 0.033 |
| 09-71 | 12.95 | 2.95 | 0.02 | 0.07 | 0.02 | 0.02 | <0.01 | 0.01 | 0.03 | 0.07 | 0.01 | >25 | 0.084 |
| 01-23 | 0.87 | 0.04 | 0.04 | 0.77 | <0.01 | 0.02 | <0.01 | 0.01 | 0.06 | 0.09 | 0.01 | >25 | 0.034 |
| 01-29 | 10.14 | 0.51 | 0.03 | 0.22 | 0.03 | 0.04 | 0.04 | 0.03 | 0.08 | 0.30 | 0.04 | >25 | 0.110 |
| 02-12 | 3.22 | 0.08 | 0.03 | 0.45 | 0.03 | 0.04 | 0.05 | 0.02 | 0.10 | 0.34 | 0.04 | >25 | 0.090 |
| 02-21 | 7.27 | 0.14 | 0.03 | 0.22 | 0.04 | 0.04 | 0.08 | 0.02 | 0.08 | 0.46 | 0.04 | >25 | 0.115 |
| 03-07 | 9.10 | 0.14 | 0.04 | 0.22 | 0.04 | 0.04 | 0.10 | 0.03 | 0.08 | 0.46 | <0.01 | >25 | 0.111 |
| 03-78 | 4.32 | 0.19 | 0.04 | 0.22 | 0.02 | 0.03 | 0.05 | 0.02 | 0.04 | 0.29 | 0.02 | >25 | 0.075 |

Figure 1

| Virus | Clade | 1-18 IC$_{50}$ | 1-55 IC$_{50}$ | 2-12 IC$_{50}$ | N6 IC$_{50}$ | 3BNC117 IC$_{50}$ | VRC01 IC$_{50}$ | 10-1074 IC$_{50}$ | PGT121 IC$_{50}$ |
|---|---|---|---|---|---|---|---|---|---|
| MS208.A1 | A | 0.031 | 0.046 | 0.048 | 0.060 | 0.020 | 0.114 | >20 | >20 |
| Q23.17 | A | 0.017 | 0.019 | 0.026 | 0.060 | 0.016 | 0.084 | 0.004 | 0.003 |
| Q461.e2 | A | 0.053 | 0.079 | 0.069 | 0.199 | 0.064 | 0.443 | >20 | >20 |
| Q769.d22 | A | 0.020 | 0.021 | 0.009 | 0.031 | 0.009 | 0.026 | >20 | >20 |
| Q259.d2.17 | A | 0.018 | 0.030 | 0.016 | 1.011 | 0.017 | 0.074 | 3.054 | 7.516 |
| Q842.d12 | A | 0.006 | 0.008 | 0.006 | 0.015 | 0.003 | 0.019 | 12.812 | 0.012 |
| 3415.v1.c1 | A | 0.076 | 0.014 | 0.089 | 0.040 | 0.110 | 0.087 | >20 | >20 |
| 0260.v5.c36 | A | 0.010 | 0.156 | 0.030 | 0.191 | 0.192 | 0.617 | 0.157 | 0.059 |
| 3365.v2.c2 | A | 0.025 | 0.116 | 0.015 | 0.060 | 0.014 | 0.048 | 0.021 | 0.142 |
| 191955_A11 | A | 0.017 | 0.025 | 0.021 | 0.030 | >20 | 0.980 | >20 | >20 |
| 191084 B7-19 | A | 0.023 | 0.056 | 0.018 | 0.031 | 0.066 | 0.168 | 0.032 | 0.021 |
| 9004SS_A3_4 | A | 0.031 | 0.059 | 0.036 | 0.116 | 0.064 | 0.505 | 0.009 | 0.004 |
| 6535.3 | B | 0.068 | 0.178 | 0.055 | 0.171 | 0.339 | 1.560 | 0.008 | 0.003 |
| QH0692.42 | B | 0.089 | 0.067 | 0.211 | 0.449 | 0.236 | 1.465 | 0.148 | 0.540 |
| SC422661.8 | B | 0.009 | 0.015 | 0.020 | 0.067 | 0.046 | 0.111 | 0.062 | 0.072 |
| PVO.4 | B | 0.017 | 0.034 | 0.013 | 0.067 | 0.068 | 0.417 | 0.070 | 0.114 |
| TRO.11 | B | 0.015 | 0.027 | 0.012 | 0.161 | 0.047 | 0.313 | 0.013 | 0.007 |
| AC10.0.29 | B | 0.369 | 0.420 | 0.296 | 0.267 | 6.457 | 1.462 | 0.022 | 0.026 |
| RHPA4259.7 | B | 0.015 | 0.020 | 0.006 | 0.020 | 0.023 | 0.049 | 0.018 | 0.013 |
| THRO4156.18 | B | 1.584 | 0.928 | 0.481 | 0.565 | 2.634 | 3.714 | >20 | >20 |
| REJO4541.67 | B | 0.016 | 0.020 | 0.011 | 0.030 | 0.028 | 0.059 | >20 | 3.843 |
| TRJO4551.58 | B | 0.060 | 0.084 | 0.018 | 0.111 | 0.068 | 0.084 | 0.152 | 2.732 |
| WITO4160.33 | B | 0.006 | 0.020 | 0.005 | 0.079 | 0.023 | 0.127 | 0.179 | 0.519 |
| CAAN5342.A2 | B | 0.804 | 1.314 | 0.496 | 0.208 | 0.633 | 1.077 | 0.005 | 0.007 |
| WEAU_d15_410_5017 | B | 0.010 | 0.054 | 0.004 | 0.018 | 0.052 | 0.114 | 0.044 | 0.031 |
| 1006_11_C3_1601 | B | 0.039 | 0.059 | 0.005 | 0.076 | 0.035 | 0.181 | 0.002 | 0.003 |
| 1054_07_TC4_1499 | B | 0.475 | 0.408 | 0.456 | 0.312 | 0.088 | 0.889 | 0.082 | 0.066 |
| 1056_10_TA11_1826 | B | 0.033 | 0.051 | 0.017 | 0.137 | 0.267 | 1.006 | 0.048 | 0.014 |
| 1012_11_TC21_3257 | B | 0.008 | 0.023 | 0.013 | 0.038 | 0.022 | 0.111 | 0.011 | 0.005 |
| 6240_08_TA5_4622 | B | 0.312 | 0.315 | 0.165 | 0.195 | 0.254 | 0.769 | 0.047 | 0.055 |
| 6244_13_B5_4576 | B | 0.023 | 0.049 | 0.028 | 0.074 | 0.036 | 0.269 | 0.129 | 0.105 |
| 62357_14_D3_4589 | B | 0.060 | 0.041 | 0.019 | 0.057 | 0.053 | 1.066 | >20 | 2.571 |
| SC05_8C11_2344 | B | 0.045 | 0.066 | 0.086 | 0.215 | 0.134 | 0.593 | 0.025 | 0.030 |

Figure 3

| Virus | Clade | 1-18 IC50 | 1-55 IC50 | 2-12 IC50 | N6 IC50 | 3BNC117 IC50 | VRC01 IC50 | 10-1074 IC50 | PGT121 IC50 |
|---|---|---|---|---|---|---|---|---|---|
| Du156.12 | C | 0.022 | 0.081 | 0.106 | 0.014 | 0.031 | 0.088 | 0.012 | 0.005 |
| Du172.17 | C | >20 | >20 | 2.555 | 0.077 | 0.354 | >20 | 0.040 | 0.048 |
| Du422.1 | C | 0.063 | 0.144 | 0.050 | 0.027 | >20 | >20 | 0.045 | 0.040 |
| ZM197M.PB7 | C | 0.091 | 0.214 | 0.137 | 0.124 | 0.350 | 0.520 | >20 | >20 |
| ZM214M.PL15 | C | 0.048 | 0.098 | 0.007 | 0.125 | 0.089 | 0.767 | 0.434 | 0.443 |
| ZM233M.PB6 | C | 0.042 | 11.256 | 0.438 | 0.084 | 0.201 | 2.732 | 0.025 | 2.121 |
| ZM249M.PL1 | C | 0.020 | 0.060 | 5.632 | 0.031 | 0.040 | 0.070 | >20 | >20 |
| ZM53M.PB12 | C | 0.256 | 0.387 | 0.123 | 0.319 | 0.222 | 0.880 | >20 | 0.001 |
| ZM109F.PB4 | C | 9.916 | >20 | >20 | 0.108 | 0.075 | 0.124 | >20 | 9.124 |
| ZM135M.PL10a | C | 1.729 | >20 | >20 | 0.255 | 0.060 | 0.811 | 0.070 | 0.870 |
| CAP45.2.00.G3 | C | >20 | >20 | >20 | 0.043 | 1.350 | 5.630 | >20 | 1.317 |
| CAP210.2.00.E8 | C | 0.818 | 1.044 | >20 | >20 | 9.797 | >20 | >20 | 15.205 |
| HIV-001428-2.42 | C | 0.007 | 0.011 | 0.008 | 0.007 | 0.015 | 0.019 | 0.028 | 0.018 |
| HIV-0013095-2.11 | C | 0.151 | >20 | >20 | 0.078 | 0.258 | 0.128 | 5.840 | >20 |
| HIV-16055-2.3 | C | 0.019 | 0.018 | 0.018 | 0.021 | 4.176 | 0.099 | >20 | 0.456 |
| HIV-16845-2.22 | C | 0.862 | 1.876 | 1.039 | 0.697 | >20 | 3.606 | 0.793 | 5.855 |
| Ce1086_B2 | C | 0.092 | 0.062 | 0.051 | 0.058 | 0.071 | 0.571 | >20 | 0.001 |
| Ce0393_C3 | C | 0.036 | 0.056 | >20 | 0.100 | 0.202 | 1.039 | >20 | >20 |
| Ce1176_A3 | C | 0.199 | 0.544 | 0.156 | 0.427 | 0.194 | 2.315 | 0.021 | 0.014 |
| Ce2010_F5 | C | 0.139 | 0.197 | 0.057 | 0.166 | 0.054 | 0.638 | >20 | >20 |
| Ce0682_E4 | C | 0.015 | 0.016 | 0.019 | 0.042 | 0.032 | 0.175 | >20 | >20 |
| Ce1172_H1 | C | 0.295 | 0.173 | >20 | 0.515 | >20 | >20 | 0.022 | 0.013 |
| Ce2060_G9 | C | 0.086 | 0.440 | 0.091 | 0.163 | 0.214 | 0.444 | >20 | >20 |
| Ce703010054_2A2 | C | 0.032 | 0.061 | 0.037 | 0.163 | 0.313 | 0.750 | >20 | >20 |
| BF1266.431a | C | 0.030 | 0.104 | >20 | 0.022 | 0.027 | 0.073 | >20 | >20 |
| 246F C1G | C | 0.006 | 0.051 | >20 | 0.101 | 15.899 | 7.000 | 0.033 | 0.055 |
| 249M B10 | C | 0.027 | 0.064 | 19.962 | 0.033 | 0.084 | 0.130 | >20 | 3.200 |
| ZM247v1(Rev-) | C | 0.023 | 0.035 | >20 | 0.053 | >20 | 0.326 | 0.046 | 0.029 |
| 7030102001E5(Rev-) | C | 0.121 | 0.203 | 0.091 | 0.244 | 0.315 | 1.065 | 0.008 | 0.008 |
| 1394C9G1(Rev-) | C | 0.287 | 6.291 | 0.941 | 0.079 | >20 | 0.574 | 0.033 | 0.400 |
| Ce704809221_1B3 | C | 0.078 | 0.114 | 0.148 | 0.445 | 0.074 | 0.878 | 0.096 | 0.039 |
| 3016.v5.c45 | D | 1.227 | 11.424 | 0.024 | 0.020 | 0.804 | 0.153 | >20 | >20 |
| A07412M1.vrc12 | D | 0.043 | 0.128 | 0.042 | 0.050 | 0.029 | 0.152 | 0.004 | 0.008 |
| 231965.c01 | D | 0.115 | >20 | 1.641 | 0.048 | 0.042 | 0.357 | 10.000 | >20 |
| 231966.c02 | D | 0.096 | 0.312 | 0.024 | 0.059 | 0.218 | 0.119 | >20 | >20 |
| 6405.v4.c34 | D | >20 | >20 | 14.354 | 0.072 | 0.171 | 2.399 | 0.007 | 0.018 |

Figure 3 *(continued)*

| Virus | Clade | 1-18 IC$_{50}$ | 1-55 IC$_{50}$ | 2-12 IC$_{50}$ | N6 IC$_{50}$ | 3BNC117 IC$_{50}$ | VRC01 IC$_{50}$ | 10-1074 IC$_{50}$ | PGT121 IC$_{50}$ |
|---|---|---|---|---|---|---|---|---|---|
| X1193_c1 | G | 0.050 | 0.025 | 0.360 | 0.061 | 0.065 | 0.138 | 0.072 | 0.022 |
| P0402_c2_11 | G | 0.043 | 0.010 | 0.035 | 0.032 | 0.061 | 0.222 | 0.008 | 0.006 |
| X1254_c3 | G | 0.027 | 0.142 | 0.203 | 0.031 | 0.078 | 0.057 | 0.075 | 0.019 |
| X2088_c9 | G | 0.089 | 0.165 | 0.137 | 0.081 | >20 | >20 | 0.002 | 0.003 |
| X2131_C1_B5 | G | 0.053 | 0.365 | 0.192 | 0.183 | 0.357 | 0.464 | 0.017 | 0.007 |
| P1981_C5_3 | G | 11.131 | >20 | 10.492 | 0.131 | 0.483 | 0.403 | 0.002 | 0.001 |
| X1632_S2_B10 | G | 0.017 | 0.020 | >20 | 0.068 | 4.981 | 0.109 | >20 | >20 |
| 3301.v1.c24 | AC | 0.005 | 0.022 | 0.010 | 0.012 | 0.032 | 0.126 | 0.010 | 0.009 |
| 6041.v3.c23 | AC | 0.004 | 0.013 | 0.003 | 0.014 | 0.009 | 0.023 | >20 | >20 |
| 6540.v4.c1 | AC | 0.005 | 0.015 | 0.014 | 0.064 | >20 | >20 | >20 | >20 |
| 6545.v4.c1 | AC | 0.004 | 0.013 | 4.100 | 16.228 | >20 | >20 | >20 | >20 |
| 620345.c01 | AE | 0.145 | 0.222 | >20 | 4.393 | >20 | >20 | >20 | >20 |
| CNE8 | AE | 0.005 | 0.026 | 0.022 | 0.112 | 0.086 | 0.678 | >20 | >20 |
| C1080.c03 | AE | 0.020 | 0.069 | 0.010 | 0.383 | 0.120 | 1.613 | >20 | >20 |
| R2184.c04 | AE | 0.004 | 0.011 | 0.005 | 0.021 | 0.032 | 0.081 | >20 | >20 |
| R1166.c01 | AE | 0.006 | 0.015 | 0.006 | 0.200 | 0.203 | 1.642 | >20 | >20 |
| R3265.c06 | AE | 0.010 | 0.030 | 0.005 | 0.040 | 0.060 | 0.347 | >20 | >20 |
| C2101.c01 | AE | 0.038 | 0.077 | 0.003 | 0.073 | 0.060 | 0.189 | >20 | >20 |
| C3347.c11 | AE | 0.027 | 0.018 | 0.016 | 0.012 | 0.031 | 0.077 | >20 | >20 |
| C4118.c09 | AE | 0.040 | 0.161 | 0.020 | 0.089 | 0.030 | 0.111 | >20 | >20 |
| CNE5 | AE | 0.184 | 2.789 | 0.137 | 0.139 | 0.344 | 0.332 | >20 | >20 |
| BJOX009000.02.4 | AE | 0.386 | 19.308 | 0.124 | 0.353 | 0.365 | 2.412 | >20 | 4.156 |
| BJOX015000.11.5 | AE | 0.117 | 0.097 | 0.033 | 0.067 | 0.053 | 0.293 | >20 | >20 |
| BJOX010000.06.2 | AE | 0.526 | 3.403 | 0.228 | 0.587 | 1.772 | 9.188 | >20 | >20 |
| BJOX025000.01.1 | AE | 0.120 | 0.054 | 0.024 | 0.020 | 0.063 | 4.126 | >20 | >20 |
| BJOX028000.10.3 | AE | 0.806 | >20 | 0.027 | 0.003 | 0.012 | 0.532 | >20 | >20 |
| T257-31 | AG | 0.050 | 0.105 | 0.183 | 0.171 | 0.133 | 2.145 | >20 | >20 |
| 928-28 | AG | 0.189 | 0.633 | 0.133 | 0.097 | 0.156 | 0.436 | 0.759 | >20 |
| 263-8 | AG | 0.016 | 0.038 | 0.019 | 0.047 | 0.030 | 0.200 | 0.262 | 1.008 |
| T250-4 | AG | 0.019 | 0.037 | >20 | 0.016 | >20 | >20 | 0.001 | 0.001 |
| T251-18 | AG | 0.044 | 0.070 | 0.044 | 0.365 | 0.210 | 3.419 | 0.387 | 10.177 |
| T278-50 | AG | >20 | 10.349 | >20 | >20 | >20 | >20 | 0.942 | >20 |
| T255-34 | AG | 0.042 | 0.793 | >20 | 0.147 | 0.042 | 0.435 | 0.380 | 9.198 |
| 211-9 | AG | 0.076 | 0.422 | >20 | 0.358 | 0.346 | 16.437 | 0.108 | 0.997 |
| 235-47 | AG | 0.007 | 0.015 | 0.027 | 0.020 | 0.025 | 0.044 | 0.019 | 0.184 |

Figure 3 (continued)

| Virus | Clade | 1-18 IC$_{50}$ | 1-55 IC$_{50}$ | 2-12 IC$_{50}$ | N6 IC$_{50}$ | 3BNC117 IC$_{50}$ | VRC01 IC$_{50}$ | 10-1074 IC$_{50}$ | PGT121 IC$_{50}$ |
|---|---|---|---|---|---|---|---|---|---|
| CNE19 | BC | 0.006 | 0.011 | 0.006 | 0.055 | 0.023 | 0.245 | 0.199 | 0.008 |
| CNE20 | BC | 0.033 | 0.060 | 0.007 | 0.025 | >20 | 8.270 | 0.001 | 0.001 |
| CNE21 | BC | 0.039 | 0.056 | 0.017 | 0.067 | 19.054 | 0.441 | 0.043 | 0.008 |
| CNE17 | BC | 0.157 | 15.490 | 0.086 | 0.328 | 4.893 | 1.541 | 1.791 | 9.777 |
| CNE30 | BC | 0.076 | 0.150 | 0.075 | 0.291 | 0.336 | 0.825 | 0.299 | 0.077 |
| CNE52 | BC | 0.007 | 0.011 | 0.003 | 0.052 | 0.027 | 0.215 | 1.887 | 2.843 |
| CNE53 | BC | 0.089 | 0.215 | 0.032 | 0.109 | 0.066 | 0.104 | 0.008 | 0.013 |
| CNE58 | BC | 0.017 | 0.027 | 0.009 | 0.040 | 0.360 | 0.164 | 0.139 | >20 |
| 3817.v2.c59 | CD | 0.131 | 0.725 | 2.284 | 0.562 | 0.197 | >20 | 0.734 | 18.892 |
| 6480.v4.c25 | CD | 0.023 | 0.013 | 0.025 | 0.038 | 0.010 | 0.040 | 0.006 | 0.003 |
| 6952.v1.c20 | CD | 0.035 | 0.309 | 0.020 | 0.022 | 0.120 | 0.050 | 0.016 | 0.060 |
| 6811.v7.c18 | CD | 0.042 | 0.066 | 0.074 | 0.069 | 0.038 | 0.168 | 0.002 | 0.002 |
| 89-F1_2_25 | CD | 0.007 | 0.014 | 0.006 | >20 | >20 | >20 | >20 | >20 |
| 0815.v3.c3 | ACD | 0.009 | 0.011 | 0.003 | 0.017 | 0.015 | 0.040 | 0.022 | 0.020 |
| 3103.v3.c10 | ACD | 0.050 | 0.146 | 18.167 | 0.331 | 0.270 | 1.193 | 0.020 | 0.017 |
| GeoMean of Neutralized | | 0.048 | 0.096 | 0.053 | 0.086 | 0.111 | 0.349 | 0.049 | 0.066 |
| Breadth (%) | | 96.6 | 92.4 | 86.6 | 97.5 | 88.2 | 89.9 | 61.3 | 65.5 |

| IC$_{50}$ (µg/ml) | Breadth (%) |
|---|---|
| <0.1 | >95 |
| 0.1-0.5 | 90-95 |
| 0.5-1 | 80-90 |
| 1-2 | 70-80 |
| 2-5 | 60-70 |
| 5-10 | 50-60 |
| >10 | <50 |

| Virus | Clade | 1-18 | | 1-55 | | 2-12 | | N6 | | 3BNC117 | | VRC01 | |
|---|---|---|---|---|---|---|---|---|---|---|---|---|---|
| | | IC$_{50}$ | IC$_{80}$ | IC$_{50}$ | IC$_{80}$ | IC$_{50}$ | IC$_{80}$ | IC$_{50}$ | IC$_{80}$ | IC$_{50}$ | IC$_{80}$ | IC$_{50}$ | IC$_{80}$ |
| CAP210.2.00.E8 | C | 0.818 | 4.420 | 1.044 | 6.600 | >20 | >20 | >20 | >20 | 9.797 | >20 | >20 | >20 |
| 6545.v4.c1 | AC | 0.004 | 0.020 | 0.013 | 0.046 | 4.100 | >20 | 16.228 | >20 | >20 | >20 | >20 | >20 |
| 89-F1_2_25 | CD | 0.007 | 0.023 | 0.014 | 0.039 | 0.006 | 0.025 | >20 | >5 | >20 | >20 | >20 | >20 |
| 20417927_07 | C | 0.096 | 1.759 | NA | NA | >20 | >20 | >20 | >20 | >20 | >20 | >10 | >10 |
| CAP210_TA5 | C | 0.004 | 4.099 | NA | NA | >20 | >20 | >20 | >20 | 5.720 | >20 | >10 | >10 |
| CAP225_1_06_A2_18 | C | 0.175 | 0.804 | NA | NA | 0.056 | 0.248 | 13.232 | >20 | 6.174 | >20 | 1.170 | 4.740 |

Figure 5

| YU2 Variant | 1-18 | 1-55 | 2-12 | 3BNC117 | VRC01 | N6 | 8ANC131 |
|---|---|---|---|---|---|---|---|
| | | | | IC$_{50}$ (µg/ml) | | | |
| Wild type | 0.019 | 0.021 | 0.045 | 0.029 | 0.107 | 0.047 | 0.206 |
| N279K | 0.006 | 0.006 | 0.010 | >2,5 | >2,5 | 0.224 | >2,5 |
| N280Y | 0.005 | 0.005 | 0.008 | 0.296 | >2,5 | 0.015 | >2,5 |
| T278A + A281T | 0.035 | 0.040 | >2,5 | >2,5 | >2,5 | >2,5 | >2,5 |
| G458D | 0.004 | 0.011 | 0.025 | 0.080 | 0.104 | 0.024 | 1.371 |
| G459D | 0.006 | 0.009 | 0.015 | 0.021 | 0.075 | 0.009 | 0.152 |
| G471R | 0.010 | 0.011 | 0.021 | 0.022 | 0.113 | 0.028 | >2,5 |

IC (µg/ml)

| <0.1 |
|---|
| 0.1-0.5 |
| 0.5-1.0 |
| 1.0-2.5 |
| >2.5 |

Figure 6

| Antibody | Viral strain | |
|---|---|---|
| | 6545.v4.c1 | 89-F1_2_25 |
| | IC50 (µg/ml) | IC50 (µg/ml) |
| 561_01_18 | 0.010 | 0.010 |
| 561_01_21 | 0.015 | 0.006 |
| 561_01_33 | 0.014 | 0.009 |
| 561_01_54 | 0.023 | 0.015 |
| 561_01_55 | 0.008 | 0.010 |
| 561_02_10 | 0.042 | 0.012 |
| 561_02_22 | 0.014 | 0.010 |
| 561_02_27 | 0.012 | 0.011 |
| 561_02_47 | 0.012 | 0.014 |
| 561_03_59 | 0.013 | 0.011 |
| 561_05_18 | 0.012 | 0.016 |
| 561_08_10 | 0.011 | 0.008 |
| 561_09_23 | 0.016 | 0.015 |
| 561_10_07 | 0.013 | 0.010 |
| 561_08_52 | 3.524 | 0.025 |
| 561_09_89 | 1.210 | 0.014 |
| 561_09_71 | 9.369 | 0.019 |
| 561_01_23 | 1.236 | 0.008 |
| 561_01_29 | 2.332 | 0.015 |
| 561_02_12 | 5.175 | 0.012 |
| 561_02_21 | 0.343 | 0.021 |
| 561_03_07 | 2.576 | 0.012 |
| 561_03_78 | 0.973 | 0.016 |

| | | |
|---|---|---|
| N6 | 16.228 | >20 |
| 3BNC117 | >20 | >20 |
| VRC01 | >20 | >20 |
| VRC07 | >20 | >20 |
| VRC07-523-LS | >20 | NA |
| 8ANC131 | >20 | NA |
| NIH45-46 | >20 | >20 |
| NIH45-46G54W | 18.920 | >20 |

| IC (µg/ml) |
|---|
| <0.1 |
| 0.1-0.5 |
| 0.5-1 |
| 1-2 |
| 2-5 |
| 5-10 |
| >10 |

Figure 12

BROADLY NEUTRALIZING ANTIBODIES AGAINST HIV

CROSS REFERENCE TO RELATED APPLICATIONS

This application is the National Stage Entry of International Application No. PCT/EP2020/084309, filed Dec. 2, 2020, which claims the benefit of EP Application Serial No. 19212986.4, filed Dec. 2, 2019, the contents of each of which are hereby incorporated by reference herein in their entirety.

SEQUENCE LISTING

The present specification makes reference to a Sequence Listing (submitted electronically as a txt file named "2013237-0345.txt"). The txt file was generated on Nov. 29, 2022 and is 69,314 bytes in size. The entire contents of the Sequence Listing are herein incorporated by reference.

TECHNICAL FIELD

The present invention relates to monoclonal human antibodies or binding fragments thereof which are directed against the CD4 binding site of the human immunodeficiency virus HIV-1, a pharmaceutical composition comprising such monoclonal human antibodies or binding fragments thereof, a kit comprising such antibodies or binding fragments thereof, and the monoclonal antibodies or binding fragments thereof and the pharmaceutical composition and the kit for use as a medicament, and in the treatment or prevention of a disease caused by the human immunodeficiency virus HIV-1.

BACKGROUND OF THE INVENTION

Broadly neutralizing antibodies (bNAbs) targeting the HIV-1 envelope protein (Env) can prevent infection in animal models and are under investigation for passive immunization in clinical trials. Moreover, bNAbs have been demonstrated to suppress viremia and delay viral rebound after interruption of antiretroviral therapy (ART) in HIV-1-infected individuals.

While these results highlight the significant clinical potential of bNAbs, pre-existing and de novo HIV-1 resistance cause treatment failure and can strongly limit bNAb applications in humans. Strategies to prevent and overcome viral escape are therefore critical to effectively implement bNAb-mediated approaches for HIV-1 prevention and therapy (Gruell, H., and Klein, F. (2018). Antibody-mediated prevention and treatment of HIV-1 infection. Retrovirology 15, 73).

In recent years, potent bNAbs have been isolated from HIV-1-infected donors that target distinct vulnerable epitopes on the HIV-1 envelope (Env) trimer. These epitopes include the CD4 binding site (CD4bs), the V1/V2 loop, the V3 loop glycan patch, the membrane-proximal external region, and the interface between the gp120 and gp41 Env subunits.

Among these sites, the CD4bs is of particular interest because CD4 serves as the primary receptor for viral entry. Most potent CD4bs bNAbs are characterized by the usage of immunoglobulin heavy chain gene segment IGVH1-2*02, high levels of somatic hypermutation, a five-residue complementarity-determining region 3 of the light chain (CDRL3), and mimicry of the Env-CD4 interaction.

Named after the prototypical antibody VRC01 (Wu, X., Yang, Z. Y., Li, Y., Hogerkorp, C. M., Schief, W. R., Seaman, M. S., Zhou, T., Schmidt, S. D., Wu, L., Xu, L., et al. (2010). Rational design of envelope identifies broadly neutralizing human monoclonal antibodies to HIV-1. Science 329, 856-861.), these antibodies are referred to as VRC01-class bNAbs. Additional members of this class include 3BNC117, NIH45-46, N49-P7, N6, and VRC07-523.

Other bNAbs that mimic CD4 binding are derived from the VH1-46 gene segment. However, compared to VH1-2-derived bNAbs, the VH1-46 bNAbs reported to date have lower potencies and breadth that limit their potential for clinical use. For example, CH235.12, one of the best antibodies of this class, is less broad and >10-fold less potent than the VRC01-class bNAb N6 when tested in vitro against a large panel of HIV-1 Env strains (Bonsignori, M., Zhou, T., Sheng, Z., Chen, L., Gao, F., Joyce, M. G., Ozorowski, G., Chuang, G. Y., Schramm, C. A., Wiehe, K., et al. (2016). Maturation Pathway from Germline to Broad HIV-1 Neutralizer of a CD4-Mimic Antibody. Cell 165, 449-463.).

Accordingly, all CD4bs bNAbs that have advanced into clinical testing are members of the VRC01-class (3BNC117, N6, VRC01, and VRC07-523). However, while escape from VRC01 has been associated with a reduction in viral fitness, effects of VRC01-class monotherapy are only transient and were associated with a rapid emergence of viral escape variants both in clinical trials (Scheid, J. F., Horwitz, J. A., Bar-On, Y., Kreider, E. F., Lu, C. L., Lorenzi, J. C., Feldmann, A., Braunschweig, M., Nogueira, L., Oliveira, T., et al. (2016). HIV-1 antibody 3BNC117 suppresses viral rebound in humans during treatment interruption. Nature 535, 556-560.) and animal models of HIV-1 infection (Klein, F., Halper-Stromberg, A., Horwitz J. A., Gruell, H., Scheid J. F., Bournazos S., Mouquet H., Spatz L. A., Diskin R., Abadir A., et al. (2012) HIV Therapy by a Combination of Broadly Neutralizing Antibodies in Humanized Mice. Nature 492 (7427), 118-22).

Due to the shortcomings of the known bNAbs currently under investigation, there remains a demand for HIV antibodies targeting the CD4 binding site which exceed the potency and breadth of known classical VH1-2-derived or VH1-46-derived bNAbs, have potent neutralizing activity against VRC01-class escape variants, and effectively restrict viral escape and maintain viral suppression when tested in HIV-1-infected organisms.

Thus, it is an object of the present invention to provide novel human monoclonal antibodies against HIV-1 having broad neutralizing activity against a wide selection of different virus strains in combination with high neutralization potency against such virus strains. It is a further object of the present invention to provide novel human monoclonal antibodies against HIV-1 which show significant restriction of the development of escape mutations and maintain effectiveness against viruses exhibiting such escape mutations. It is also an object of the present invention to provide novel human monoclonal antibodies against HIV-1 which convey full viral suppression in infected individuals without significant viral rebound during antibody monotherapy. Moreover, it is an object of the present invention to provide novel human monoclonal antibodies against the CD4 binding site that have favorable pharmacokinetic properties in vivo.

SUMMARY OF THE INVENTION

These objects have been solved by the aspects of the present invention as specified hereinafter.

According to the first aspect of the present invention, a monoclonal human antibody or binding fragment thereof directed against the CD4 binding site of the human immunodeficiency virus HIV-1 is provided, wherein the antibody amino acid sequence comprises the $V_H1$-46 gene segment and the $V_K3$-20 gene segment, wherein the antibody comprises either a) the heavy chain amino acid sequence of SEQ ID No. 47 and the light chain amino acid sequence of SEQ ID No. 48, or b) the heavy chain amino acid sequence of SEQ ID No. 49 and the light chain amino acid sequence of SEQ ID No. 50, wherein X in any of SEQ ID No. 47 to SEQ ID No. 50 may be any or no amino acid, or an antibody sequence being at least 80% identical thereto.

According to a preferred embodiment of the first aspect of the present invention, the antibody of alternative b) of the first aspect of the invention comprises a deletion of 2 aa in FWR1.

According to another preferred embodiment of the first aspect of the present invention, the antibody or binding fragment thereof exhibits broad neutralizing activity exemplified by neutralization of at least 11 strains of the 12 HIV-1 isolate reference strains of the global reference panel described in de Camp et al., *J Virol.* 2014 March; 88(5): 2489-2507 when tested in the TZM-bl cell pseudovirus neutralization assay at antibody concentrations up to 25 μg/ml, preferably of all 12 strains.

According to yet another preferred embodiment of the first aspect of the present invention, the antibody or binding fragment thereof exhibits broad neutralizing activity exemplified by neutralization of at least 89.9% (107 of 119), preferably of at least 92.4% (110 of 119), more preferably of at least 96.6% (115 of 119) of pseudoviruses included in the 119-multiclade virus panel described in Schoofs et al., *Immunity,* 2019 Jun. 18; 50(6):1513-1529.e9 when tested in the TZM-bl cell pseudovirus neutralization assay at antibody concentrations up to 20 g/ml.

According to a preferred embodiment of the first aspect of the present invention, the antibody or binding fragment thereof exhibits a neutralization potency (geometric mean $IC_{50}$ of neutralized strains) of less than 0.3 μg/ml, preferably of less than 0.2 μg/ml, more preferably of less than 0.15 μg/ml, even more preferably of less than 0.1 μg/ml, even more preferably of less than 0.05 μg/ml, even more preferably of 0.048 μg/ml, even more preferably of 0.035 μg/ml against the neutralized strains of the global reference panel described in de Camp et al., *J Virol.* 2014 March; 88(5): 2489-2507 when tested in the TZM-bl cell pseudovirus neutralization assay at antibody concentrations up to 25 μg/ml.

According to a preferred embodiment of the first aspect of the present invention, the antibody or binding fragment thereof exhibits a neutralization potency (geometric mean $IC_{50}$ of neutralized strains) of less than 0.2 μg/ml, preferably of less than 0.1 μg/ml, more preferably of less than 0.08 μg/ml, even more preferably of less than 0.05 μg/ml against neutralized strains of the 119-multiclade virus panel described in Schoofs et al., *Immunity,* 2019 Jun. 18; 50(6): 1513-1529.e9 when tested in the TZM-bl cell pseudovirus neutralization assay at antibody concentrations up to 20 μg/ml.

According to another preferred embodiment of the first aspect of the present invention, the antibody or binding fragment thereof exhibits a neutralization potency ($IC_{50}$) of less than 0.05 μg/ml, preferably of less than 0.02 μg/ml, even more preferably of less than 0.01 μg/ml against HIV-1 pseudovirus 89-F1_2_25 (89-F1_2_25$_{env}$; GenBank: HM215349.1) when tested in the TZM-bl pseudovirus neutralization assay.

According to yet another preferred embodiment of the first aspect of the present invention, the antibody or binding fragment neutralizes all of the YU2 pseudovirus variants that comprise the YU2 envelope gene (GenBank: M93258.1) having one of the envelope mutations N279K, N280Y, G458D, G459D, or G471R (residues numbered according to the HIV-1 HXB2 envelope gene; GenBank: K03455) at an $IC_{50}$ concentration of less than 0.1 μg/ml, preferably of less than 0.05 μg/ml when tested in the TZM-bl pseudovirus neutralization assay.

According to one preferred embodiment of the first aspect of the present invention, an initial subcutaneous injection of 1 mg of the antibody or binding fragment thereof followed after 3 to 4 days by regular subcutaneous injections of 0.5 mg of the antibody or binding fragment thereof given between every 3 days and every 4 days to humanized mice infected with HIV-1 NL4-3/YU2, as described in Zhang et al., *J Virol,* 2002 June; 76(12):6332-43, results in a reduction of the HIV-1 RNA load in plasma compared to the start of treatment of at least 0.8 $\log_{10}$, preferably of at least 1.0 $\log_{10}$, in at least 70% of treated mice that have an HIV-1 RNA load of at least 5000 copies/ml plasma at the start of treatment when measured after 4 weeks of therapy, preferably after 6 weeks of therapy, even more preferably after 8 weeks of therapy.

According to a more preferred embodiment of the previous embodiment of the first aspect of the present invention, the humanized mice were previously treated for 4 weeks with one initial subcutaneous injection of 1 mg of 3BNC117 or VRC01 or the combination of both, followed after 3 to 4 days by regular subcutaneous injections of 0.5 mg of 3BNC117 or VRC01 or the combination of both given between every 3 days and every 4 days.

According to a preferred embodiment of the first aspect of the present invention, the initial subcutaneous injection of 1 mg of the antibody or binding fragment thereof followed after 3 to 4 days by regular subcutaneous injections of 0.5 mg of the antibody or binding fragment thereof given between every 3 days and every 4 days to humanized mice infected with HIV-1 NL4-3/YU2, as described in Zhang et al., *J Virol,* 2002 June; 76(12):6332-43, does not for at least 4 weeks lead to the development of a mutation or mutations in the CD4 binding site (loop D, CD4 binding loop, beta23 strand, V5 loop, and beta24) that mediate resistance to the administered antibody.

According to another preferred embodiment of the first aspect of the present invention, the intravenous injection of 0.5 mg of the antibody or binding fragment thereof to NRG mice results in detectable serum levels of the antibody or binding fragment thereof of at least 50 μg IgG/ml serum ten days post-injection.

According to another preferred embodiment of the first aspect of the present invention, the antibody or binding fragment thereof does not comprise a CDRH3 having a length of 16 or 19 amino acids.

According to one preferred embodiment of the first aspect of the present invention, the antibody or binding fragment thereof comprises a CDRH3 having a length of 18, 20 or 21 amino acids.

According to a preferred embodiment of the first aspect of the present invention, the antibody or binding fragment thereof does not comprise or consist of the amino acid sequence of antibodies NC37, NC133, AC40, AC41 or AC72 as described in Freund et al., *Sci. Transl. Med.* 9, eaal2144 (2017).

According to another preferred embodiment of the first aspect of the present invention, the antibody or binding fragment thereof comprises the heavy chain CDR1 to CDR3 and the light chain CDR1 to CDR3 amino acid sequence of one antibody from the group comprising 1-18 (consisting of the heavy chain amino acid sequence of SEQ ID No. 1 and the light chain amino acid sequence of SEQ ID No. 2), 1-21 (consisting of the heavy chain amino acid sequence of SEQ ID No. 3 and the light chain amino acid sequence of SEQ ID No. 4), 1-33 (consisting of the heavy chain amino acid sequence of SEQ ID No. 5 and the light chain amino acid sequence of SEQ ID No. 6), 1-54 (consisting of the heavy chain amino acid sequence of SEQ ID No. 7 and the light chain amino acid sequence of SEQ ID No. 8), 1-55 (consisting of the heavy chain amino acid sequence of SEQ ID No. 9 and the light chain amino acid sequence of SEQ ID No. 10), 2-10 (consisting of the heavy chain amino acid sequence of SEQ ID No. 11 and the light chain amino acid sequence of SEQ ID No. 12), 2-22 (consisting of the heavy chain amino acid sequence of SEQ ID No. 13 and the light chain amino acid sequence of SEQ ID No. 14), 2-27 (consisting of the heavy chain amino acid sequence of SEQ ID No. 15 and the light chain amino acid sequence of SEQ ID No. 16), 2-47 (consisting of the heavy chain amino acid sequence of SEQ ID No. 17 and the light chain amino acid sequence of SEQ ID No. 18), 3-59 (consisting of the heavy chain amino acid sequence of SEQ ID No. 19 and the light chain amino acid sequence of SEQ ID No. 20), 5-18 (consisting of the heavy chain amino acid sequence of SEQ ID No. 21 and the light chain amino acid sequence of SEQ ID No. 22), 8-10 (consisting of the heavy chain amino acid sequence of SEQ ID No. 23 and the light chain amino acid sequence of SEQ ID No. 24), 9-23 (consisting of the heavy chain amino acid sequence of SEQ ID No. 25 and the light chain amino acid sequence of SEQ ID No. 26), 10-7 (consisting of the heavy chain amino acid sequence of SEQ ID No. 27 and the light chain amino acid sequence of SEQ ID No. 28), 8-52 (consisting of the heavy chain amino acid sequence of SEQ ID No. 29 and the light chain amino acid sequence of SEQ ID No. 30), 9-89 (consisting of the heavy chain amino acid sequence of SEQ ID No. 31 and the light chain amino acid sequence of SEQ ID No. 32), 9-71 (consisting of the heavy chain amino acid sequence of SEQ ID No. 33 and the light chain amino acid sequence of SEQ ID No. 34), 1-23 (consisting of the heavy chain amino acid sequence of SEQ ID No. 35 and the light chain amino acid sequence of SEQ ID No. 36), 1-29 (consisting of the heavy chain amino acid sequence of SEQ ID No. 37 and the light chain amino acid sequence of SEQ ID No. 38), 2-12 (consisting of the heavy chain amino acid sequence of SEQ ID No. 39 and the light chain amino acid sequence of SEQ ID No. 40), 2-21 (consisting of the heavy chain amino acid sequence of SEQ ID No. 41 and the light chain amino acid sequence of SEQ ID No. 42), 3-07 (consisting of the heavy chain amino acid sequence of SEQ ID No. 43 and the light chain amino acid sequence of SEQ ID No. 44), 3-78 (consisting of the heavy chain amino acid sequence of SEQ ID No. 45 and the light chain amino acid sequence of SEQ ID No. 46, preferably of one antibody from the group comprising 1-18, 1-33, 1-55, 2-27, 1-23, 1-29, 2-12, 2-21, 3-07 and 3-78, more preferably of one antibody from the group comprising 1-18, 1-55 and 2-12, even more preferably of antibody 1-18 or 2-12, particularly preferably of antibody 1-18.

According to another preferred embodiment of the first aspect of the present invention, the antibody or binding fragment thereof comprises the combination of the heavy chain and the light chain of one antibody selected from the group comprising 1-18 (consisting of the heavy chain amino acid sequence of SEQ ID No. 1 and the light chain amino acid sequence of SEQ ID No. 2), 1-21 (consisting of the heavy chain amino acid sequence of SEQ ID No. 3 and the light chain amino acid sequence of SEQ ID No. 4), 1-33 (consisting of the heavy chain amino acid sequence of SEQ ID No. 5 and the light chain amino acid sequence of SEQ ID No. 6), 1-54 (consisting of the heavy chain amino acid sequence of SEQ ID No. 7 and the light chain amino acid sequence of SEQ ID No. 8), 1-55 (consisting of the heavy chain amino acid sequence of SEQ ID No. 9 and the light chain amino acid sequence of SEQ ID No. 10), 2-10 (consisting of the heavy chain amino acid sequence of SEQ ID No. 11 and the light chain amino acid sequence of SEQ ID No. 12), 2-22 (consisting of the heavy chain amino acid sequence of SEQ ID No. 13 and the light chain amino acid sequence of SEQ ID No. 14), 2-27 (consisting of the heavy chain amino acid sequence of SEQ ID No. 15 and the light chain amino acid sequence of SEQ ID No. 16), 2-47 (consisting of the heavy chain amino acid sequence of SEQ ID No. 17 and the light chain amino acid sequence of SEQ ID No. 18), 3-59 (consisting of the heavy chain amino acid sequence of SEQ ID No. 19 and the light chain amino acid sequence of SEQ ID No. 20), 5-18 (consisting of the heavy chain amino acid sequence of SEQ ID No. 21 and the light chain amino acid sequence of SEQ ID No. 22), 8-10 (consisting of the heavy chain amino acid sequence of SEQ ID No. 23 and the light chain amino acid sequence of SEQ ID No. 24), 9-23 (consisting of the heavy chain amino acid sequence of SEQ ID No. 25 and the light chain amino acid sequence of SEQ ID No. 26), 10-7 (consisting of the heavy chain amino acid sequence of SEQ ID No. 27 and the light chain amino acid sequence of SEQ ID No. 28), 8-52 (consisting of the heavy chain amino acid sequence of SEQ ID No. 29 and the light chain amino acid sequence of SEQ ID No. 30), 9-89 (consisting of the heavy chain amino acid sequence of SEQ ID No. 31 and the light chain amino acid sequence of SEQ ID No. 32), 9-71 (consisting of the heavy chain amino acid sequence of SEQ ID No. 33 and the light chain amino acid sequence of SEQ ID No. 34), 1-23 (consisting of the heavy chain amino acid sequence of SEQ ID No. 35 and the light chain amino acid sequence of SEQ ID No. 36), 1-29 (consisting of the heavy chain amino acid sequence of SEQ ID No. 37 and the light chain amino acid sequence of SEQ ID No. 38), 2-12 (consisting of the heavy chain amino acid sequence of SEQ ID No. 39 and the light chain amino acid sequence of SEQ ID No. 40), 2-21 (consisting of the heavy chain amino acid sequence of SEQ ID No. 41 and the light chain amino acid sequence of SEQ ID No. 42), 3-07 (consisting of the heavy chain amino acid sequence of SEQ ID No. 43 and the light chain amino acid sequence of SEQ ID No. 44), 3-78 (consisting of the heavy chain amino acid sequence of SEQ ID No. 45 and the light chain amino acid sequence of SEQ ID No. 46, preferably of one antibody from the group comprising 1-18, 1-33, 1-55, 2-27, 1-23, 1-29, 2-12, 2-21, 3-07 and 3-78, more preferably of one antibody from the group comprising 1-18, 1-55 and 2-12, even more preferably of antibody 1-18 or 2-12, particularly preferably of antibody 1-18.

According to the second aspect of the present invention, a pharmaceutical composition is provided comprising a monoclonal human antibody or binding fragment thereof according to the first aspect of the present invention, and at least one pharmaceutically acceptable excipient.

According to a preferred embodiment of the second aspect of the present invention, the pharmaceutical composition is a vaccination composition for a human subject.

According to the third aspect of the present invention, a kit is provided comprising a monoclonal human antibody or binding fragment thereof according to the first aspect of the present invention, and a container.

According to the fourth aspect of the present invention, a monoclonal human antibody or binding fragment thereof according to the first aspect of the invention, a pharmaceutical composition according to the second aspect of the invention, or a kit according to the third aspect of the invention are provided for use as a medicament, preferably for use as a vaccine.

According to the fifth aspect of the present invention, a monoclonal human antibody or binding fragment thereof according to the first aspect of the invention, a pharmaceutical composition according to the second aspect of the invention, or a kit according to the third aspect of the invention are provided for use in the treatment or prevention of a disease caused by the human immunodeficiency virus HIV-1 in human subjects, preferably for use in the treatment or prevention of acquired immune deficiency syndrome (AIDS) in human subjects.

DESCRIPTION OF FIGURES

FIG. 1 shows the neutralizing activity of antibodies of the invention against a panel of 12 global reference pseudovirus strains with different envelope amino acid sequences (as described in de Camp et al., *J Virol.* 2014 March; 88(5): 2489-2507) when tested in the TZM-bl cell pseudovirus neutralization assay. The tested antibodies demonstrate high potency against the neutralized strains, and neutralize at least 92% (11/12) and up to all tested pseudoviruses.

FIG. 3 shows the neutralizing activity (IC$_{50}$) of antibodies against a multiclade panel of 119 pseudoviruses with different HIV-1 envelope amino acid sequences (as described in Schoofs et al., Immunity, 2019 Jun. 18; 50(6):1513-1529.e9) when tested in the TZM-bl cell pseudovirus neutralization assay. Data for antibodies 1-18, 1-55, and 2-12, clinically advanced VH1-2-derived CD4 binding site antibodies (3BNC117, VRC01, and N6), and V3 loop-targeting antibodies (10-1074, PGT121) are shown.

FIG. 5 shows the neutralizing activity of antibodies against a selection of pseudoviruses with different envelope amino acid sequences as measured by the TZM-bl cell pseudovirus assay.

FIG. 6 shows the neutralizing activity of antibodies 1-18, 1-55, and 2-12 against a panel of HIV-1 YU2 pseudoviruses with different envelope sequence single amino acid mutations in the CD4 binding site as indicated on the left and as measured in the TZM-bl cell pseudovirus neutralization assay, compared to the CD4 binding site antibodies 3BNC117, VRC01, N6, and the VH1-46-derived antibody 8ANC131 are shown. Mutated envelope residues are numbered according to the HIV-1$_{HXB2}$ reference strain.

FIG. 12 shows the neutralizing activity ($IC_{50}$) of antibodies against the 6545.v4.c1 and 89-F1_2_25 HIV-1 pseudovirus strains, respectively, as determined in the TZM-bl cell pseudovirus assay. Antibodies of the invention are compared to HIV-1 neutralizing CD4 binding site antibodies N6, 3BNC117, VRC01, VRC07, VRC07-523-LS, 8ANC131, NIH45-46 and NIH45-46G54W.

DETAILED DESCRIPTION OF THE INVENTION

Figure 2:
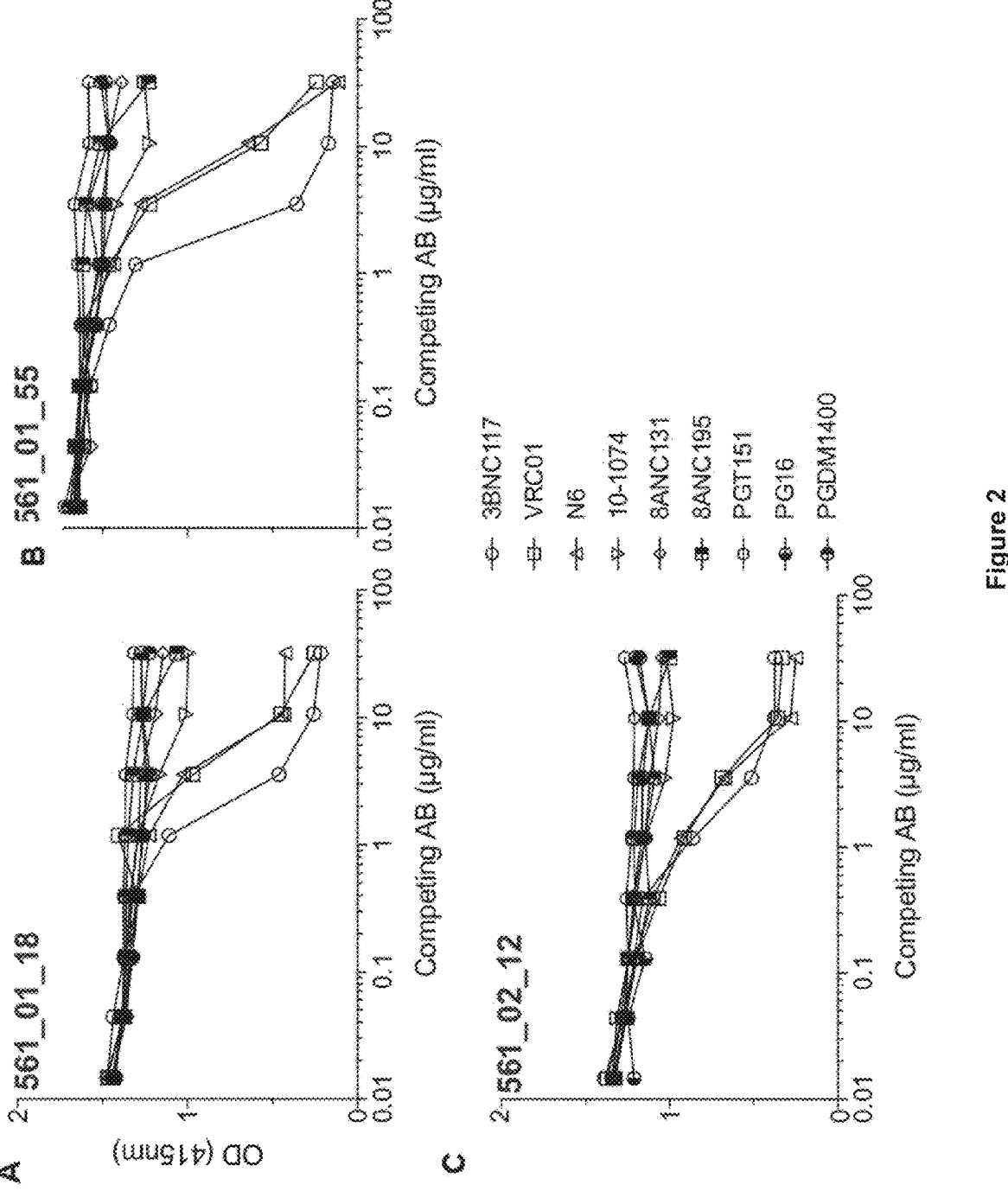
FIG. 2 shows the binding of antibodies 1-18 (FIG. 2A), 1-55 (FIG. 2B), and 2-12 (FIG. 2C) against the HIV-1 Env protein of BG505$_{SOSIP.664}$ in a competition ELISA after pre-incubation with increasing amounts of the competing antibody (x-axis). The tested antibodies show reduced binding to the BG505$_{SOSIP.664}$ envelope protein after pre-incubation with the CD4 binding site targeting antibodies 3BNC117, VRC01 and N6, indicating that the antibodies share an epitope that overlaps the CD4 binding site.

The present inventors have dedicated themselves to solving the problem of the present invention and were successful to find novel and useful human monoclonal antibodies against HIV-1 which overcome the disadvantages and shortcomings of known antibodies.

Herein, the inventors describe novel $V_H$1-46- and $V_K$3-20-derived CD4 binding site antibodies that exceed the potency and breadth of classical $V_H$1-46- and $V_H$1-2-derived bNAbs. The structural basis of the observed high activity is thought to be caused by common structural properties. These properties are based on the combination of $V_H$1-46- and $V_K$3-20-derived sequence analogies which are further defined by consensus sequences showing residues crucial for their activity.

Of particular interest, compared to 3BNC117 and VRC01, the two most clinically-advanced CD4bs bNAbs, antibodies according to the invention effectively restrict viral escape and maintain both neutralizing activity against VRC01-class escape variants and full viral suppression when tested in HIV-1-infected humanized mice. Therefore, the inventive antibodies include highly promising candidates for antibody-mediated strategies to effectively treat and prevent HIV-1 infection.

Thus, the present invention provides monoclonal human antibodies or binding fragment thereof directed against the CD4 binding site of the human immunodeficiency virus HIV-1, wherein the antibody sequence comprises the $V_H$1-46 gene segment and the $V_K$3-20 gene segment, wherein the antibody comprises a) the heavy chain sequence QXXXFQSGXEXKRPGASVXISCRADDDPY-TDDDTFTKYXTHWIRQAPGQXPEWLGVISPHXA RPIYSYKFXDRLTL-TRDSSLTXVYXELXXLXXDDXGIYXCARDPFGXXX-PHYNXHMDVWGXGT XXIVSX (Consensus sequence No. 1; SEQ ID No. 47) and the light chain sequence EXVLTQSPAILSXSPGDRVXXSCXAS-ZGLXXXXLAWYRFKXGQIPXLVJFXXSXRARG-TPDRFX GXGSXXDFTLTIXXVZXEDFA- TYYCQRXGXTPITFGGGTXLDXX (Consensus sequence No. 2; SEQ ID No. 48), or b) the heavy chain sequence QLXQXGGGVXXPGASVXXSCXXPEXTFT-KYXJHWXRQAPGXGXEWXGXVSPHGGRPXXXXX FRDRLTXTRXIHXTTHXMXLXGLXXXDXXXYX-CARDXXGEXXXXXXXXXXXMDXWGGGXXXX VXS (Consensus sequence No. 3; SEQ ID No. 49) and the light chain sequence XXXLTQSPXTLSXSPGEXXXLSCRAXXGXXXXHX-XWFQXXXGXXPRLLIFXXXRRAXGXXXRF XXXXXXXXXXXXLTIXXVEXXDFAXYXCQXYGX-ITPJXFGGGTXXDXK (Consensus sequence No. 4; SEQ ID No. 50), wherein X in any of SEQ ID No. 47 to SEQ ID No. 50 may be any or no amino acid, or an antibody sequence being at least 80% identical thereto.

Within the context of the present invention, the antibodies, which have been generated and described herein, may be used and claimed as the complete monoclonal human antibody or as any functional or binding fragment thereof. Preferably, the monoclonal human antibody or any kind of functional or binding fragment thereof should at least comprise the complementarity determining regions (CDR) 1 to 3 of the heavy chain and CDR 1 to 3 of the light chain of the human monoclonal antibody.

The CDR regions of the antibody sequences described herein are preferably defined according to the numbering scheme of IMGT which is an adaptation of the numbering scheme of Chothia (ImMunoGeneTics information System®; Lefranc et al., NAR 27:209-212 (1999); http://www.imgt.org).

In one preferred embodiment, the antibody is a monoclonal antibody or a fragment thereof that retains binding specificity and ability to neutralize infectious pathogen. In one preferred embodiment, the antibody is an IgG1, IgG2, IgG3, or IgG4 antibody. For example, the antibody may be an antibody comprising an Fc domain of any human IgG isotype (e.g. IgG1, IgG2, IgG3, or IgG4).

Optionally, the antigen-binding compound consists of or comprises a Fab, Fab', Fab'-SH, F(ab)$_2$, Fv, a diabody, single-chain antibody fragment, or a multispecific antibody comprising multiple different antibody fragments.

Within the present invention, an antibody or binding fragment directed against the CD4 binding site of HIV-1 means an antibody binding to the CD4 binding site region within the gp 120 envelope glycoprotein of HIV-1 with an at least 10-fold, more preferably at least 50-fold, particularly preferably at least 100-fold increased affinity compared to unrelated epitopes, proteins or protein regions. In general, the term CD4 binding site herein designates the CD4 binding site region within the gp120 envelope glycoprotein of HIV-1.

Further within the present invention, an antibody amino acid sequence comprising the $V_H$1-46 gene segment and the $V_K$3-20 gene segment, respectively, means an antibody amino acid sequence which is based on and/or has been derived from said gene segments. It is commonly known in the art how to determine which $V_H$ or $V_K$ gene segments are used to assemble an antibody amino acid sequence. While mutations of said gene segments commonly occur in the assembly of a natural antibody, it will be readily apparent to the skilled person which primary sequence requirements are set forth by requiring the use of the $V_H$1-46 gene segment and the $V_K$3-20 gene segment for composing a specific antibody.

Thus, the monoclonal antibody or binding fragment thereof shall preferably be understood as comprising sequence which can naturally be derived from the combination of the $V_H1$-46 gene segment and the $V_K3$-20 gene segment. This would preferably include a naturally occurring degree of mutagenesis of said gene segments.

To understand the significance and the influence of these two segments on the overall structural basis of the claimed antibodies, it should be noted that $V_H1$-46 is responsible for 104 amino acids of the total of 131 amino acids in the heavy chain according to Consensus Sequence No. 1, and for 96 amino acids of the total of 126 amino acids in the heavy chain according to Consensus Sequence No. 3.

Similarly, $V_K3$-20 accounts for 96 amino acids of the total of 108 amino acids in the light chain according to Consensus Sequence No. 2 and for 98 amino acids of the total of 111 amino acids in the light chain according to Consensus Sequence No. 4.

Based on the number of functional antibodies that the inventors were able to identify, it became further possible to formulate two sets of consensus sequences for antibodies comprising the $V_H1$-46 gene segment and the $V_K3$-20 gene segment and being directed against the CD4 binding site of HIV-1. These two sets appear to represent different primary sequence approaches to realize highly efficient binding to the CD4 binding site, restriction of viral escape as well as breadth and potency of virus neutralization.

The first set of sequences consists of Consensus sequence No. 1 according to SEQ ID No. 47 for the heavy chain and Consensus sequence No. 2 according to SEQ ID No. 48 for the light chain. Many individualized sequences conforming to these consensus sequences have been studied herein and the results obtained therewith make it plausible that the combination of the consensus sequences with the defined segments give sufficient structural guidance to obtain a set of functional antibodies. In addition, two representatives of the set of antibodies conforming to the first set of sequences are antibodies 1-18 and 1-55 which have been studied in even greater detail.

The second set of sequences consists of Consensus sequence No. 3 according to SEQ ID No. 49 for the heavy chain and Consensus sequence No. 2 according to SEQ ID No. 50 for the light chain. Again, many individualized sequences have been studied herein as examples of the second set of consensus sequences and the results obtained therewith also make it plausible that the combination of these consensus sequences with the defined segments give sufficient structural guidance to obtain functional antibodies. In addition, one representative of the set of antibodies conforming to the second set of sequences is antibody 2-12 which has also been studied in even greater detail.

Regarding the consensus sequences described herein, X or Xaa within the amino acid sequence may represent any amino acid or no amino acid. However, based on the additional requirement that the claimed antibodies shall comprise the $V_H1$-46 gene segment and the $V_K3$-20 gene segment, it is clear to a skilled person that options are more limited by these gene segments forming the underlying groundwork for each antibody.

In general, the monoclonal human antibodies or binding fragments thereof as described herein further encompass antibody amino acid sequences being at least 80% identical to the sequences as defined above as long as they are still directed against the CD4 binding site of the human immunodeficiency virus HIV-1. This is meant to include sequences having trivial mutations of the antibody amino acid sequence which do not interfere with structural folds and the affinity of the antibody to the CD4 binding site.

It is a trivial task for a skilled person to determine if an antibody which exhibits a certain degree of identity is directed against the CD4 binding site of the human immunodeficiency virus HIV-1 based on the above or the common general knowledge.

The determination of percent identity between two sequences is accomplished according to the present invention by using the mathematical algorithm of Karlin and Altschul (Proc. Natl. Acad. Sci. USA (1993) 90: 5873-5877). Such an algorithm is the basis of the BLASTN and BLASTP programs of Altschul et al. (J. Mol. Biol. (1990) 215: 403-410). BLAST nucleotide searches are performed with the BLASTN program. To obtain gapped alignments for comparative purposes, Gapped BLAST is utilized as described by Altschul et al. (Nucleic Acids Res. (1997) 25: 3389-3402). When utilizing BLAST and Gapped BLAST programs, the default parameters of the respective programs are used.

According to a preferred embodiment of the present invention, antibody amino acid sequences form part of the invention which consist of or comprise a nucleic acid sequence being at least 85% identical to the sequences defined above and disclosed herein, more preferably at least 90% identical, even more preferred at least 95% identical.

According to a preferred embodiment of the present invention, the antibody of alternative b) of the first aspect of the invention comprises a deletion of 2 aa in FWR1.

According to another preferred embodiment of the invention, the monoclonal human antibody or binding fragment thereof exhibits broadly neutralizing activity exemplified by neutralization of at least 11 strains of the 12 HIV-1 isolate reference strains of the global reference panel described in de Camp et al., *J Virol.* 2014 March; 88(5): 2489-2507 when tested in the TZM-bl cell pseudovirus neutralization assay at antibody concentrations up to 25 μg/ml, preferably of all 12 strains.

The TZM-bl cell pseudovirus neutralization assay is a highly standardized assay which is commonly used in the art and in the technical field of the invention for an analysis of neutralization potency of antibodies against various HIV-1 strains. In brief, antibodies and virus strains are incubated together before TZM-bl target cells are added. These cells exhibit luciferase activity in case of a successful infection, resulting in a detectable luminescence signal in the presence of luciferin after lysis of cells. Neutralizing antibodies are able to prevent infection and therefore the generation of luminescence. The potency of a neutralizing antibody is determined by the concentration of the antibody required to reduce virus infectivity by a particular amount.

A standardized way of setting up and employing this assay is disclosed and described in detail in Sarzotti-Kelsoe et al.; *J Immunol Methods.* 2014 July; 0: 131-146. doi: 10.1016/j.jim.2013.11.022. This description alone and in combination with the common prior art enables the skilled person to establish and determine a conclusive readout of the TZM-bl cell pseudovirus neutralization assay as used herein.

The global reference panel described in de Camp et al., *J Virol.* 2014 March; 88(5): 2489-2507 comprises a representative selection of 12 HIV-1 virus variants. The spectrum of HIV-1 serum neutralizing activity seen with this 12-virus panel is commonly accepted to closely approximate the activity seen with subtype-matched viruses. Moreover, this panel is highly sensitive for detection of many of the known broadly neutralizing antibodies. Studies carried out with this panel allow a reliable prediction of the neutralization breadth and/or potency of a given antibody.

According to another preferred embodiment of the first aspect of the present invention, the antibody or binding fragment thereof exhibits broad neutralizing activity exemplified by neutralization of at least 89.9% (107 of 119), preferably of at least 92.4% (110 of 119), even more preferably of at least 96.6% (115 of 119) of pseudoviruses included in the 119-multiclade virus panel described in Schoofs et al., *Immunity,* 2019 Jun. 18; 50(6):1513-1529.e9 when tested in the TZM-bl cell pseudovirus neutralization assay at antibody concentrations up to 20 µg/ml.

The more comprehensive panel according to and referenced in Schoofs et al., 2019 serves to exactly identify the breadth and potency by testing a high number of different pseudoviruses (i.e., HIV-1 strains). This large panel is commonly accepted as being representative of all major circulating HIV-1 clades and provides detailed information on the neutralization abilities of antibodies examined.

According to a preferred embodiment of the first aspect of the present invention, the antibody or binding fragment thereof exhibits a neutralization potency (geometric mean $IC_{50}$) of less than 0.3 µg/ml, preferably of less than 0.2 µg/ml, more preferably of less than 0.15 µg/ml, even more preferably of less than 0.1 µg/ml, even more preferably of less than 0.05 µg/ml, even more preferably of 0.048 µg/ml, even more preferably of 0.035 µg/ml against the neutralized strains of the global reference panel described in de Camp et al., *J Virol.* 2014 March; 88(5): 2489-2507 when tested in the TZM-bl cell pseudovirus neutralization assay at antibody concentrations up to 25 µg/ml.

Neutralization potency as defined herein preferably takes only those virus variants into account that could positively be determined as being neutralized by the respective antibodies. Based on the selection of positively neutralized variants, a geometric mean $IC_{50}$ is then determined across the neutralized strains.

According to a preferred embodiment of the first aspect of the present invention, the antibody or binding fragment thereof exhibits a neutralization potency (geometric mean $IC_{50}$) of less than 0.2 µg/ml, preferably of less than 0.1 µg/ml, more preferably of less than 0.08 µg/ml, even more preferably of less than 0.05 µg/ml against neutralized strains of the 119-multiclade virus panel described in Schoofs et al., *Immunity,* 2019 Jun. 18; 50(6):1513-1529.e9 when tested in the TZM-bl cell pseudovirus neutralization assay at antibody concentrations up to 20 µg/ml.

According to another preferred embodiment of the first aspect of the present invention, the antibody or binding fragment thereof exhibits a neutralization potency ($IC_{50}$) of less than 0.05 µg/ml, preferably of less than 0.02 µg/ml, more preferably of at most 0.01 µg/ml, even more preferably of less than 0.01 µg/ml against HIV-1 pseudovirus 89-F1_2_25 (89-F1_2_25 env gene, GenBank: HM215349.1) when tested in the TZM-bl pseudovirus neutralization assay.

According to another preferred embodiment of the first aspect of the present invention, the antibody or binding fragment thereof exhibits a neutralization potency ($IC_{50}$) of less than 10 µg/ml, preferably of less than 1 µg/ml, more preferably of less than 0.5 µg/ml, even more preferably less than 0.05 µg/ml, even more preferably at most 0.01 µg/ml, particularly preferably less than 0.01 µg/ml against HIV-1 pseudovirus 6546.v4.c1 (6546.v4.c1 env gene, GenBank: HM215332.1) when tested in the TZM-bl pseudovirus neutralization assay.

The HIV-1 pseudovirus 89-F1_2_25 appears to be one of the most difficult strains for neutralization by known CD4 binding site antibodies. In fact, none of the previously known antibodies targeting the CD4 binding site has yet been demonstrated to successfully neutralize said pseudovirus at $IC_{50}$ values below 0.194 µg/ml. However, antibodies according to the invention are able to neutralize said strain with a much higher potency.

HIV-1 pseudovirus 6545.v4.c1 also appears to be a highly difficult strain for neutralization by CD4 binding site antibodies. None of the previously known antibodies targeting the CD4 binding site has yet been demonstrated to successfully neutralize said pseudovirus at $IC_{50}$ values below 0.091 µg/ml. However, there are antibodies according to the invention which are able to neutralize said strain with a much higher potency.

According to one preferred embodiment of the present invention, the antibody or binding fragment neutralizes all of the YU2 pseudovirus variants that comprise the YU2 envelope gene (GenBank: M93258.1) having one of the envelope mutations N279K, N280Y, G458D, G459D, or G471R (residues numbered according to the HIV-1 HXB2 envelope gene; GenBank: K03455) at an $IC_{50}$ concentration of less than 0.1 µg/ml, preferably of less than 0.05 µg/ml when tested in the TZM-bl pseudovirus neutralization assay.

Mutations N279K, N280Y, G458D, and G459D have been associated with the development of viral rebound during therapy with CD4 binding site antibodies (i.e., treatment failure) in in vivo models of HIV-1 infection and are indicating the development of viral resistance against the administered CD4 binding site antibodies (Klein et al., *Nature,* 2012 Dec. 6; 492(7427):118-22; Horwitz et al, *Proc Natl Acad Sci USA,* 2013 Oct. 8; 110(41):16538-43). Again, the antibodies according to the present invention are superior to known CD4 binding site antibodies of the prior art in that the mutations in the YU2 envelope gene mentioned above do not abolish neutralization and do not serve as escape mutations against antibodies according to the invention.

According to another preferred embodiment of the present invention, an initial subcutaneous injection of 1 mg of the antibody or binding fragment thereof followed after 3 to 4 days by regular subcutaneous injections of 0.5 mg of the antibody or binding fragment thereof given between every 3 days and every 4 days to humanized mice infected with HIV-1 NL4-3/YU2, as described in Zhang et al., *J Virol,* 2002 June; 76(12):6332-43, results in a reduction of the HIV-1 RNA load in plasma compared to the start of treatment of at least 0.8 $\log_{10}$, preferably of at least 1.0 $\log_{10}$, in at least 70% of treated mice that have an HIV-1 RNA load of at least 5000 copies/ml plasma at the start of treatment when measured after 4 weeks of therapy, preferably after 6 weeks of therapy, even more preferably after 8 weeks of therapy.

According to another preferred embodiment of the present invention, an initial subcutaneous injection of 1 mg of the antibody or binding fragment thereof followed after 3 to 4 days by regular subcutaneous injections of 0.5 mg of the antibody or binding fragment thereof given between every 3 days and every 4 days to humanized mice infected with HIV-1 NL4-3/BAL, results in a reduction of the HIV-1 RNA load in plasma compared to the start of treatment of at least 1.0 $\log_{10}$, preferably of at least 1.5 $\log_{10}$, even more preferably of at least 1.75 $\log_{10}$ in at least 60% of treated mice that have an HIV-1 RNA load of at least 30,000 copies/ml plasma at the start of treatment when measured after 4 weeks of therapy, even more preferably after 6 weeks of therapy.

According to a more preferred embodiment of the previous embodiment, the humanized mice were previously treated for 4 weeks with one initial subcutaneous injection of 1 mg of 3BNC117 or VRC01 or the combination of both, followed after 3 to 4 days by regular subcutaneous injections of 0.5 mg of 3BNC117 or VRC01 or the combination of both given between every 3 days and every 4 days.

Humanized mice infected with HIV-1 NL4-3/YU2 (YU2 env in NL4-3 backbone as described in Zhang et al., *J Virol,* 2002; 76:6332-6343) provide a well-established model in the field to study the antiviral activity of neutralizing HIV-1 antibodies in vivo. These mice can maintain stable levels of viremia (i.e., HIV-1 RNA copy numbers in plasma) and show a rate of HIV-1 sequence diversification in the env gene that is similar to what is observed in humans (Klein et al., *Nature,* 2012 Dec. 6; 492(7427):118-22).

This model has also been used to investigate the effects of monotherapy with CD4 binding site antibodies (Freund et al., *PLoS Pathog,* 2015 Oct. 30; 11(10):e1005238; Klein et al., *Nature,* 2012 Dec. 6; 492(7427):118-22; Horwitz et al, *Proc Natl Acad Sci USA,* 2013 Oct. 8; 110(41):16538-43; Freund et al., *Sci Transl Med,* 2017 Jan. 18; 9(373). pii: eaal2144). Antibodies according to the invention that are given as monotherapy lead to maintained suppression of the HIV-1 viral load in treated mice and are therefore superior to the other studied CD4 binding site antibodies, in which only transient reductions of the HIV-1 viral load during antibody monotherapy are observed. Moreover, the in vivo activity of 1-18 is superior to other CD4 binding site antibodies in the respect that maintained viral suppression is also achieved after mice developed viral rebound during previous treatment with the CD4 binding site antibodies 3BNC117, VRC01, or the combination of both.

According to one preferred embodiment of the first aspect of the present invention, the initial subcutaneous injection of 1 mg of the antibody or binding fragment thereof followed after 3 to 4 days by regular subcutaneous injections of 0.5 mg of the antibody or binding fragment thereof given between every 3 days and every 4 days to humanized mice infected with HIV-1 NL4-3/YU2, as described in Zhang et al., *J Virol,* 2002 June; 76(12):6332-43, does not for at least 4 weeks lead to the development of a mutation or mutations in the CD4 binding site (loop D, CD4 binding loop, beta23 strand, V5 loop, and beta24 strand) that mediate resistance to the administered antibody.

Preferably, resistance to the administered antibody as used in the context of the previous embodiment may be defined as resulting in an $IC_{50}$ of the administered antibody of at least 2.5 µg/ml in a TZM-bl neutralization pseudovirus assay when an HIV-1 pseudovirus generated with a virus sequence containing this mutation is tested.

Development of escape mutations resulting in antibody resistance and/or associated with viral rebound (i.e., treatment failure) has been demonstrated in the antibody monotherapy studies of other CD4 binding site antibodies (Freund et al., *PLoS Pathog,* 2015 Oct. 30; 11(10):e1005238; Klein et al., *Nature,* 2012 Dec. 6; 492(7427):118-22; Horwitz et al, *Proc Natl Acad Sci USA,* 2013 Oct. 8; 110(41):16538-43; Freund et al., *Sci Transl Med,* 2017 Jan. 18; 9(373). pii: eaal2144). Compared to these CD4 binding site antibodies, the antibodies of the invention are superior in that they prevent the development of mutations in the CD4 binding site epitope and therefore can prevent treatment failure and maintain antiviral activity.

According to another preferred embodiment of the first aspect of the present invention, the intravenous injection of 0.5 mg of the antibody or binding fragment thereof to NRG mice, results in detectable serum levels of the antibody or binding fragment thereof of at least 50 µg IgG/ml serum ten days post-injection.

HIV-1 neutralizing antibodies can vary in their pharmacokinetic properties. In humans, the currently known CD4 binding site antibodies appear to have a shorter half-life than antibodies that target the V3 loop (Mendoza et al., *Nature,* 2018 September; 561(7724):479-484), an observation that is also made in mouse models (Klein et al., *Nature,* 2012 Dec. 6; 492(7427):118-22; Horwitz et al, *Proc Natl Acad Sci USA,* 2013 Oct. 8; 110(41):16538-43). Compared to other CD4 binding site antibodies, the antibodies of the invention are superior because they maintain higher serum levels for a longer period in vivo.

According to a preferred embodiment of the first aspect of the present invention, the antibody or binding fragment thereof does not comprise a CDRH3 having a length of 16 or 19 amino acids and/or wherein the antibody or binding fragment thereof comprises a CDRH3 having a length of 18, 20 or 21 amino acids.

According to one preferred embodiment of the first aspect of the present invention, the antibody or binding fragment thereof does not comprise or consist of the amino acid sequence of antibodies NC37, NC133, AC40, AC41 or AC72 as described in Freund et al., *Sci. Transl. Med.* 9, eaal2144 (2017).

According to a preferred embodiment of the first aspect of the present invention, the antibody or binding fragment thereof comprises the heavy chain CDR1 to CDR3 and the light chain CDR1 to CDR3 amino acid sequence of one antibody from the group comprising 1-18 (consisting of the heavy chain amino acid sequence of SEQ ID No. 1 and the light chain amino acid sequence of SEQ ID No. 2), 1-21 (consisting of the heavy chain amino acid sequence of SEQ ID No. 3 and the light chain amino acid sequence of SEQ ID No. 4), 1-33 (consisting of the heavy chain amino acid sequence of SEQ ID No. 5 and the light chain amino acid sequence of SEQ ID No. 6), 1-54 (consisting of the heavy chain amino acid sequence of SEQ ID No. 7 and the light chain amino acid sequence of SEQ ID No. 8), 1-55 (consisting of the heavy chain amino acid sequence of SEQ ID No. 9 and the light chain amino acid sequence of SEQ ID No. 10), 2-10 (consisting of the heavy chain amino acid sequence of SEQ ID No. 11 and the light chain amino acid sequence of SEQ ID No. 12), 2-22 (consisting of the heavy chain amino acid sequence of SEQ ID No. 13 and the light chain amino acid sequence of SEQ ID No. 14), 2-27 (consisting of the heavy chain amino acid sequence of SEQ ID No. 15 and the light chain amino acid sequence of SEQ ID No. 16), 2-47 (consisting of the heavy chain amino acid sequence of SEQ ID No. 17 and the light chain amino acid sequence of SEQ ID No. 18), 3-59 (consisting of the heavy chain amino acid sequence of SEQ ID No. 19 and the light chain amino acid sequence of SEQ ID No. 20), 5-18 (consisting of the heavy chain amino acid sequence of SEQ ID No. 21 and the light chain amino acid sequence of SEQ ID No. 22), 8-10 (consisting of the heavy chain amino acid sequence of SEQ ID No. 23 and the light chain amino acid sequence of SEQ ID No. 24), 9-23 (consisting of the heavy chain amino acid sequence of SEQ ID No. 25 and the light chain amino acid sequence of SEQ ID No. 26), 10-7 (consisting of the heavy chain amino acid sequence of SEQ ID No. 27 and the light chain amino acid sequence of SEQ ID No. 28), 8-52 (consisting of the heavy chain amino acid sequence of SEQ ID No. 29 and the light chain amino acid sequence of SEQ ID No. 30), 9-89 (consisting of the heavy chain amino acid sequence of SEQ ID No. 31 and the light chain amino acid sequence of SEQ ID No. 32), 9-71 (consisting of the heavy chain amino acid sequence of SEQ ID No. 33 and the light chain amino acid sequence of SEQ ID No. 34), 1-23 (consisting of the heavy chain amino acid sequence of SEQ ID No. 35 and the light chain amino acid sequence of SEQ ID No. 36), 1-29 (consisting of the heavy chain amino acid sequence of SEQ ID No. 37 and the light chain amino acid sequence of SEQ ID No. 38), 2-12 (consisting of the heavy chain amino acid sequence of SEQ ID No. 39 and the light chain amino acid sequence of SEQ ID No. 40), 2-21 (consisting of the heavy chain amino acid sequence of SEQ ID No. 41 and the light chain amino acid sequence of SEQ ID No. 42), 3-07 (consisting of the heavy chain amino acid sequence of SEQ ID No. 43 and the light chain amino acid sequence of SEQ ID No. 44), 3-78 (consisting of the heavy chain amino acid sequence of SEQ ID No. 45 and the light chain amino acid sequence of SEQ ID No. 46, preferably of one antibody from the group comprising 1-18, 1-33, 1-55, 2-27, 1-23, 1-29, 2-12, 2-21, 3-07 and 3-78, more preferably of one antibody from the group comprising 1-18, 1-55 and 2-12, even more preferably of antibody 1-18 or 2-12, particularly preferably of antibody 1-18.

According to a specifically preferred embodiment of the present invention, the antibody or binding fragment thereof comprises the combination of the heavy chain and the light chain of one antibody selected from the group comprising 1-18 (consisting of the heavy chain amino acid sequence of SEQ ID No. 1 and the light chain amino acid sequence of SEQ ID No. 2), 1-21 (consisting of the heavy chain amino acid sequence of SEQ ID No. 3 and the light chain amino acid sequence of SEQ ID No. 4), 1-33 (consisting of the heavy chain amino acid sequence of SEQ ID No. 5 and the light chain amino acid sequence of SEQ ID No. 6), 1-54 (consisting of the heavy chain amino acid sequence of SEQ ID No. 7 and the light chain amino acid sequence of SEQ ID No. 8), 1-55 (consisting of the heavy chain amino acid sequence of SEQ ID No. 9 and the light chain amino acid sequence of SEQ ID No. 10), 2-10 (consisting of the heavy chain amino acid sequence of SEQ ID No. 11 and the light chain amino acid sequence of SEQ ID No. 12), 2-22 (consisting of the heavy chain amino acid sequence of SEQ ID No. 13 and the light chain amino acid sequence of SEQ ID No. 14), 2-27 (consisting of the heavy chain amino acid sequence of SEQ ID No. 15 and the light chain amino acid sequence of SEQ ID No. 16), 2-47 (consisting of the heavy chain amino acid sequence of SEQ ID No. 17 and the light chain amino acid sequence of SEQ ID No. 18), 3-59 (consisting of the heavy chain amino acid sequence of SEQ ID No. 19 and the light chain amino acid sequence of SEQ ID No. 20), 5-18 (consisting of the heavy chain amino acid sequence of SEQ ID No. 21 and the light chain amino acid sequence of SEQ ID No. 22), 8-10 (consisting of the heavy chain amino acid sequence of SEQ ID No. 23 and the light chain amino acid sequence of SEQ ID No. 24), 9-23 (consisting of the heavy chain amino acid sequence of SEQ ID No. 25 and the light chain amino acid sequence of SEQ ID No. 26), 10-7 (consisting of the heavy chain amino acid sequence of SEQ ID No. 27 and the light chain amino acid sequence of SEQ ID No. 28), 8-52 (consisting of the heavy chain amino acid sequence of SEQ ID No. 29 and the light chain amino acid sequence of SEQ ID No. 30), 9-89 (consisting of the heavy chain amino acid sequence of SEQ ID No. 31 and the light chain amino acid sequence of SEQ ID No. 32), 9-71 (consisting of the heavy chain amino acid sequence of SEQ ID No. 33 and the light chain amino acid sequence of SEQ ID No. 34), 1-23 (consisting of the heavy chain amino acid sequence of SEQ ID No. 35 and the light chain amino acid sequence of SEQ ID No. 36), 1-29 (consisting of the heavy chain amino acid sequence of SEQ ID No. 37 and the light chain amino acid sequence of SEQ ID No. 38), 2-12 (consisting of the heavy chain amino acid sequence of SEQ ID No. 39 and the light chain amino acid sequence of SEQ ID No. 40), 2-21 (consisting of the heavy chain amino acid sequence of SEQ ID No. 41 and the light chain amino acid sequence of SEQ ID No. 42), 3-07 (consisting of the heavy chain amino acid sequence of SEQ ID No. 43 and the light chain amino acid sequence of SEQ ID No. 44), 3-78 (consisting of the heavy chain amino acid sequence of SEQ ID No. 45 and the light chain amino acid sequence of SEQ ID No. 46, preferably of one antibody from the group comprising 1-18, 1-33, 1-55, 2-27, 1-23, 1-29, 2-12, 2-21, 3-07 and 3-78, more preferably of one antibody from the group comprising 1-18, 1-55 and 2-12, even more preferably of antibody 1-18 or 2-12, particularly preferably of antibody 1-18.

In the description of the present application, antibody designations may be used. It is pointed out that the antibodies consist of heavy and light chains which also form part of the present description. If reference is made to an antibody by its designation or to a SEQ ID No., it should be understood that these ways of reference are interchangeable.

The present invention further relates to a pharmaceutical composition comprising a monoclonal human antibody or binding fragment thereof according to the invention as defined and further described herein and at least one pharmaceutically acceptable excipient. Preferably, the pharmaceutical composition is a vaccination composition for a human subject.

The present invention also encompasses a kit comprising a monoclonal human antibody or binding fragment thereof according to the invention as defined and further described herein and a container.

In one aspect, the present invention is also directed to the monoclonal human antibody or binding fragment thereof according to the invention as defined and further described herein, the pharmaceutical composition as described herein and the kit for use as a medicament, preferably for use as a vaccine.

In another aspect, the present invention is also directed to the monoclonal human antibody or binding fragment thereof according to the invention as defined and further described herein, the pharmaceutical composition as described herein and the kit for use in the treatment or prevention of a disease caused by the human immunodeficiency virus HIV-1 in human subjects, preferably for use in the treatment or prevention of acquired immune deficiency syndrome (AIDS) in human subjects.

In one other aspect, the present invention is also directed to a method of treatment of a patient suffering from a disease caused by the human immunodeficiency virus HIV-1 in human subjects, preferably for use in the treatment or prevention of acquired immune deficiency syndrome (AIDS) in human subjects, wherein the patient is administered an effective amount of the monoclonal human antibody or binding fragment thereof according to the invention or a pharmaceutical composition of the invention.

In another aspect, the present invention is also directed to the use of the monoclonal human antibody or binding fragment thereof according to the invention or a pharmaceutical composition of the invention in the manufacture of a medicament for treatment of a disease caused by the human immunodeficiency virus HIV-1 in human subjects, preferably for treatment or prevention of acquired immune deficiency syndrome (AIDS) in human subjects.

All embodiments of the present invention as described herein are deemed to be combinable in any combination, unless the skilled person considers such a combination to not make any technical sense.

EXAMPLES

A) Experimental Methods

Isolation of Monoclonal Antibody Sequences

Blood and leukapheresis samples were obtained under protocols approved by the Institutional Review Board of the University of Cologne (protocols 13-364 and 16-054) and the participant provided written informed consent. Peripheral blood mononuclear cells (PBMCs) were isolated by density-gradient centrifugation and stored at −150° C. in 90% FBS and 10% DMSO. B cells were isolated from PBMCs by magnetic cell separation and labeled with anti-human CD19-AF700, anti-human IgG-APC, DAPI (BD), and an HIV-1 Env bait protein for 30 minutes on ice. The HIV-1 Env bait protein was either BG505$_{SOSIP.664}$-GFP (Sliepen et al., 2015) or biotinylated (EZ-Link Sulfo NHS Bioting and Labeling Kit, Thermo Fisher) YU2$_{gp140}$ (Yang et al., 2000) that was labeled with Streptavidin-PE. Env-reactive CD19$^+$IgG$^+$DAPI$^-$ single cells were sorted as described before (Ehrhardt et al., 2019). Sorted cells were incubated with random hexamer primer, NP-40, and RNase-free H$_2$O for 1 min at 65° C. Subsequently, cDNA was generated using SuperScript IV in the presence of RT Buffer, dNTPs, DTT, H$_2$O, RNasin, and RNaseOUT. Antibody sequences for single cell analysis were amplified by semi-nested PCRs using Taq polymerase and the previously described primers CG_RT (Ozawa et al., 2006, first PCR), IgG_Internal RT (Tiller et al., 2008, second PCR), and the OPT5/oPR-primer mix (Kreer et al., 2019, both PCRs)

Antibody Sequence Analysis

Sequences of 2nd PCR products with a mean Phred score ≥28 and a minimal length of 240 nucleotides were annotated with IgBLAST (Ye et al., 2013) and trimmed from framework region (FWR) 1 of the variable region to the end of the J gene. Base calls with a Phred score <16 were masked and sequences with >15 masked nucleotides, frameshifts, or stop codons were excluded from further analyses. To analyze the sequences for potential clonalities, all productive heavy chain sequences were grouped by identical V genes and the pairwise Levenshtein distance of their CDRH3s was determined. Individual sequences were grouped into clones when they shared the same V gene and had a minimal CDRH3 identity of 75%. After 10 rounds with a randomized input of sequences the result that yielded the lowest number of unassigned (non-clonal) sequences was selected for further analyses. All clones were re-validated manually by the investigators in order to identify shared mutations. Sequences that were initially assigned to different clones but shared the same VDJ genes and amino acid and/or silent nucleotide mutations were subsequently grouped into subclones. Nucleotide sequence identity to germline was calculated using IgBLAST.

Monoclonal Antibody Production

For cloning of single cell-derived antibodies, the 1st PCR product of single cell-PCR was used as template and amplified using Q5 High Fidelity Polymerase and specific forward- and reverse primers that resembled the respective nucleotide sequence of the V- and J-regions (Tiller et al., 2008) with expression vector overhangs for subsequent sequence and ligation independent cloning (SLIC). PCR products were cloned into human antibody expression vectors (IgG1, kappa, or lambda chain) by SLIC assembly as previously described (von Boehmer et al., 2016). Antibodies were produced in HEK293-6E cells by transfection using polyethylenimine. After 5-7 days, antibodies were purified from supernatants after protein G incubation and subsequent elution from chromatography columns using 0.1 M glycine (pH=3.0). After buffer neutralization, buffer exchange to PBS, and filter-sterilization, antibodies were stored at 4° C.

Pseudovirus Production

Pseudoviruses were produced in HEK293T cells by co-transfection with pSG3ΔEnv plasmid as described previously (Doria-Rose et al., 2017; Sarzotti-Kelsoe et al., 2014; Hraber et al., 2017; Seaman et al., 2010). To generate the YU2 pseudovirus mutant panel, point mutations were introduced into the plasmid encoding for the YU2 envelope gene using site-directed mutagenesis.

TZM-bl Cell Neutralization Assay

Neutralization assays were performed as previously described (Sarzotti-Kelsoe et al., 2014; Seaman et al., 2010). Murine leukemia virus (MuLV)-pseudotyped virus was used to determine unspecific activity. Antibodies were tested in duplicates. For assays of pseudovirus mutants and of the global reference panel, bioluminescence was determined after adding a luciferin/lysis-buffer (10 mM MgCl2, 0.3 mM ATP, 0.5 mM Coenzyme A, 17 mM IGEPAL (all Sigma-Aldrich), and 1 mM D-Luciferin (GoldBio) in Tris-HCL).

HIV-1-Infected Humanized Mice

Humanized mice were generated as previously described (Klein et al., 2012) with modifications. NOD.Cg-Rag1$^{tm1mom}$||2rg$^{tm1Wjl}$/SzJ (NRG) mice were humanized within five days of birth and 3-6 hours after sublethal irradiation by intrahepatic injection of human CD34$^+$ hematopoietic cord blood and/or placental tissue stem cells. Humanized mice were infected by intraperitoneal challenge using replication-competent recombinant HIV-1$_{YU2}$ (YU2 env in NL4-3 backbone (Zhang et al., 2002)) or HIV-1$_{BAL}$ (BAL env in NL4-3 backbone) that was harvested from supernatants of transfected HEK293T cells.

HIV-1 Viral Load Measurements

Plasma RNA was extracted from EDTA plasma samples using the MinElute Virus Mini Spin Kit including an on-column DNase I digestion step. Viral loads were determined by quantitative real-time PCR using pol-specific primers described previously (Horwitz et al., 2013). qPCR was performed on a LightCycler 480 II using the Taqman RNA-to-Ct 1-Step-Kit. Viral loads were quantified by including a standard curve derived from a sample of known copy number with every qPCR run. The limit of accuracy of the qPCR was determined as 384 copies/ml. Log$_{10}$ changes for viral loads <384 copies/ml were calculated assuming a copy number of 383 copies/ml.

Antibody Treatment of HIV-1-Infected Humanized Mice

Antibodies diluted in PBS were injected subcutaneously. Following a 1 mg loading dose, doses of 0.5 mg were injected every 3-4 days.

Single Genome Sequencing of HIV-1 in Humanized Mice

To determine the development of potential escape mutations in the HIV-1 env gene during antibody treatment of HIV-1-infected humanized mice, extracted plasma RNA was used to generate cDNA using SuperScript IV and antisense primer YB383 (Horwitz et al., 2017), followed by RNase H incubation. Limiting dilution nested PCR was subsequently performed to amplify single genome env cDNA, using Taq polymerase and primers YB383 and YB50 for the first PCR, and primers YB49 and YB52 for the second PCR (Schoofs et al., 2019). Positive PCR reactions at a dilution of <30% PCR efficiency were sequences using illumina dye sequencing as previously described with modifications (Kryazhim-skiy et al., 2014; Schoofs et al., 2016). After tagmentation, addition of indices and adapters by limited cycle PCR, and purification, PCR products were sequenced on an Illumina MiSeq and reads assembled (Gaebler et al., 2019). Full-length env sequences with less than 10 ambiguities (<75% nucleotide identity across reads) were analyzed.

ELISA to Determine Competition for HIV-1 Env Binding

Antibodies 1-18, 1-55 and 2-12 were biotinylated using the EZ Link Sulfo NHS Biotin and Labeling Kit (Thermo Fisher) according to the manufacturer's instructions, followed by a buffer exchange to PBS. High-binding ELISA plates were coated with an anti-6× His tag antibody at 2 µg/ml overnight at 4° C. Wells were blocked with 3% BSA in PBS for 60 min at 37° C., and incubated with BG505$_{SOSIP.664}$-His (Sanders et al., 2013) at 2 µg/ml in PBS for 60 min at 37° C. Competing antibodies were incubated in 1:3 dilutions starting at a concentration of 32 µg/ml in PBS for 60 min at room temperature. Biotinylated antibodies of interest were diluted to 0.5 µg/ml in 3% BSA in PBS and incubated for 60 min at RT, followed by peroxidase-streptavidin diluted 1:5,000 in 1% BSA/0.05% Tween 20 in PBS. Absorbance at 415 nm was determined on a microplate reader after addition of ABTS solution. Plates were washed with 0.05% Tween 20 in PBS between each step.

In Vivo Antibody Pharmacokinetic Analysis

NRG mice were intravenously injected with 0.5 mg of antibody in 200 µl PBS. Total serum concentrations of human IgG were determined by ELISA as previously described with minor modifications (Klein et al., 2012). In brief, high-binding ELISA plates were coated with anti-human IgG at a concentration of 2.5 µg/ml overnight at RT. Subsequently, wells were blocked with blocking buffer (2% BSA, 1 µM EDTA, and 0.1% Tween 20 in PBS). Serial dilutions of a human IgG1 kappa standard (in duplicates) and serum samples in PBS were incubated for 90 min at RT, followed by HRP-conjugated anti-human IgG diluted 1:1,000 in blocking buffer for 90 min at RT. Following the addition of ABTS, optical density at 415 nm was determined using a microplate reader. Plates were washed with 0.05% Tween 20 in PBS between each step. Serum samples obtained before the antibody injection were used to confirm baseline absence of human serum IgG.

B) Specific Examples of Antibodies of the Invention

Example I—Isolation of Broad and Potent VH1-46 Derived HIV-1-Neutralizing Antibodies from an HIV-1-Infected Elite Neutralizer Human B cells reactive to the HIV-1 envelope protein were isolated from an HIV-1-infected individual who was previously identified as having exceptional serum neutralizing activity against HIV-1 in in vitro assays.

To this end, isolated B cells were incubated with fluoro-chrome-labeled soluble HIV-1 Env protein (YU2$_{gp140}$ or BG505$_{SOSIP.664}$) and single-cell sorted (Ehrhardt et al., 2019). This approach enabled the subsequent amplification of heavy and light antibody gene segments from an individual HIV-1 Env-reactive B cell by PCR. This allowed for the cloning of the PCR products into expression vectors for the recombinant production of the corresponding antibody encoded by an individual B cell, enabling functional testing of the antibody.

From the analysis of the sequences of HIV-1-Env reactive B cells, expanded VH1-46-derived B cell clones could be identified. One of these clones was characterized by a six amino acid (aa) insertion into heavy chain CDR1 region, and this clone is represented by consensus sequences for the heavy chain (SEQ ID: 47) and light chain (SEQ ID: 48). Three additional B cell clones were identified that share similarities among each other and to the previously described clone. These additional clones do not carry a 6 aa CDRH1 insertion, but show a 2 aa deletion in the framework region 1 of their light chain. These clones are represented by separate consensus sequences for the heavy chain (SEQ ID: 49) and light chain (SEQ ID: 50).

A total of 23 antibodies representative of the identified VH1-46-derived B cell clones were produced as monoclonal antibodies. To determine their overall neutralizing potency and breadth, these antibodies were tested for their neutralizing activity in the TZM-bl cell neutralization assay against a reference panel of 12 HIV-1 pseudovirus strains that is referred to as "global panel" (FIG. 1). This panel of pseudoviruses was previously designed to be a representation of the diversity of the global HIV-1 epidemic and enable a standardized assessment of the activity of neutralizing antibodies.

Notably, all of the isolated VH1-46-derived antibodies demonstrated high neutralizing activity against at least 11 out 12 of the HIV-1 reference strains (FIG. 1). VH1-46-derived antibodies represented by SEQ IDs 47 and 48 demonstrated activity against all of the tested strains. In addition to their neutralizing breadth, the tested VH1-46-derived antibodies also demonstrated high neutralizing potency. The neutralizing potency is routinely represented by the 50% inhibitory concentration (IC$_{50}$). When tested against the "global panel", all tested VH1-46-derived antibodies were highly active with geometric mean IC$_{50s}$ of 0.2 µg/ml or less against the neutralized virus strains (FIG. 1).

Example II—Identification of the CD4 Binding Site as Target of Antibodies of the Invention To determine the epitope of antibodies according to the invention, the binding of representative antibodies 1-18, 1-55, and 2-12 to the HIV-1 Envelope trimer of BG505$_{SOSIP.664}$ in the presence of antibodies of known specificity was studied. Interference with the CD4 binding site antibodies 3BNC117, N6, and VRC01 was detected (FIG. 2). This indicates that the antibodies of the invention target the CD4 binding site and an epitope that overlaps with that of other antibodies binding to the CD4 binding site.

Example III—High Potency and Breadth of Antibodies 1-18, 1-55, and 2-12

To confirm the neutralizing potency and breath of the isolated VH1-46-derived HIV-1 antibodies, the representative antibodies 1-18, 1-55 and 2-12 were individually tested against an extended panel of 119 HIV-1 pseudoviruses as previously tested in Schoofs et al., 2019. This panel of pseudoviruses represents a development of a panel of pseudoviruses described in detail in Seaman et al., 2010. It provides a representation of the genetic and global diversity of HIV-1 Env variants. It includes HIV-1 variants of different clades or subtypes, including variants isolated from transmitted/founder viruses and difficult-to-neutralize viruses.

Notably, the tested VH1-46-derived antibodies of the invention demonstrated high neutralizing potency and breadth when tested on the 119-pseudovirus multiclade panel (FIG. 3). In particular, when tested at antibody concentrations up to 20 µg/ml, antibody 1-18 neutralized 96.6% of the tested pseudoviruses and showed a geometric mean IC$_{50}$ of 0.048 µg/ml against the neutralized pseudoviruses (FIG. 3). This breadth and potency are higher than seen for other HIV-1 neutralizing antibodies that also target the CD4 binding site, are derived from the VH1-2-gene segment, and are in advanced stages of clinical testing (3BNC117 and VRC01) (FIG. 3). Moreover, the potency of antibody 1-18 in the 119-multiclade panel was higher than that of N6, another VH1-2-derived CD4 binding site antibody in clinical testing (FIG. 3).

Figure 4:
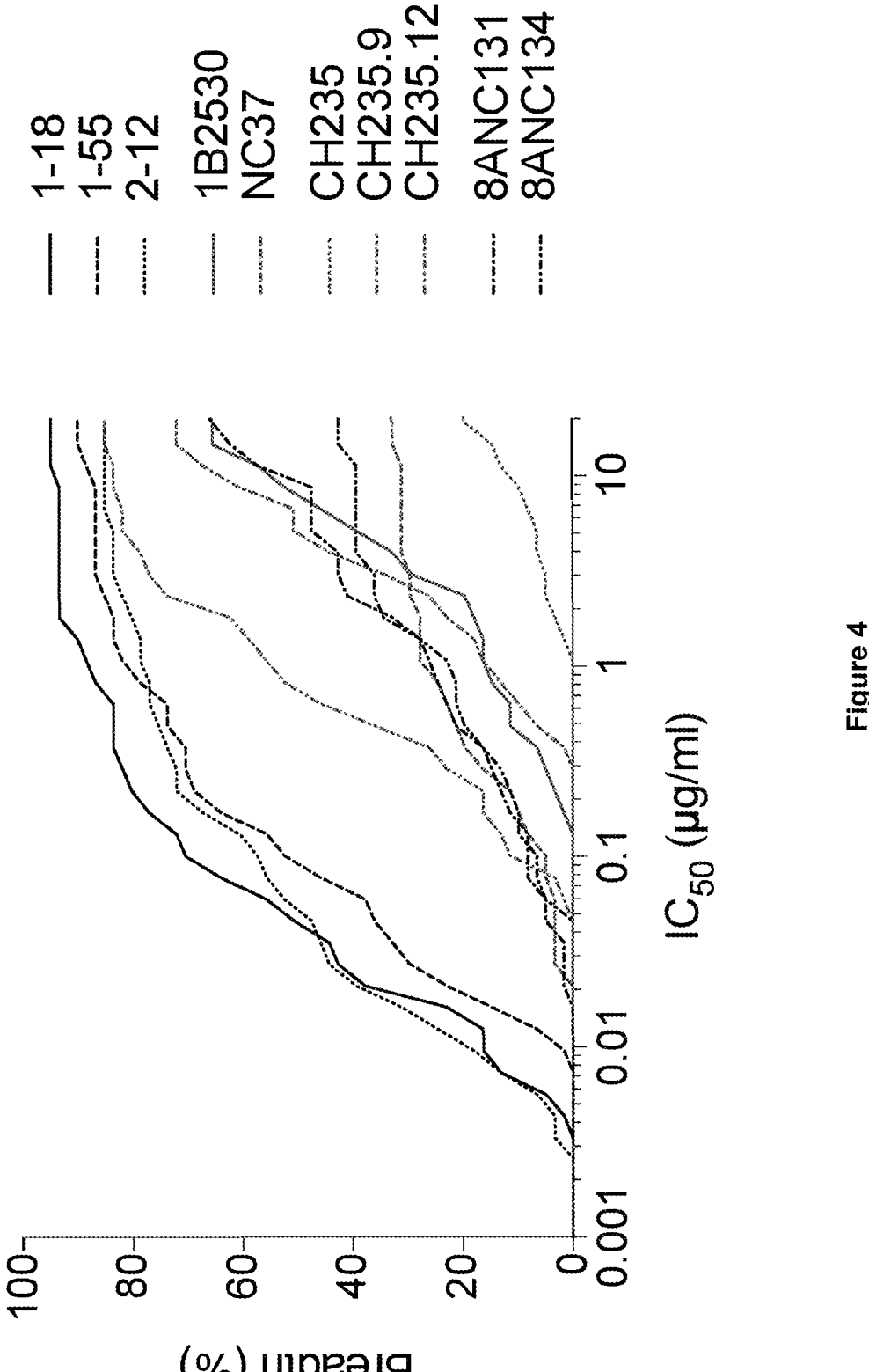
FIG. 4 shows the neutralizing activity of antibodies 1-18, 1-55, 2-12 compared to other VH1-46-derived HIV-1 neutralizing antibodies, for which results against a panel of a total of 62 HIV-1 pseudoviruses was available at the antibody neutralization database CATNAP (Yoon et al., 2015).

In addition, when compared to other VH1-46-derived HIV-1 neutralizing antibodies targeting the CD4 binding site, for which results against a total of 62 identical HIV-1 pseudovirus was available (Yoon et al., 2015), the representative VH1-46-derived antibodies of the invention demonstrated higher potency and breadth (FIG. 4).

Example IV—Neutralizing Activity Against Pseudoviruses That are Poorly Neutralized by Other CD4 Binding Site Antibodies Although CD4 binding site antibodies can achieve high levels of neutralizing breadth (i.e., have activity against a large number of different HIV-1 Env variants), antibody-resistant HIV-1 variants exist. Thus, it important to identify novel CD4 binding site antibodies that are highly active against such HIV-1 variants.

Compared to CD4 binding site antibodies in advanced stages of clinical testing (N6, 3BNC117, VRC01), antibodies of this invention neutralize several strains with much higher potency (i.e., they have lower $IC_{50}s$) (representative members 1-18, 1-55 and 2-12 are shown in FIG. 5).

For example, the pseudovirus comprising the HIV-1 Env protein of virus strain 89-F1_2_25 is not neutralized by the CD4 binding site antibodies in clinical testing (N6, 3BNC117, VRC01) when tested at concentrations up to 20 µg/ml in the TZM-bl pseudovirus neutralization assay (i.e., these antibodies do not reach an $IC_{50}$ against this particular virus) (FIG. 5). Moreover, of 30 CD4 binding site IgG antibodies listed within the neutralizing antibody database CATNAP (Yoon et al., 2015), 89.7% (26/29) antibodies do not neutralize this virus at all (i.e., $IC_{50}>20$ µg/ml). Of the three antibodies that neutralize this virus, NC37 has an $IC_{50}$ of 17.7 µg/ml, $VRC_{16}$ has an IC50 of 3.12 µg/ml, and the VH1-69 gene-derived antibody VRC13 has an $C_{50}$ of 0.19 µg/ml. In contrast, the representative antibodies of the invention (1-18, 1-55, and 2-12) neutralize HIV-1 pseudovirus 89-F1_2_25 with very high potency ($IC_{50}s$ of 0.007, 0.014, and 0.006 µg/ml, respectively) as do all other antibodies of the invention ($IC_{50}s$ between 0.006 and 0.025 µg/ml across all antibodies, see FIG. 12). Another viral strain that is highly resistant to common CD4 binding site antibodies is the strain 6545.v4.c1. This strain is resistant to 75% of the 43 CD4 binding site IgG antibodies listed within the neutralizing antibody database CATNAP (Yoon et al., 2015). Most importantly, none of the CD4 binding site antibodies that are in advanced stages is able to potently ($IC_{50}<10$ u/ml) neutralize this strain ($IC_{50}$ of N6: 16.23; 3BNC117: >20; VRC01: >20; VRC07-523-LS: >20). In contrast, all antibodies of this invention potently neutralize this strain with $IC_{50}s$ between 0.008 and 9.37 µg/ml (FIG. 12).

Thus, antibodies of this invention provide a solution to the poor neutralization of viruses 89-F1_2_25 and 6545.v4.c1 through CD4 binding site antibodies. When tested against 89-F1_2_25, the antibodies of this invention are about 1 $log_{10}$ more potent than the best CD4 binding site antibody against this virus described before.

Example V-Neutralizing Activity Against Pseudoviruses With CD4 Binding Site Mutations That Confer Resistance to Other CD4 Binding Site Antibodies Antibody resistance mediated by the development of CD4 binding site escape mutations results in treatment failure of antibody therapy of HIV-1 infection (Klein et al, 2012). Thus, it is critical to identify CD4 binding site antibodies that are not affected by these escape mutations to provide a treatment option for HIV-1 variants carrying these mutations.

CD4 binding site antibodies were tested in the TZM-bl cell neutralization assay against a panel of YU2 pseudovirus variants with specific CD4 binding site mutations (FIG. 6). Mutations in the CD4 binding site affected the activity of previously known CD4 binding site antibodies (FIG. 6). For example, the $IC_{50}$ of the CD4 binding site antibodies VRC01 and 8ANC131 against wild type YU2 pseudovirus was 0.107 µg/ml and 0.256 µg/ml, respectively, but no neutralization was observed against any of the tested loop D mutant variants (i.e., no $IC_{50}$ at up to the tested antibody concentration of 2.5 µg/ml). N6, another CD4 binding site antibody, was affected by mutation N279K (FIG. 6). In contrast, the tested representative antibodies of the invention (1-18, 1-55, and 2-12) maintained high neutralizing activity against the tested YU2 pseudovirus variants (FIG. 6).

Thus, the of this invention provide a solution to the resistance of CD4 binding site antibodies against virus variants with mutations in the CD4 binding site.

Example VI—Maintaining Viral Suppression by Antibody Monotherapy in an In Vivo Model of HIV-1-Infection Humanized mice infected with HIV-1$_{YU2}$ (Zhang et al., 2002) provide a model to study the antiviral activity of neutralizing HIV-1 antibodies in vivo. To generate humanized mice, immunodeficient NRG mice are irradiated within the first days after birth and injected intrahepatically with human hematopoietic $CD34^+$ stem cells. This results in the development of human lymphocytes that can be infected with replication-competent HIV-1. These mice can maintain stable levels of viremia (i.e., HIV-1 RNA copy numbers in plasma) and show a rate of HIV-1 sequence diversification that is similar to what is observed in humans (Klein et al., 2012). This mouse model has previously been used to determine the antiviral activity of several CD4 binding site antibodies given as monotherapy in vivo (179NC75: Freund et al., 2015; 3BNC117: Horwitz et al, 2013; 45-46$^{G54W}$: Klein et al, 2012; NC37: Freund et al., 2017). In all of these studies, only transient effects on the viral load were observed and viral rebound (i.e., return of viremia towards baseline levels) rapidly developed. Moreover, this viral rebound was associated with the development of mutations in the antibody target sites. Thus, novel CD4 binding site antibodies are required that are capable of maintaining viral suppression when given as monotherapy.

Figure 7:
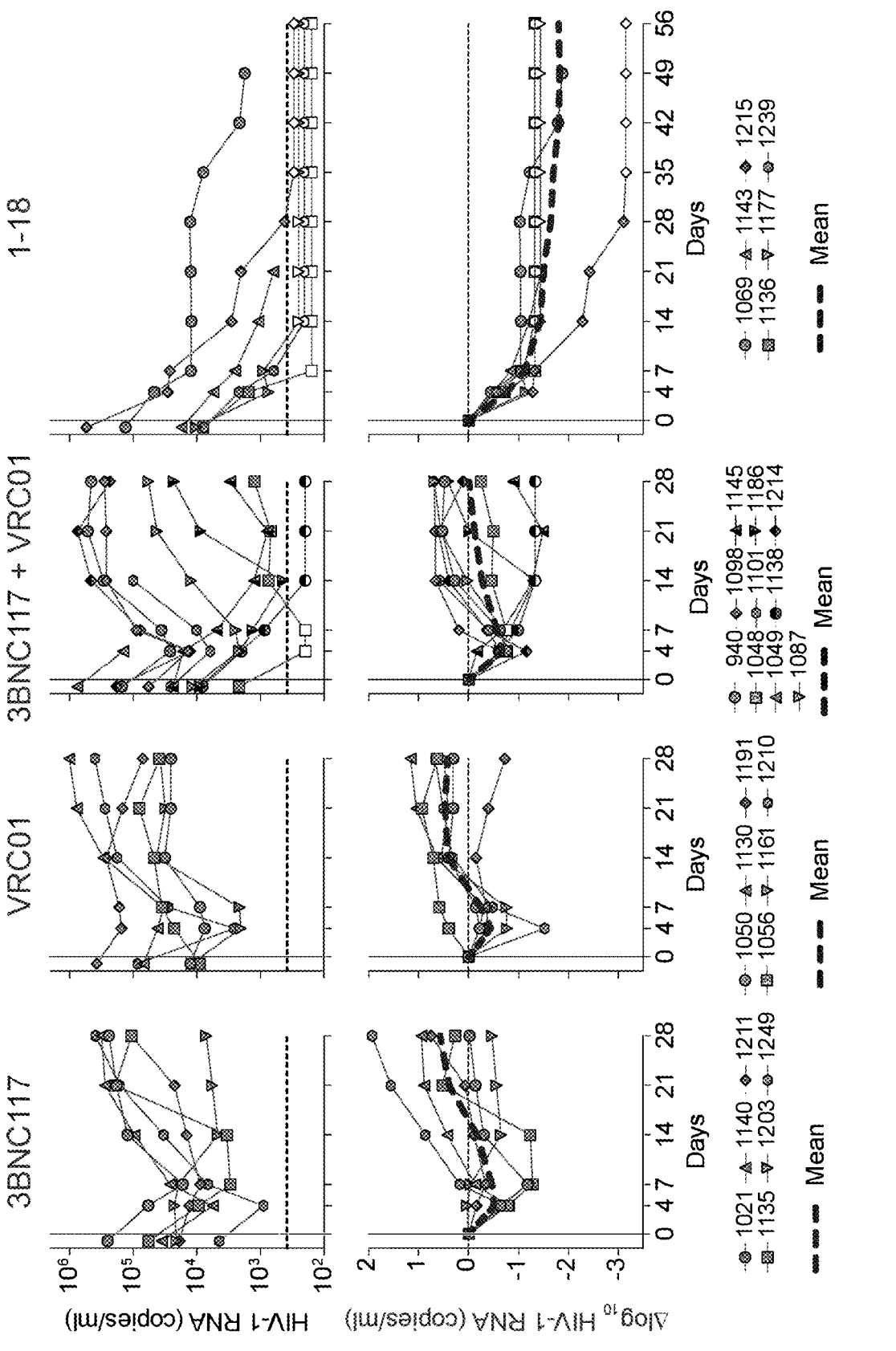
FIG. 7 shows HIV-1 RNA plasma copy numbers (top) and their log$_{10}$ change (bottom, compared to baseline (HIV-1 RNA plasma copy number of day −1)) in humanized mice infected with HIV-1$_{YU2}$ (NL4-3 virus with envelope gene substituted for that of YU2). Mice were treated subcutaneously with a 1 mg loading dose per antibody, followed by subcutaneous injections of 0.5 mg per antibody every 3-4 days. Mice treated with the known CD4bs antibodies 3BNC117, VRC01, or the combination of both antibodies show a transient reduction of viremia, followed by rapid viral rebound. In contrast, mice treated with antibody 1-18 of the invention alone show a persistent reduction of viremia throughout the treatment period of 8 weeks. Dashed black lines indicate mean log$_{10}$ change.

When HIV-1$_{YU2}$-infected humanized mice were treated with the CD4 binding site antibodies 3BNC117, VRC01, or the combination of thereof (1 mg loading dose per antibody subcutaneously (s.c.), followed by 0.5 mg given s.c. every 3-4 days), only a transient reduction of the HIV-1 RNA copy number was observed, and viremia returned to baseline levels in most mice within 2-3 weeks (FIG. 7). In contrast, when mice were treated according to the same dosing scheme with the representative antibody 1-18 of the invention, viral suppression compared to the viral copy number at the start of treatment was observed in all treated mice for a period of eight weeks of treatment (FIG. 7). In ≥80% of mice, the HIV-1 RNA plasma copy number was reduced to levels below the limit of accuracy of the used assay (384 copies/ml).

Thus, antibodies of this invention are capable to effectively maintain viral suppression in HIV-1$_{YU2}$-infected humanized mice even when given as monotherapy.

Figure 13:
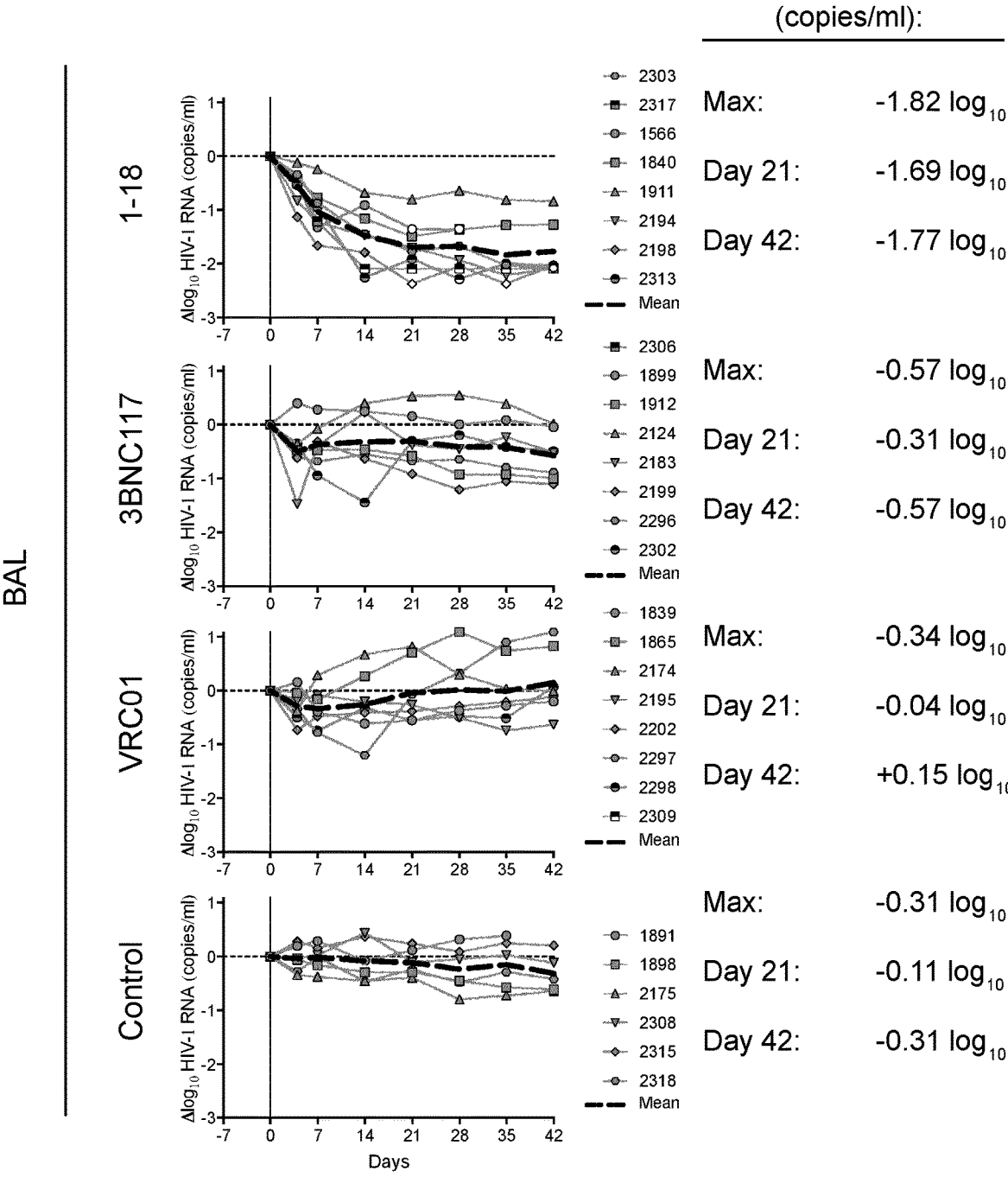
FIG. 13 shows the HIV-1 RNA plasma copy numbers $log_{10}$ change in humanized mice infected with HIV-1$_{BAL}$ (NL4-3 virus with envelope gene substituted for that of the HIV-1 strain BAL) compared to baseline (day 0). Mice were treated subcutaneously with a 1 mg loading dose per antibody, followed by subcutaneous injections of 0.5 mg per antibody every 3-4 days. Mice treated with the CD4 binding site antibodies 3BNC117 or VRC01 show a modest transient reduction of viremia followed by rapid viral rebound. In contrast, mice treated with antibody 1-18 of the invention show a persistent reduction of viremia throughout the treatment period of 6 weeks. Control mice were untreated. Striped black lines indicate the mean $log_{10}$ change compared to baseline. Numbers indicate individual mice by their respective ID. The table on the right indicates the maximum mean $log_{10}$ HIV-1 RNA change, the day 21 $log_{10}$ HIV-1 RNA change, and the day 42 $log_{10}$ HIV-1 RNA change observed for each treatment cohort.

Moreover, when HIV-1$_{BAL}$-infected humanized mice were treated with the CD4 binding site antibodies 3BNC117 or VRC01 as described above, only a minor and transient reduction of the HIV-1 RNA copy number was observed, and viremia returned to baseline levels in most mice within 2 weeks (FIG. 13). In contrast, when mice were treated according to the same dosing scheme with the representative antibody 1-18 of the invention, viral suppression compared to the viral copy number at the start of treatment was observed in all treated mice for a period of six weeks of treatment (FIG. 13).

Thus, antibodies of this invention are capable to effectively maintain viral suppression in HIV-1$_{BAL}$-infected humanized mice even when given as monotherapy.

Example VII—Preventing the Development of Viral Mutation in the CD4 Binding Site During Antibody Monotherapy Viral rebound during antibody monotherapy with CD4 binding site antibodies is typically associated with the development of virus sequence mutations in the antibody target sites (179NC75: Freund et al., 2015; 3BNC117: Horwitz et al, 2013; 45-46$^{G54W}$: Klein et al, 2012; NC37: Freund et al., 2017). Thus, novel CD4 binding site antibodies that can prevent the development of mutations in the CD4 binding site antibodies are required to prevent antibody resistance mediated by such mutations.

Figure 8:
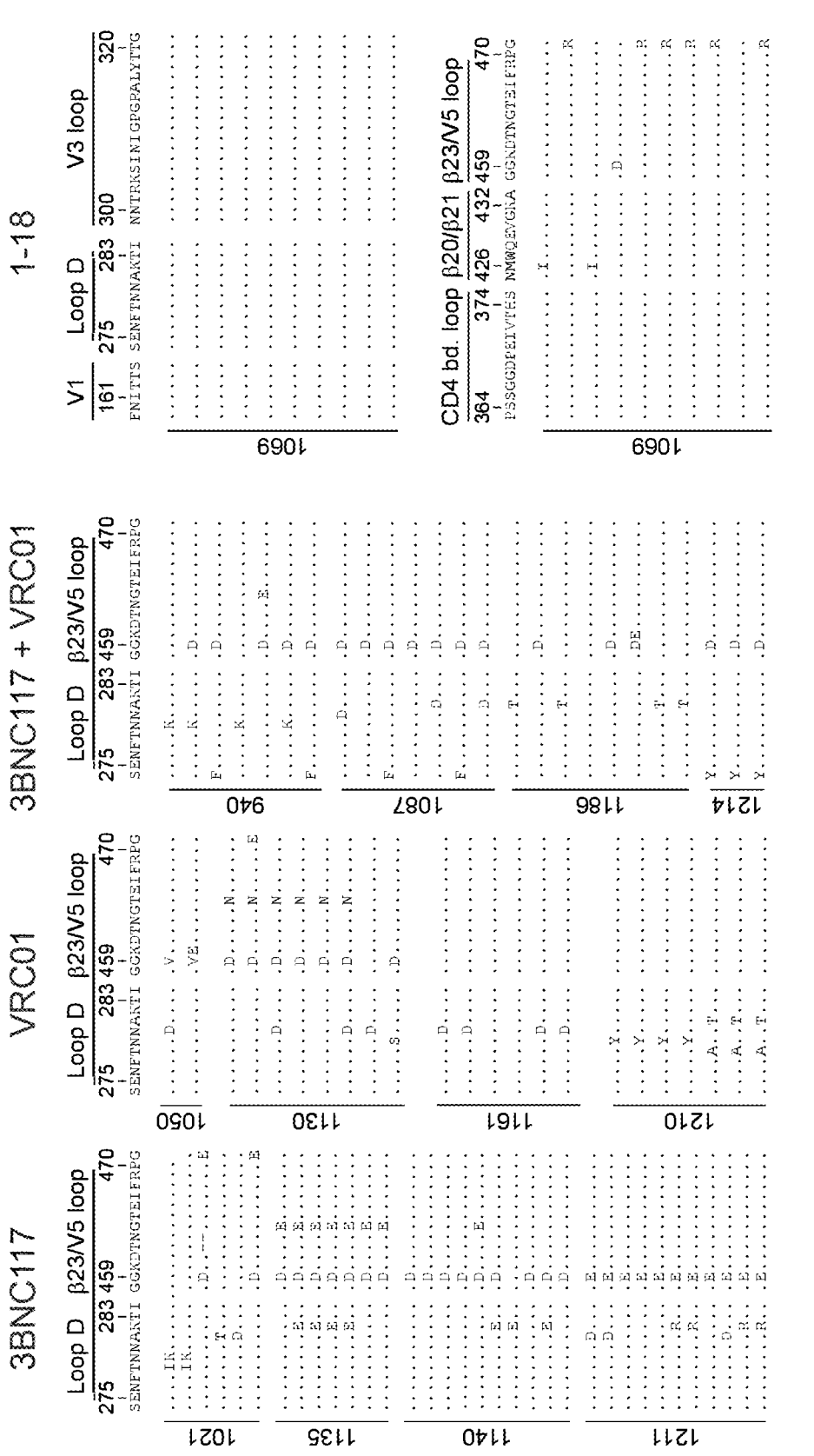
FIG. 8 shows HIV-1 sequences obtained from plasma by single-genome sequencing of selected mice depicted in FIG. 7 after 4 weeks of antibody therapy. Mouse IDs corresponding to FIG. 7 are depicted on the left. Sequences are aligned to the YU2 wild type sequence shown at the top. Amino acid sequence agreements to the YU2 wild type sequence are indicated by dots, mutations or deletions compared to the YU2 wild type sequence are indicated by the amino acid one-letter codes or dashes, respectively. In mice treated with the known CD4bs antibodies 3BNC117, VRC01, or the combination thereof, mutations in the CD4 binding site epitope (loop D, beta23 strand, V5 loop) compared to YU2 wild type sequence were associated with viral rebound, whereas no such mutations were observed after four weeks of therapy with antibody 1-18 of the invention alone.

Mutations in the CD4 binding site (loop D, beta23 strand/V5 loop) were observed in all tested mice receiving 3BNC117, VRC01, or 3BNC117+VRC01 therapy as described in Example IV (FIG. 8). In contrast, a mutation in these sites was found in only one of out of ten sequences in the mouse of the experiment described in Example IV that had remaining detectable viremia after four weeks of antibody therapy with antibody 1-18 of the invention (FIG. 7). Notably, when this mutation (G459D) was tested in the YU2 pseudovirus panel, the activity of 1-18 was not affected (FIG. 6).

Example VIII—Maintaining Viral Suppression by Antibody Monotherapy in an In Vivo Model of HIV-1-Infection After Viral Rebound from VRC01-Class Therapy Failure of antibody monotherapy using CD4 binding site antibodies in HIV-1-infected humanized mice results in viral rebound and is associated with viral resistance against the administered antibody (Freund et al., 2015; Horwitz et al, 2013; Klein et al, 2012; Freund et al., 2017). Thus, novel CD4 binding site antibodies are required that provide an in vivo treatment option after previous failure of CD4 binding site therapy.

Figure 9:
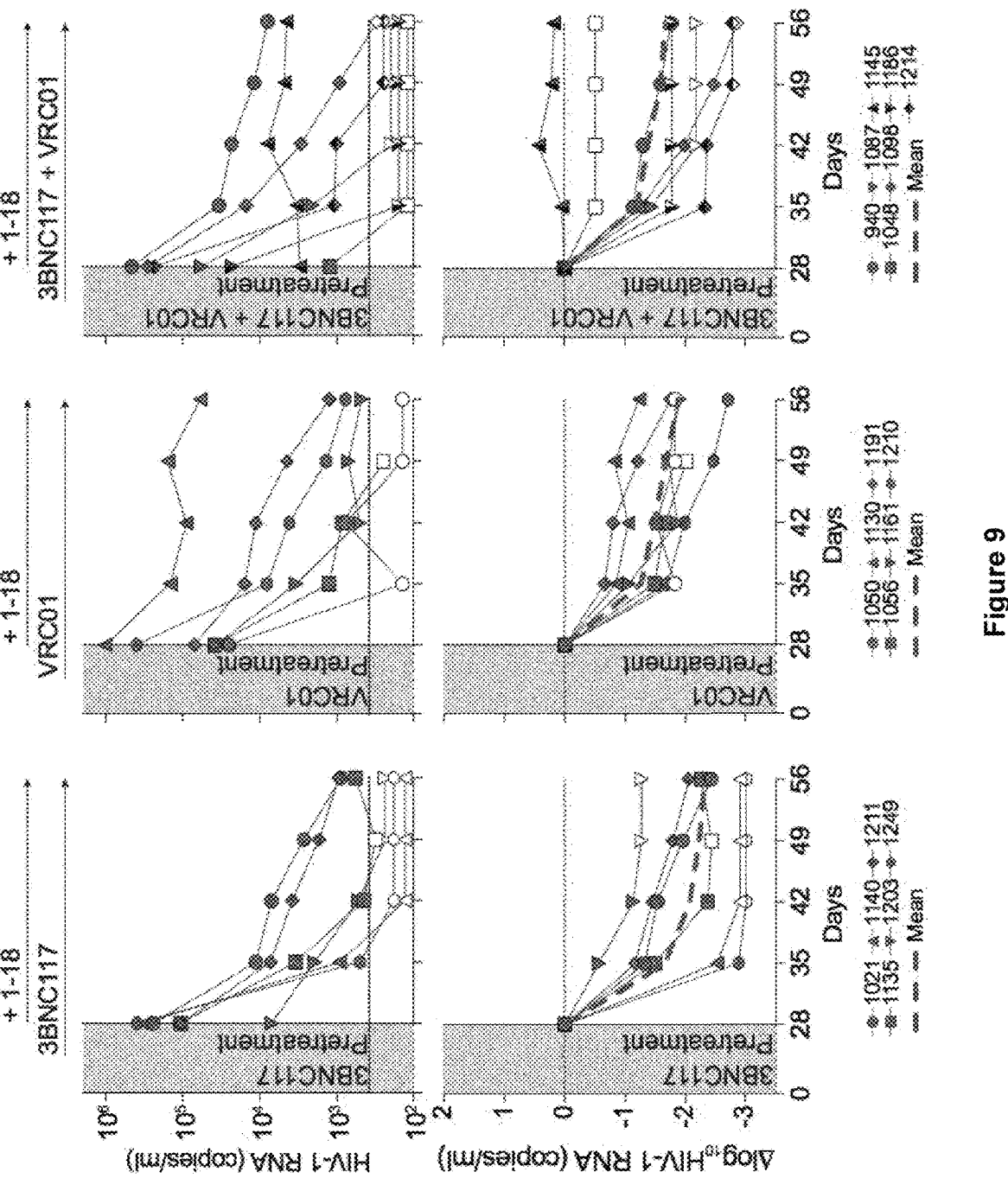
FIG. 9 shows HIV-1 RNA plasma copy numbers (top) and their log$_{10}$ change (bottom, compared to baseline (HIV-1 RNA plasma copy number at day 28)) in humanized mice infected with HIV-1$_{YU2}$ (NL4-3/YU2) that were pre-treated with the CD4 binding site antibodies 3BNC117, VRC01 or the combination of both (as shown in FIG. 7). After four weeks of treatment, antibody 1-18 was added to the previous treatment regimen that was continued throughout. 1-18 was administered subcutaneously with a 1 mg loading dose, followed by 0.5 mg every 3 days to 4 days. Despite viral rebound after pre-treatment with other CD4 binding site antibodies and circulating viral variants with mutations in the CD4 binding site (see FIG. 8), treatment with antibody 1-18 resulted in maintained viral suppression in 18/19 mice.

Following the viral rebound observed during four weeks of treatment with 3BNC117, VRC01, or the combination thereof (as described in Example VI), the addition of antibody 1-18 of the invention to treatment regimen (1 mg loading dose s.c. followed by 0.5 mg given s.c. every 3 days to 4 days) resulted in a sustained reduction of viremia in 95% (18/19) of treated mice (FIG. 9). Thus, antibodies of the invention provides an option for the in vivo control of HIV-1 even after the failure of pretreatment with other CD4 binding site antibodies.

Example IX—Favorable In Vivo Half-Life Compared to Other CD4 Binding Site Antibodies HIV-1 neutralizing antibodies can vary not only in their neutralizing potency and breadth, but also in their in vivo half-life. For example, the V3 loop-targeting antibody 10-1074 has a longer half-life than the CD4 binding site antibody 3BNC117 when given to HIV-1-infected individuals (Mendoza et al., 2018). Thus, novel antibodies targeting the CD4 binding site should have favorable pharmacokinetic properties in vivo compared to those CD4 binding site antibodies currently available.

Figure 10:
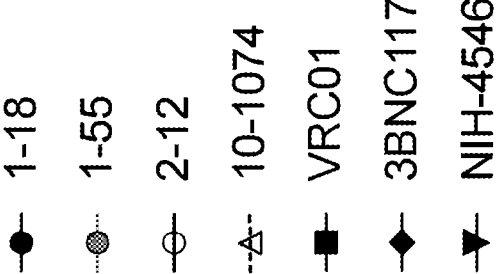
FIG. 10 shows the serum concentration of human IgG as determined by ELISA in NRG mice after a single intravenous injection of 0.5 mg of antibody on day 0 (indicated by arrow). Compared to the known CD4 binding site antibodies 3BNC117, VRC01, and 45-46$^{G54W}$, the antibodies 1-18, 1-55, and 2-12 of the invention show a slower decline of antibody concentrations, which is more similar to the V3 loop targeting antibody 10-1074 that has a longer half-life than 3BNC117 in humans (Mendoza et al., 2018).
Figure 10:
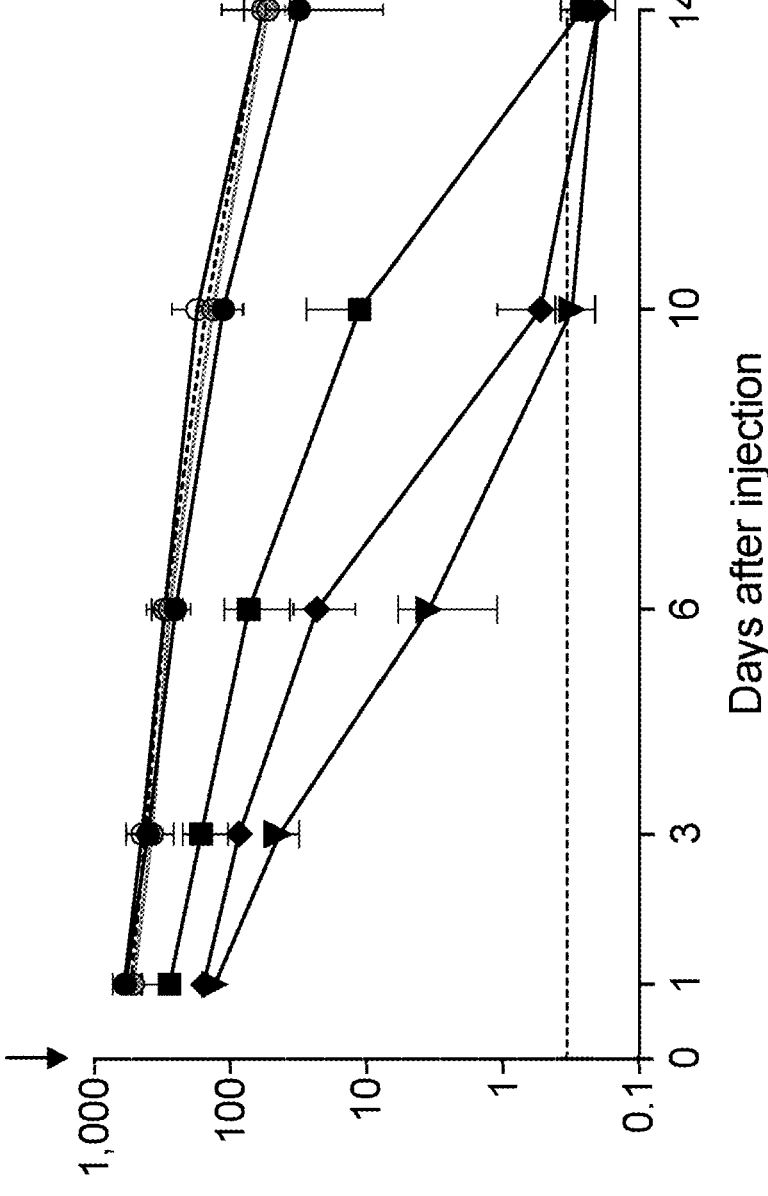
Figure 11:
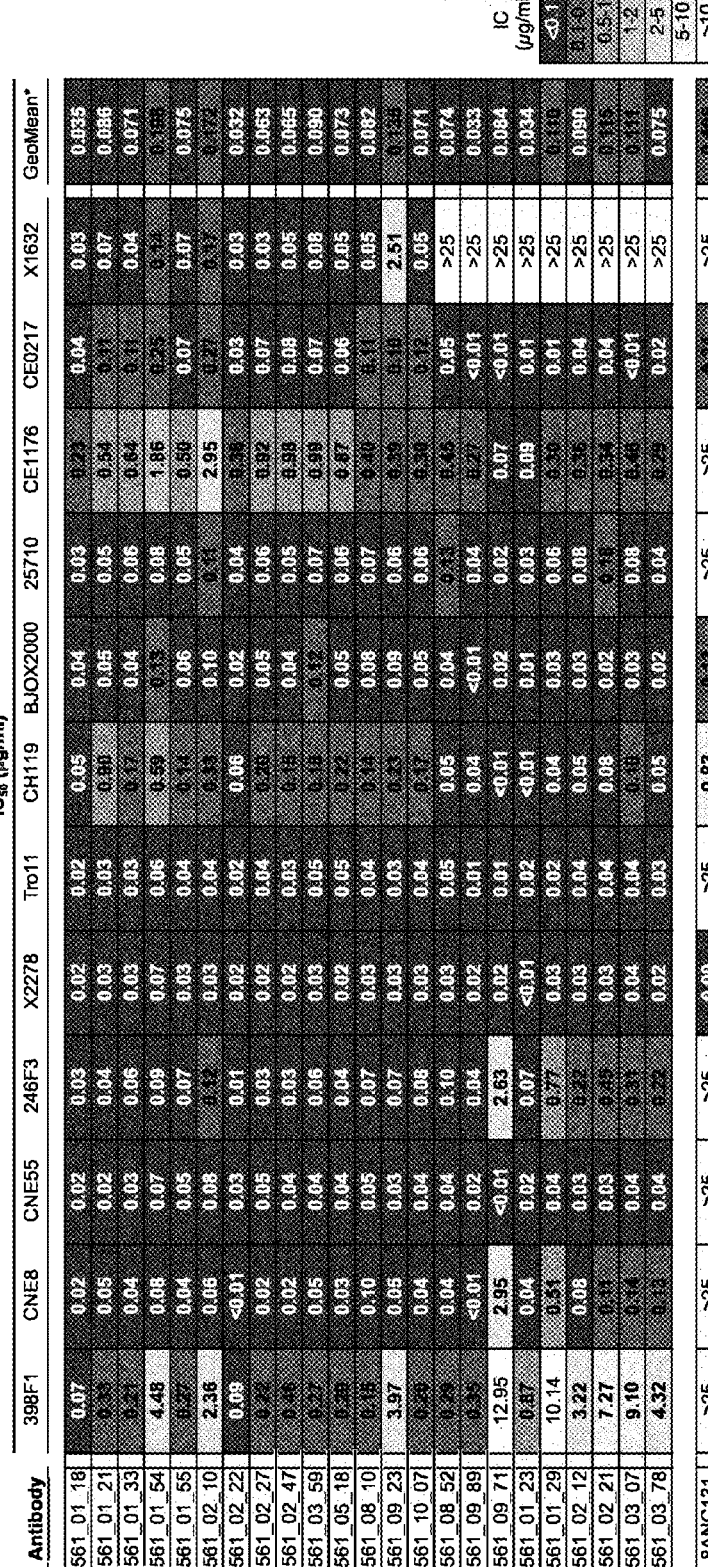
FIG. 11 shows the neutralizing activity (IC$_{50}$) of antibodies against a selection of pseudoviruses with different envelope amino acid sequences as determined in the TZM-bl cell pseudovirus assay. The pseudovirus panel was selected to be representative of the diversity of the global HIV-1 pandemic (de Camp et al., 2014). Antibodies of the invention are compared to the VH1-46 derived CD4 binding site antibody 8ANC131.

To determine their pharmacokinetic properties, representative antibodies of the invention (1-18, 1-55, and 2-12) were individually injected intravenously into NRG mice. Compared to the CD4 binding site antibodies 3BNC117, VRC01, and 45-46$^{G54W}$, the tested antibodies of the inventions showed a slower decline of their serum IgG concentration as determined by total human IgG ELISA that was more similar to that of 10-1074 (FIG. 10). Thus, the tested antibodies of the invention demonstrate favorable pharmacokinetic properties compared to other CD4 binding site antibodies targeting HIV-1.

REFERENCES FOR EXAMPLES SECTION

Anderson, J. P., et al. (2000). Testing the hypothesis of a recombinant origin of human immunodeficiency virus type 1 subtype E. J. Virol. 74, 10752-10765.

deCamp, A., et al. (2014). Global Panel of HIV-1 Env Reference Strains for Standardized Assessments of Vaccine-Elicited Neutralizing Antibodies. J, Virol. 88, 2489-2507.

Doria-Rose, N. A., et al. (2017). Mapping Polyclonal HIV-1 Antibody Responses via Next-Generation Neutralization Fingerprinting. PLoS Pathog 13, e1006148.

Dosenovic, P., et al. (2019). Anti-idiotypic antibodies elicit anti-HIV-1-specific B cell responses. J. Exp. Med.

Ehrhardt et al., (2019) Polyclonal and convergent antibody response to Ebola virus vaccine rVSV-ZEBOV. Nat Med. 25, 1589-1600.

Freund, N. T., et al. (2015). A New Glycan-Dependent CD4-Binding Site Neutralizing Antibody Exerts Pressure on HIV-1 In Vivo. PLoS Pathog. 11, e1005238.

Freund, N. T., et al. (2017). Coexistence of potent HIV-1 broadly neutralizing antibodies and antibody-sensitive viruses in a viremic controller. Sci Transl Med. 9, eaal2144

Gaebler, C., et al. (2019). Combination of quadruplex qPCR and next-generation sequencing for qualitative and quantitative analysis of the HIV-1 latent reservoir. J. Exp. Med.

Horwitz, J. A., et al. (2013). HIV-1 suppression and durable control by combining single broadly neutralizing antibodies and antiretroviral drugs in humanized mice. Proc. Natl. Acad. Sci. USA 110, 16538-16543.

Horwitz, J. A., et al. (2017). Non-neutralizing Antibodies Alter the Course of HIV-1 Infection In Vivo. Cell 170, 637-648 e610.

Hraber, P., et al. (2017). Panels of HIV-1 Subtype C Env Reference Strains for Standardized Neutralization Assessments. J. Virol. 91.

Klein, F., et al. (2012). HIV therapy by a combination of broadly neutralizing antibodies in humanized mice. Nature 492, 118-122.

Kreer, C., et al. (2019). openPrimeR for multiplex amplification of highly diverse templates. bioRxiv. https://doi.org/10.1101/847574

Kryazhimskiy, S., et al. (2014). Microbial evolution. Global epistasis makes adaptation predictable despite sequence-level stochasticity. Science 344, 1519-1522.

Mendoza, P., et al. (2018). Combination therapy with anti-HIV-1 antibodies maintains viral suppression. Nature 561, 479-484.

Pietzsch, J., et al. (2010). Human anti-HIV-neutralizing antibodies frequently target a conserved epitope essential for viral fitness. J. Exp. Med. 207, 1995-2002.

Sanders, R. W., et al. (2013). A next-generation cleaved, soluble HIV-1 Env trimer, BG505 SOSIP.664 gp140, expresses multiple epitopes for broadly neutralizing but not non-neutralizing antibodies. PLoS Pathog. 9, e1003618.

Sarzotti-Kelsoe, M., et al. (2014). Optimization and validation of the TZM-bl assay for standardized assessments of neutralizing antibodies against HIV-1. J. Immunol. Methods 409, 131-146.

Schoofs, T., et al. (2016). HIV-1 therapy with monoclonal antibody 3BNC117 elicits host immune responses against HIV-1. Science 352, 997-1001.

Seaman, M. S., et al. (2010). Tiered categorization of a diverse panel of HIV-1 Env pseudoviruses for assessment of neutralizing antibodies. J. Virol. 84, 1439-1452.

Sliepen, K., et al. (2015). Engineering and Characterization of a Fluorescent Native-Like HIV-1 Envelope Glycoprotein Trimer. Biomolecules 5, 2919-2934.

Tiller, T., et al. (2008). Efficient generation of monoclonal antibodies from single human B cells by single cell RT-PCR and expression vector cloning. J. Immunol. Methods 329, 112-124.

von Boehmer, L., et al. (2016). Sequencing and cloning of antigen-specific antibodies from mouse memory B cells. Nat. Protoc. 11, 1908-1923.

Yang, X., et al. (2000). Characterization of stable, soluble trimers containing complete ectodomains of human immunodeficiency virus type 1 envelope glycoproteins. J. Virol. 74, 5716-5725.

Ye, J., et al. (2013). IgBLAST: an immunoglobulin variable domain sequence analysis tool. Nucleic Acids Res. 41, W34-40.

Yoon, H., et al. (2015). CATNAP: a tool to compile, analyze and tally neutralizing antibody panels. Nucleic Acids Res. 43, W213-219.

Zhang, Y. J., et al. (2002). Envelope-dependent, cyclophilin-independent effects of glycosaminoglycans on human immunodeficiency virus type 1 attachment and infection. J. Virol. 76, 6332-6343.

The invention claimed is:

1. A method comprising:
   administering a pharmaceutical composition to a human subject infected with HIV-1, wherein the pharmaceutical composition comprises:
   a recombinant human monoclonal anti-human immunodeficiency virus (HIV) antibody comprising a human heavy chain and a human light chain,
   wherein the human heavy chain comprises a human heavy chain variable domain comprising the amino acid sequence according to SEQ ID NO: 1 recombinantly joined to a human heavy chain constant domain, and
   wherein the human light chain comprises a human light chain variable domain comprising the amino acid sequence according to SEQ ID NO: 2 recombinantly joined to a human light chain constant domain; and
   a pharmaceutically acceptable carrier.

2. The method of claim 1, wherein administering the pharmaceutical composition comprises administering the pharmaceutical composition subcutaneously.

3. The method of claim 1, wherein administering the pharmaceutical composition comprises administering the pharmaceutical composition intravenously.

4. The method of claim 1, wherein the human subject has AIDS.

5. The method of claim 1, wherein the recombinant human monoclonal anti-HIV antibody comprises a human IgG1 heavy chain constant domain, a human IgG2 heavy chain constant domain, a human IgG3 heavy chain constant domain, or a human IgG4 heavy chain constant domain.

6. The method of claim 5, wherein the recombinant human monoclonal anti-HIV antibody comprises a human IgG1 heavy chain constant domain.

7. The method of claim 1, wherein the human light chain of the recombinant human monoclonal anti-HIV antibody comprises a human kappa light chain.

* * * * *

SEQUENCE LISTING

<160> NUMBER OF SEQ ID NOS: 80

<210> SEQ ID NO 1
<211> LENGTH: 131
<212> TYPE: PRT
<213> ORGANISM: Homo sapiens

<400> SEQUENCE: 1

```
Gln Gly Arg Leu Phe Gln Ser Gly Ala Glu Val Lys Arg Pro Gly Ala
1               5                   10                  15

Ser Val Arg Ile Ser Cys Arg Ala Asp Asp Asp Pro Tyr Thr Asp Asp
            20                  25                  30

Asp Thr Phe Thr Lys Tyr Trp Thr His Trp Ile Arg Gln Ala Pro Gly
        35                  40                  45

Gln Arg Pro Glu Trp Leu Gly Val Ile Ser Pro His Phe Ala Arg Pro
    50                  55                  60

Ile Tyr Ser Tyr Lys Phe Arg Asp Arg Leu Thr Leu Thr Arg Asp Ser
65                  70                  75                  80

Ser Leu Thr Ala Val Tyr Leu Glu Leu Lys Gly Leu Gln Pro Asp Asp
                85                  90                  95

Ser Gly Ile Tyr Phe Cys Ala Arg Asp Pro Phe Gly Asp Arg Ala Pro
            100                 105                 110

His Tyr Asn Tyr His Met Asp Val Trp Gly Gly Gly Thr Ala Val Ile
        115                 120                 125

Val Ser Ser
```

-continued

130

<210> SEQ ID NO 2
<211> LENGTH: 108
<212> TYPE: PRT
<213> ORGANISM: Homo sapiens

<400> SEQUENCE: 2

```
Glu Val Val Leu Thr Gln Ser Pro Ala Ile Leu Ser Val Ser Pro Gly
1               5                   10                  15

Asp Arg Val Ile Leu Ser Cys Arg Ala Ser Gln Gly Leu Asp Ser Ser
            20                  25                  30

His Leu Ala Trp Tyr Arg Phe Lys Arg Gly Gln Ile Pro Thr Leu Val
        35                  40                  45

Ile Phe Gly Thr Ser Asn Arg Ala Arg Gly Thr Pro Asp Arg Phe Ser
    50                  55                  60

Gly Ser Gly Ser Gly Ala Asp Phe Thr Leu Thr Ile Ser Arg Val Glu
65                  70                  75                  80

Pro Glu Asp Phe Ala Thr Tyr Tyr Cys Gln Arg Tyr Gly Gly Thr Pro
                85                  90                  95

Ile Thr Phe Gly Gly Gly Thr Thr Leu Asp Lys Lys
            100                 105
```

<210> SEQ ID NO 3
<211> LENGTH: 131
<212> TYPE: PRT
<213> ORGANISM: Homo sapiens

<400> SEQUENCE: 3

```
Gln Arg Arg Leu Phe Gln Ser Gly Thr Glu Val Lys Arg Pro Gly Ala
1               5                   10                  15

Ser Val Lys Ile Ser Cys Arg Ala Asp Asp Asp Pro Tyr Thr Asp Asp
            20                  25                  30

Asp Thr Phe Thr Lys Tyr Tyr Thr His Trp Ile Arg Gln Ala Pro Gly
        35                  40                  45

Gln Arg Pro Glu Trp Leu Gly Val Ile Ser Pro His Phe Ala Arg Pro
    50                  55                  60

Ile Tyr Ser Tyr Lys Phe Gln Asp Arg Leu Thr Leu Thr Arg Asp Ser
65                  70                  75                  80

Ser Leu Thr Ala Val Tyr Phe Glu Leu Arg Gly Leu Gln Pro Asp Asp
                85                  90                  95

Thr Gly Ile Tyr Phe Cys Ala Arg Asp Pro Phe Gly Asp Met Tyr Pro
            100                 105                 110

His Tyr Asn Tyr His Met Asp Val Trp Gly Gly Gly Thr Thr Val Ile
        115                 120                 125

Val Ser Ala
    130
```

<210> SEQ ID NO 4
<211> LENGTH: 108
<212> TYPE: PRT
<213> ORGANISM: Homo sapiens

<400> SEQUENCE: 4

```
Glu Val Val Leu Thr Gln Ser Pro Ala Ile Leu Ser Val Ser Pro Gly
1               5                   10                  15

Asp Arg Val Ile Leu Ser Cys Lys Ala Ser Glu Gly Leu Ser Ser Ser
            20                  25                  30
```

-continued

```
Asp Leu Ala Trp Tyr Arg Phe Lys Gly Gly Gln Ile Pro Thr Leu Val
        35                  40                  45

Ile Phe Gly Thr Ser Thr Arg Ala Arg Gly Thr Pro Asp Arg Phe Ser
    50                  55                  60

Gly Ser Gly Ser Gly Thr Asp Phe Thr Leu Thr Ile Ser Arg Val Glu
65                  70                  75                  80

Pro Glu Asp Phe Ala Thr Tyr Tyr Cys Gln Arg Tyr Gly Gly Thr Pro
                85                  90                  95

Ile Thr Phe Gly Gly Gly Thr Thr Leu Asp Lys Lys
            100                 105
```

```
<210> SEQ ID NO 5
<211> LENGTH: 131
<212> TYPE: PRT
<213> ORGANISM: Homo sapiens

<400> SEQUENCE: 5
```

```
Gln Gly Arg Leu Phe Gln Ser Gly Thr Glu Val Lys Arg Pro Gly Ala
1                   5                   10                  15

Ser Val Lys Ile Ser Cys Arg Ala Asp Asp Asp Pro Tyr Thr Asp Asp
            20                  25                  30

Asp Thr Phe Thr Lys Tyr Tyr Thr His Trp Ile Arg Gln Ala Pro Gly
        35                  40                  45

Gln Arg Pro Glu Trp Leu Gly Val Ile Ser Pro His Phe Ala Arg Pro
    50                  55                  60

Ile Tyr Ser Tyr Lys Phe Arg Asp Arg Leu Thr Leu Thr Arg Asp Ser
65                  70                  75                  80

Ser Leu Thr Ala Val Tyr Phe Glu Leu Arg Gly Leu Gln Pro Asp Asp
                85                  90                  95

Thr Gly Ile Tyr Phe Cys Ala Arg Asp Pro Phe Gly Asp Met Tyr Pro
            100                 105                 110

His Tyr Asn Tyr His Met Asp Val Trp Gly Gly Gly Thr Thr Val Ile
        115                 120                 125

Val Ser Ala
    130
```

```
<210> SEQ ID NO 6
<211> LENGTH: 108
<212> TYPE: PRT
<213> ORGANISM: Homo sapiens

<400> SEQUENCE: 6
```

```
Glu Val Val Leu Thr Gln Ser Pro Ala Ile Leu Ser Val Ser Pro Gly
1                   5                   10                  15

Asp Arg Val Ile Leu Ser Cys Lys Ala Ser Glu Gly Leu Ser Ser Ser
            20                  25                  30

Asp Leu Ala Trp Tyr Arg Phe Lys Gly Gly Gln Ile Pro Thr Leu Val
        35                  40                  45

Ile Phe Gly Thr Ser Asn Arg Ala Arg Gly Thr Pro Asp Arg Phe Ser
    50                  55                  60

Gly Ser Gly Ser Gly Thr Asp Phe Thr Leu Thr Ile Asn Arg Val Gln
65                  70                  75                  80

Pro Glu Asp Phe Ala Thr Tyr Tyr Cys Gln Arg Tyr Gly Gly Thr Pro
                85                  90                  95

Ile Thr Phe Gly Gly Gly Thr Thr Leu Asp Lys Lys
            100                 105
```

<210> SEQ ID NO 7
<211> LENGTH: 131
<212> TYPE: PRT
<213> ORGANISM: Homo sapiens

<400> SEQUENCE: 7

Gln Gly Arg Leu Phe Gln Ser Gly Thr Glu Val Lys Arg Pro Gly Ala
1               5                   10                  15

Ser Val Lys Ile Ser Cys Arg Ala Asp Asp Asp Pro Tyr Thr Asp Asp
            20                  25                  30

Asp Thr Phe Thr Lys Tyr Tyr Thr His Trp Ile Arg Gln Ala Pro Gly
        35                  40                  45

Gln Arg Pro Glu Trp Leu Gly Val Ile Ser Pro His Phe Ala Arg Pro
    50                  55                  60

Ile Tyr Ser Tyr Lys Phe Gln Asp Arg Leu Thr Leu Thr Arg Asp Ser
65                  70                  75                  80

Ser Leu Thr Ala Val Tyr Phe Glu Leu Arg Asp Leu Gln Ser Asp Asp
                85                  90                  95

Thr Gly Ile Tyr Phe Cys Ala Arg Asp Pro Phe Gly Asp Met Tyr Pro
            100                 105                 110

His Tyr Asn Ser His Met Asp Val Trp Gly Gly Thr Thr Val Ile
        115                 120                 125

Val Ser Ala
    130

<210> SEQ ID NO 8
<211> LENGTH: 108
<212> TYPE: PRT
<213> ORGANISM: Homo sapiens

<400> SEQUENCE: 8

Glu Val Val Leu Thr Gln Ser Pro Ala Ile Leu Ser Val Ser Pro Gly
1               5                   10                  15

Asp Arg Val Ile Leu Ser Cys Lys Ala Ser Glu Gly Leu Ser Ser Ser
            20                  25                  30

Asp Leu Ala Trp Tyr Arg Phe Lys Ser Gly Gln Ile Pro Thr Leu Val
        35                  40                  45

Ile Phe Gly Ala Ser Asn Arg Ala Arg Gly Thr Pro Asp Arg Phe Ser
    50                  55                  60

Gly Ser Gly Ser Gly Thr Asp Phe Thr Leu Thr Ile Asn Arg Val Glu
65                  70                  75                  80

Pro Glu Asp Phe Ala Thr Tyr Tyr Cys Gln Arg Tyr Gly Gly Thr Pro
                85                  90                  95

Ile Thr Phe Gly Gly Gly Thr Thr Leu Asp Lys Lys
            100                 105

<210> SEQ ID NO 9
<211> LENGTH: 131
<212> TYPE: PRT
<213> ORGANISM: Homo sapiens

<400> SEQUENCE: 9

Gln Arg Arg Leu Phe Gln Ser Gly Thr Glu Val Lys Arg Pro Gly Ala
1               5                   10                  15

Ser Val Lys Ile Ser Cys Arg Ala Asp Asp Asp Pro Tyr Thr Asp Asp
            20                  25                  30

-continued

Asp Thr Phe Thr Lys Tyr Tyr Thr His Trp Ile Arg Gln Ala Pro Gly
        35                  40                  45

Gln Pro Pro Glu Trp Leu Gly Val Ile Ser Pro His Phe Ala Arg Pro
    50                  55                  60

Ile Tyr Ser Tyr Lys Phe Arg Asp Arg Leu Thr Leu Thr Arg Asp Ser
65                  70                  75                  80

Ser Leu Thr Ala Val Tyr Phe Glu Leu Arg Gly Leu Gln Pro Asp Asp
                85                  90                  95

Thr Gly Ile Tyr Phe Cys Ala Arg Asp Pro Phe Gly Asp Met Tyr Pro
                100                 105                 110

His Tyr Asn Tyr His Met Asp Val Trp Gly Gly Gly Thr Thr Val Ile
            115                 120                 125

Val Ser Ala
    130

<210> SEQ ID NO 10
<211> LENGTH: 108
<212> TYPE: PRT
<213> ORGANISM: Homo sapiens

<400> SEQUENCE: 10

Glu Ala Val Leu Thr Gln Ser Pro Ala Ile Leu Ser Val Ser Pro Gly
1               5                   10                  15

Asp Arg Val Ile Leu Ser Cys Lys Ala Ser Glu Gly Leu Ser Ser Ser
                20                  25                  30

Asp Leu Ala Trp Tyr Arg Phe Lys Gly Gly Gln Ile Pro Thr Leu Val
            35                  40                  45

Ile Phe Gly Ala Ser Asn Arg Ala Arg Gly Thr Pro Asp Arg Phe Ser
        50                  55                  60

Gly Ser Gly Ser Gly Thr Asp Phe Thr Leu Thr Ile Asn Arg Val Glu
65                  70                  75                  80

Pro Glu Asp Phe Ala Thr Tyr Tyr Cys Gln Arg Tyr Gly Gly Thr Pro
                85                  90                  95

Ile Thr Phe Gly Gly Gly Thr Thr Leu Asp Lys Lys
            100                 105

<210> SEQ ID NO 11
<211> LENGTH: 131
<212> TYPE: PRT
<213> ORGANISM: Homo sapiens

<400> SEQUENCE: 11

Gln Gly Arg Leu Phe Gln Ser Gly Thr Glu Val Lys Arg Pro Gly Ala
1               5                   10                  15

Ser Val Lys Ile Ser Cys Arg Ala Asp Asp Asp Pro Tyr Thr Asp Asp
                20                  25                  30

Asp Thr Phe Thr Lys Tyr His Thr His Trp Ile Arg Gln Ala Pro Gly
            35                  40                  45

Gln Arg Pro Glu Trp Leu Gly Val Ile Ser Pro His Tyr Ala Arg Pro
    50                  55                  60

Ile Tyr Ser Tyr Lys Phe Gln Asp Arg Leu Thr Leu Thr Arg Asp Ser
65                  70                  75                  80

Ser Leu Thr Ala Val Tyr Phe Glu Leu Arg Gly Leu Gln Pro Asp Asp
                85                  90                  95

Thr Gly Ile Tyr Phe Cys Ala Arg Asp Pro Phe Gly Asn Met Tyr Pro
                100                 105                 110

```
His Tyr Asn Tyr His Met Asp Val Trp Gly Gly Gly Thr Thr Val Ile
        115                 120                 125

Val Ser Ala
    130

<210> SEQ ID NO 12
<211> LENGTH: 108
<212> TYPE: PRT
<213> ORGANISM: Homo sapiens

<400> SEQUENCE: 12

Glu Val Val Leu Thr Gln Ser Pro Ala Ile Leu Ser Val Ser Pro Gly
1               5                   10                  15

Asp Arg Val Ile Leu Ser Cys Lys Ala Ser Glu Gly Leu Ser Ser Ser
            20                  25                  30

Asp Leu Ala Trp Tyr Arg Phe Lys Arg Gly Gln Ile Pro Thr Leu Val
        35                  40                  45

Ile Phe Gly Ala Ser Thr Arg Ala Arg Gly Thr Pro Asp Arg Phe Ser
    50                  55                  60

Gly Ser Gly Ser Gly Thr Asp Phe Thr Leu Thr Ile Asn Arg Val Glu
65                  70                  75                  80

Pro Glu Asp Phe Ala Thr Tyr Tyr Cys Gln Arg Tyr Gly Gly Thr Pro
                85                  90                  95

Ile Thr Phe Gly Gly Gly Thr Thr Leu Asp Lys Lys
            100                 105

<210> SEQ ID NO 13
<211> LENGTH: 131
<212> TYPE: PRT
<213> ORGANISM: Homo sapiens

<400> SEQUENCE: 13

Gln Gly Arg Leu Phe Gln Ser Gly Ala Glu Val Lys Arg Pro Gly Ala
1               5                   10                  15

Ser Val Lys Ile Ser Cys Arg Ala Asp Asp Asp Pro Tyr Thr Asp Asp
            20                  25                  30

Asp Thr Phe Thr Lys Tyr Tyr Thr His Trp Ile Arg Gln Ala Pro Gly
        35                  40                  45

Gln Arg Pro Glu Trp Leu Gly Val Ile Ser Pro His Phe Ala Arg Pro
    50                  55                  60

Ile Tyr Ser Tyr Lys Phe Arg Asp Arg Leu Thr Leu Thr Arg Asp Ser
65                  70                  75                  80

Ser Leu Thr Ala Val Tyr Phe Glu Leu Arg Gly Leu Gln Pro Asp Asp
                85                  90                  95

Thr Gly Ile Tyr Phe Cys Ala Arg Asp Pro Phe Gly Asp Met Tyr Pro
            100                 105                 110

His Tyr Asn Tyr His Met Asp Val Trp Gly Gly Gly Thr Thr Val Ile
        115                 120                 125

Val Ser Ala
    130

<210> SEQ ID NO 14
<211> LENGTH: 108
<212> TYPE: PRT
<213> ORGANISM: Homo sapiens

<400> SEQUENCE: 14

Glu Val Val Leu Thr Gln Ser Pro Ala Ile Leu Ser Val Ser Pro Gly
```

```
1               5                   10                  15
Asp Arg Val Ile Leu Ser Cys Lys Ala Ser Glu Gly Leu Ser Ser Ser
            20                  25                  30

Asp Leu Ala Trp Tyr Arg Phe Lys Gly Gly Gln Ile Pro Thr Leu Val
            35                  40                  45

Ile Phe Ala Thr Ser Asn Arg Ala Arg Gly Thr Pro Asp Arg Phe Ser
            50                  55                  60

Gly Ser Gly Ser Gly Thr Asp Phe Thr Leu Thr Ile Ser Lys Val Gln
65                  70                  75                  80

Pro Glu Asp Phe Ala Thr Tyr Tyr Cys Gln Arg Tyr Gly Gly Thr Pro
                85                  90                  95

Ile Thr Phe Gly Gly Gly Thr Thr Leu Asp Lys Lys
                100                 105
```

<210> SEQ ID NO 15
<211> LENGTH: 131
<212> TYPE: PRT
<213> ORGANISM: Homo sapiens

<400> SEQUENCE: 15

```
Gln Gly Arg Leu Phe Gln Ser Gly Thr Glu Val Lys Arg Pro Gly Ala
1               5                   10                  15

Ser Val Lys Ile Ser Cys Arg Ala Asp Asp Asp Pro Tyr Thr Asp Asp
            20                  25                  30

Asp Thr Phe Thr Lys Tyr Tyr Thr His Trp Ile Arg Gln Ala Pro Gly
            35                  40                  45

Gln Arg Pro Glu Trp Leu Gly Val Ile Ser Pro His Tyr Ala Arg Pro
            50                  55                  60

Ile Tyr Ser Tyr Lys Phe Arg Asp Arg Leu Thr Leu Thr Arg Asp Ser
65                  70                  75                  80

Ser Leu Thr Ala Val Tyr Phe Glu Leu Arg Gly Leu Gln Pro Asp Asp
                85                  90                  95

Thr Gly Ile Tyr Phe Cys Ala Arg Asp Pro Phe Gly Asp Met Tyr Pro
                100                 105                 110

His Tyr Asn Tyr His Met Asp Val Trp Gly Gly Gly Thr Thr Val Ile
            115                 120                 125

Val Ser Ala
    130
```

<210> SEQ ID NO 16
<211> LENGTH: 108
<212> TYPE: PRT
<213> ORGANISM: Homo sapiens

<400> SEQUENCE: 16

```
Glu Val Val Leu Thr Gln Ser Pro Ala Ile Leu Ser Val Ser Pro Gly
1               5                   10                  15

Asp Arg Val Ile Leu Ser Cys Lys Ala Ser Glu Gly Leu Ser Ser Ser
            20                  25                  30

Asp Leu Ala Trp Tyr Arg Phe Lys Gly Gly Gln Ile Pro Thr Leu Val
            35                  40                  45

Ile Phe Gly Ala Ser Asn Arg Ala Arg Gly Thr Pro Asp Arg Phe Ser
            50                  55                  60

Gly Ser Gly Ser Gly Thr Asp Phe Thr Leu Thr Ile Asn Arg Val Glu
65                  70                  75                  80

Pro Glu Asp Phe Ala Thr Tyr Tyr Cys Gln Arg Tyr Gly Gly Thr Pro
```

```
                     85                  90                  95

Ile Thr Phe Gly Gly Gly Thr Thr Leu Asp Lys Lys
            100                 105

<210> SEQ ID NO 17
<211> LENGTH: 131
<212> TYPE: PRT
<213> ORGANISM: Homo sapiens

<400> SEQUENCE: 17

Gln Arg Arg Leu Phe Gln Ser Gly Thr Glu Val Lys Arg Pro Gly Ala
1               5                   10                  15

Ser Val Lys Ile Ser Cys Arg Ala Asp Asp Asp Pro Tyr Thr Asp Asp
            20                  25                  30

Asp Thr Phe Thr Lys Tyr Tyr Thr His Trp Ile Arg Gln Ala Pro Gly
        35                  40                  45

Gln Arg Pro Glu Trp Leu Gly Val Ile Ser Pro His Tyr Ala Arg Pro
    50                  55                  60

Ile Tyr Ser Tyr Lys Phe Gln Asp Arg Leu Thr Leu Thr Arg Asp Ser
65                  70                  75                  80

Ser Leu Thr Ala Val Tyr Phe Glu Leu Arg Gly Leu Gln Pro Asp Asp
                85                  90                  95

Thr Gly Ile Tyr Phe Cys Ala Arg Asp Pro Phe Gly Asp Met Tyr Pro
            100                 105                 110

His Tyr Asn Tyr His Met Asp Val Trp Gly Gly Gly Thr Thr Leu Ile
            115                 120                 125

Val Ser Ala
    130

<210> SEQ ID NO 18
<211> LENGTH: 108
<212> TYPE: PRT
<213> ORGANISM: Homo sapiens

<400> SEQUENCE: 18

Glu Val Val Leu Thr Gln Ser Pro Ala Ile Leu Ser Val Ser Pro Gly
1               5                   10                  15

Asp Arg Val Ile Leu Ser Cys Lys Ala Ser Glu Gly Leu Ser Ser Ser
            20                  25                  30

Asp Leu Ala Trp Tyr Arg Phe Lys Ser Gly Gln Ile Pro Thr Leu Val
        35                  40                  45

Ile Phe Gly Ala Ser Asn Arg Ala Arg Gly Thr Pro Asp Arg Phe Ala
    50                  55                  60

Gly Ser Gly Ser Gly Thr Asp Phe Thr Leu Thr Ile Asn Arg Val Glu
65                  70                  75                  80

Pro Glu Asp Phe Ala Thr Tyr Tyr Cys Gln Arg Tyr Gly Gly Thr Pro
                85                  90                  95

Ile Thr Phe Gly Gly Gly Thr Thr Leu Asp Lys Lys
            100                 105

<210> SEQ ID NO 19
<211> LENGTH: 131
<212> TYPE: PRT
<213> ORGANISM: Homo sapiens

<400> SEQUENCE: 19

Gln Arg Arg Leu Phe Gln Ser Gly Thr Glu Val Lys Arg Pro Gly Ala
1               5                   10                  15
```

```
Ser Val Arg Ile Ser Cys Arg Ala Asp Asp Asp Pro Tyr Thr Asp Asp
        20                  25                  30

Asp Thr Phe Thr Lys Tyr Trp Thr His Trp Ile Arg Gln Ala Pro Gly
        35                  40                  45

Gln Arg Pro Glu Trp Leu Gly Val Ile Ser Pro His Phe Ala Arg Pro
    50                  55                  60

Ile Tyr Ser Tyr Lys Phe Gln Asp Arg Leu Thr Leu Thr Arg Asp Ser
65                  70                  75                  80

Ser Leu Thr Gly Val Tyr Leu Glu Leu Lys Gly Leu Gln Leu Asp Asp
                85                  90                  95

Ser Gly Ile Tyr Phe Cys Ala Arg Asp Pro Phe Gly Asp Arg Ala Pro
            100                 105                 110

His Tyr Asn Tyr His Met Asp Val Trp Gly Gly Gly Thr Ala Val Ile
            115                 120                 125

Val Ser Ser
    130
```

```
<210> SEQ ID NO 20
<211> LENGTH: 108
<212> TYPE: PRT
<213> ORGANISM: Homo sapiens

<400> SEQUENCE: 20

Glu Val Val Leu Thr Gln Ser Pro Ala Ile Leu Ser Val Ser Pro Gly
1               5                   10                  15

Asp Arg Val Ser Phe Ser Cys Arg Ala Ser Glu Gly Leu Asp Thr Ser
            20                  25                  30

Gln Leu Ala Trp Tyr Arg Phe Lys Arg Gly Gln Ile Pro Thr Leu Val
        35                  40                  45

Ile Phe Ala Thr Ser Asn Arg Ala Arg Gly Thr Pro Asp Arg Phe Ser
    50                  55                  60

Gly Ser Gly Ser Gly Ala Asp Phe Thr Leu Thr Ile Asn Arg Val Glu
65                  70                  75                  80

Pro Glu Asp Phe Ala Thr Tyr Tyr Cys Gln Arg Tyr Gly Ala Thr Pro
                85                  90                  95

Ile Thr Phe Gly Gly Gly Thr Thr Leu Asp Lys Lys
            100                 105
```

```
<210> SEQ ID NO 21
<211> LENGTH: 131
<212> TYPE: PRT
<213> ORGANISM: Homo sapiens

<400> SEQUENCE: 21

Gln Arg Arg Leu Phe Gln Ser Gly Thr Glu Val Lys Arg Pro Gly Ala
1               5                   10                  15

Ser Val Lys Ile Ser Cys Arg Ala Asp Asp Asp Pro Tyr Thr Asp Asp
            20                  25                  30

Asp Thr Phe Thr Lys Tyr Tyr Thr His Trp Ile Arg Gln Ala Pro Gly
            35                  40                  45

Gln Arg Pro Glu Trp Leu Gly Val Ile Ser Pro His Phe Ala Arg Pro
    50                  55                  60

Ile Tyr Ser Tyr Lys Phe Gln Asp Arg Leu Thr Leu Thr Arg Asp Ser
65                  70                  75                  80

Ser Leu Thr Ala Val Tyr Phe Glu Leu Arg Gly Leu Gln Pro Asp Asp
                85                  90                  95
```

```
Thr Gly Ile Tyr Phe Cys Ala Arg Asp Pro Phe Gly Asp Met Tyr Pro
            100                 105                 110

His Tyr Asn Tyr His Met Asp Val Trp Gly Gly Gly Thr Thr Val Ile
        115                 120                 125

Val Ser Ala
    130

<210> SEQ ID NO 22
<211> LENGTH: 108
<212> TYPE: PRT
<213> ORGANISM: Homo sapiens

<400> SEQUENCE: 22

Glu Val Val Leu Thr Gln Ser Pro Ala Ile Leu Ser Val Ser Pro Gly
1               5                   10                  15

Asp Arg Val Ile Leu Ser Cys Lys Ala Ser Glu Gly Leu Ser Ser Ser
            20                  25                  30

Asp Leu Ala Trp Tyr Arg Phe Lys Gly Gly Gln Ile Pro Thr Leu Val
        35                  40                  45

Ile Phe Gly Thr Ser Thr Arg Ala Arg Gly Thr Pro Asp Arg Phe Ser
    50                  55                  60

Gly Ser Gly Ser Gly Thr Asp Phe Thr Leu Thr Ile Ser Arg Val Glu
65                  70                  75                  80

Pro Glu Asp Phe Ala Thr Tyr Tyr Cys Gln Arg Tyr Gly Gly Thr Pro
                85                  90                  95

Ile Thr Phe Gly Gly Gly Thr Thr Leu Asp Lys Lys
            100                 105

<210> SEQ ID NO 23
<211> LENGTH: 131
<212> TYPE: PRT
<213> ORGANISM: Homo sapiens

<400> SEQUENCE: 23

Gln Gly Arg Leu Phe Gln Ser Gly Ala Glu Val Lys Arg Pro Gly Ala
1               5                   10                  15

Ser Val Arg Ile Ser Cys Arg Ala Asp Asp Asp Pro Tyr Thr Asp Asp
            20                  25                  30

Asp Thr Phe Thr Lys Tyr Trp Thr His Trp Ile Arg Gln Ala Pro Gly
        35                  40                  45

Gln Arg Pro Glu Trp Leu Gly Val Ile Ser Pro His Phe Ala Arg Pro
    50                  55                  60

Ile Tyr Ser Tyr Lys Phe Arg Asp Arg Leu Thr Leu Thr Arg Asp Ser
65                  70                  75                  80

Ser Leu Thr Ala Val Tyr Leu Glu Leu Lys Gly Leu Gln Pro Asp Asp
                85                  90                  95

Ser Gly Ile Tyr Phe Cys Ala Arg Asp Pro Phe Gly Asp Arg Ala Pro
            100                 105                 110

His Tyr Asn Tyr His Met Asp Val Trp Gly Gly Gly Thr Ala Val Ile
        115                 120                 125

Val Ser Ser
    130

<210> SEQ ID NO 24
<211> LENGTH: 108
<212> TYPE: PRT
<213> ORGANISM: Homo sapiens
```

<400> SEQUENCE: 24

```
Glu Val Val Leu Thr Gln Ser Pro Ala Ile Leu Ser Val Ser Pro Gly
1               5                   10                  15

Asp Arg Val Ile Leu Ser Cys Arg Ala Ser Gln Gly Leu Asp Ser Ser
                20                  25                  30

His Leu Ala Trp Tyr Arg Phe Lys Arg Gly Gln Ile Pro Thr Leu Val
            35                  40                  45

Ile Phe Gly Thr Ser Asn Arg Ala Arg Gly Thr Pro Asp Arg Phe Ser
        50                  55                  60

Gly Ser Gly Ser Gly Ala Asp Phe Thr Leu Thr Ile Ser Arg Val Glu
65                  70                  75                  80

Pro Glu Asp Phe Ala Thr Tyr Tyr Cys Gln Arg Tyr Gly Gly Thr Pro
                85                  90                  95

Ile Thr Phe Gly Gly Gly Thr Thr Leu Asp Lys Lys
                100                 105
```

<210> SEQ ID NO 25
<211> LENGTH: 131
<212> TYPE: PRT
<213> ORGANISM: Homo sapiens

<400> SEQUENCE: 25

```
Gln Ala His Leu Phe Gln Ser Gly Ala Glu Leu Lys Arg Pro Gly Ala
1               5                   10                  15

Ser Val Arg Ile Ser Cys Arg Ala Asp Asp Asp Pro Tyr Thr Asp Asp
                20                  25                  30

Asp Thr Phe Thr Lys Tyr Tyr Thr His Trp Ile Arg Gln Ala Pro Gly
            35                  40                  45

Gln Arg Pro Glu Trp Leu Gly Val Ile Ser Pro His Phe Ala Arg Pro
        50                  55                  60

Ile Tyr Ser Tyr Lys Phe Gln Asp Arg Leu Thr Leu Thr Arg Asp Ser
65                  70                  75                  80

Ser Leu Thr Ala Val Tyr Leu Glu Leu Arg Ser Leu Arg Leu Asp Asp
                85                  90                  95

Thr Gly Ile Tyr Tyr Cys Ala Arg Asp Pro Phe Gly Glu Arg Ala Pro
                100                 105                 110

His Tyr Asn Tyr His Met Asp Val Trp Gly Ala Gly Thr Thr Val Ile
            115                 120                 125

Val Ser Ser
        130
```

<210> SEQ ID NO 26
<211> LENGTH: 108
<212> TYPE: PRT
<213> ORGANISM: Homo sapiens

<400> SEQUENCE: 26

```
Glu Val Val Leu Thr Gln Ser Pro Ala Ile Leu Ser Ala Ser Pro Gly
1               5                   10                  15

Asp Arg Val Val Leu Ser Cys Arg Ala Ser Glu Gly Leu Asp Ser Ser
                20                  25                  30

Gln Leu Ala Trp Tyr Arg Phe Lys Asp Gly Gln Ile Pro Arg Leu Val
            35                  40                  45

Leu Phe Gly Val Ser Asn Arg Ala Arg Gly Thr Pro Asp Arg Phe Ser
        50                  55                  60
```

-continued

Gly Gly Gly Ser Gly Ala Asp Phe Thr Leu Thr Ile Ser Arg Val Glu
65               70              75              80

Arg Glu Asp Phe Ala Thr Tyr Tyr Cys Gln Arg Phe Gly Ala Thr Pro
                85              90              95

Ile Thr Phe Gly Gly Gly Thr Arg Leu Asp Met Asn
            100             105

<210> SEQ ID NO 27
<211> LENGTH: 131
<212> TYPE: PRT
<213> ORGANISM: Homo sapiens

<400> SEQUENCE: 27

Gln Gly Arg Phe Phe Gln Ser Gly Ala Glu Val Lys Arg Pro Gly Ala
1               5               10              15

Ser Val Arg Ile Ser Cys Arg Ala Asp Asp Asp Pro Tyr Thr Asp Asp
            20              25              30

Asp Thr Phe Thr Lys Tyr Trp Thr His Trp Ile Arg Gln Ala Pro Gly
        35              40              45

Gln Arg Pro Glu Trp Leu Gly Val Ile Ser Pro His Phe Ala Arg Pro
    50              55              60

Ile Tyr Ser Tyr Lys Phe Arg Asp Arg Leu Thr Leu Thr Arg Asp Ser
65              70              75              80

Ser Leu Thr Ala Val Tyr Leu Glu Leu Gln Gly Leu Gln Pro Asp Asp
            85              90              95

Ser Gly Ile Tyr Tyr Cys Ala Arg Asp Pro Phe Gly Asp Arg Ala Pro
            100             105             110

His Tyr Asn Tyr His Met Asp Val Trp Gly Gly Gly Thr Ala Val Ile
        115             120             125

Val Ser Ser
    130

<210> SEQ ID NO 28
<211> LENGTH: 108
<212> TYPE: PRT
<213> ORGANISM: Homo sapiens

<400> SEQUENCE: 28

Glu Val Val Leu Thr Gln Ser Pro Ala Ile Leu Ser Val Ser Pro Gly
1               5               10              15

Asp Arg Val Ile Leu Ser Cys Arg Ala Ser Glu Gly Leu Asp Pro Thr
            20              25              30

His Leu Ala Trp Tyr Arg Phe Lys Arg Gly Gln Ile Pro Thr Leu Val
        35              40              45

Ile Phe Gly Thr Ser Asn Arg Ala Arg Gly Thr Pro Asp Arg Phe Ser
    50              55              60

Gly Ser Gly Ser Glu Ala Asp Phe Thr Leu Thr Ile Thr Arg Val Glu
65              70              75              80

Pro Glu Asp Phe Ala Thr Tyr Tyr Cys Gln Arg Tyr Gly Gly Thr Pro
                85              90              95

Ile Thr Phe Gly Gly Gly Thr Thr Leu Asp Lys Lys
            100             105

<210> SEQ ID NO 29
<211> LENGTH: 123
<212> TYPE: PRT
<213> ORGANISM: Homo sapiens

<400> SEQUENCE: 29

```
Gln Leu Val Gln Trp Gly Gly Gly Val Lys Arg Pro Gly Ala Ser Val
1               5                   10                  15

Arg Ile Ser Cys Gln Cys Pro Glu Asp Thr Phe Thr Lys Tyr Tyr Ile
                20                  25                  30

His Trp Val Arg Gln Ala Pro Gly Arg Gly Leu Glu Trp Leu Gly Met
            35                  40                  45

Val Ser Pro His Gly Gly Arg Pro Phe His Thr Ser Glu Phe Arg Asp
        50                  55                  60

Arg Leu Thr Met Thr Arg Asp Ile His Glu Thr Thr His His Met Val
65                  70                  75                  80

Leu Ser Gly Leu Gly Val Ala Asp Ser Gly Thr Tyr Phe Cys Ala Arg
                85                  90                  95

Asp Pro Leu Gly Glu Lys Ser Pro Ala Tyr Ser His His Met Asp Val
            100                 105                 110

Trp Gly Gly Gly Ala Thr Val Ile Val Ser Ser
        115                 120
```

<210> SEQ ID NO 30
<211> LENGTH: 111
<212> TYPE: PRT
<213> ORGANISM: Homo sapiens

<400> SEQUENCE: 30

```
Ala Val Val Leu Thr Gln Ser Pro Val Thr Leu Ser Val Ser Pro Gly
1               5                   10                  15

Glu Thr Ala Ile Leu Ser Cys Arg Ala Ser His Gly Leu Asp Thr Arg
                20                  25                  30

His Val Thr Trp Phe Gln Gln Lys Arg Gly Gln Ala Pro Arg Leu Leu
            35                  40                  45

Ile Phe Ala Thr Tyr Arg Arg Ala Ser Gly Val Ser Asp Arg Phe Arg
        50                  55                  60

Ala Thr Asp Ser Gly Ser Ala Thr Asp Phe Asn Leu Thr Ile Thr Ala
65                  70                  75                  80

Val Glu Pro Ala Asp Phe Ala Thr Tyr Phe Cys Gln Thr Tyr Gly Ala
                85                  90                  95

Ile Thr Pro Ile Thr Phe Gly Gly Gly Thr Lys Val Asp Leu Lys
            100                 105                 110
```

<210> SEQ ID NO 31
<211> LENGTH: 123
<212> TYPE: PRT
<213> ORGANISM: Homo sapiens

<400> SEQUENCE: 31

```
Gln Leu Val Gln Trp Gly Gly Gly Val Lys Arg Pro Gly Ala Ser Val
1               5                   10                  15

Arg Ile Ser Cys Gln Cys Pro Glu Asp Thr Phe Thr Lys Tyr Tyr Ile
                20                  25                  30

His Trp Val Arg Gln Ala Pro Gly Arg Gly Leu Glu Trp Leu Gly Met
            35                  40                  45

Val Ser Pro His Gly Gly Arg Pro Phe His Thr Ser Glu Phe Arg Asp
        50                  55                  60

Arg Leu Thr Met Thr Arg Glu Ile His Glu Thr Thr His His Met Val
65                  70                  75                  80

Leu Ser Gly Leu Gly Val Gly Asp Ser Gly Thr Tyr Phe Cys Ala Arg
```

```
            85                  90                  95

Asp Pro Leu Gly Glu Lys Ser Pro Ala Tyr Ser His His Met Asp Val
            100                 105                 110

Trp Gly Gly Gly Ala Thr Val Ile Val Ser Ser
        115                 120

<210> SEQ ID NO 32
<211> LENGTH: 111
<212> TYPE: PRT
<213> ORGANISM: Homo sapiens

<400> SEQUENCE: 32

Ala Val Val Leu Thr Gln Ser Pro Val Thr Leu Ser Val Ser Pro Gly
1               5                   10                  15

Glu Ser Ala Val Leu Ser Cys Arg Ala Ser His Gly Leu Asp Thr Arg
            20                  25                  30

His Val Thr Trp Phe Gln Gln Lys Arg Gly Gln Ala Pro Arg Leu Leu
        35                  40                  45

Ile Phe Ala Thr Ser Arg Arg Ala Ser Gly Val Ser Asp Arg Phe Arg
    50                  55                  60

Ala Thr Asp Gly Gly Ser Ala Thr Asp Phe Asn Leu Thr Ile Thr Ala
65                  70                  75                  80

Val Glu Pro Ala Asp Phe Ala Thr Tyr Tyr Cys Gln Thr Tyr Gly Ala
            85                  90                  95

Ile Thr Pro Ile Thr Phe Gly Gly Gly Thr Lys Leu Asp Leu Lys
            100                 105                 110

<210> SEQ ID NO 33
<211> LENGTH: 126
<212> TYPE: PRT
<213> ORGANISM: Homo sapiens

<400> SEQUENCE: 33

Gln Leu Ala Gln Ser Gly Gly Gly Val Lys Lys Pro Gly Ala Ser Val
1               5                   10                  15

Lys Ile Ser Cys Val Thr Pro Glu Ser Thr Phe Thr Lys Tyr Trp Leu
            20                  25                  30

His Trp Val Arg Gln Ala Pro Gly Gln Gly Phe Glu Trp Leu Gly Val
        35                  40                  45

Val Ser Pro His Gly Gly Arg Pro Met Phe Ala Asn Lys Phe Arg Asp
    50                  55                  60

Arg Leu Thr Leu Thr Arg Asp Ile His Thr Thr Thr His Tyr Met Glu
65                  70                  75                  80

Leu Arg Gly Leu Thr Ser Asp Asp Thr Ala Ile Tyr Tyr Cys Ala Arg
            85                  90                  95

Asp Ser Phe Gly Glu Thr Phe Arg His Ser Gly Asp Gln Pro Tyr Gln
            100                 105                 110

Met Asp Val Trp Gly Gly Gly Thr Asn Ile Val Val Ser Ser
        115                 120                 125

<210> SEQ ID NO 34
<211> LENGTH: 109
<212> TYPE: PRT
<213> ORGANISM: Homo sapiens

<400> SEQUENCE: 34

Glu Pro Val Leu Thr Gln Ser Pro Gly Thr Leu Ser Leu Ser Pro Gly
1               5                   10                  15
```

```
Glu Arg Ala Thr Leu Ser Cys Arg Ala Ser Gln Gly Phe Ser Val Asp
            20                  25                  30

His Leu Ala Trp Phe Gln Lys Arg Pro Gly Arg Pro Pro Arg Leu Leu
            35                  40                  45

Ile Phe Glu Thr Ser Arg Arg Ala Asn Gly Ser Pro Asp Arg Phe Ser
        50                  55                  60

Gly Ser Ala Ser Gly Ala Glu Tyr Thr Leu Thr Ile Ser Asn Val Glu
65                  70                  75                  80

Pro Glu Asp Phe Ala Val Tyr Tyr Cys Gln Ser Tyr Gly Ser Ile Thr
                85                  90                  95

Pro Leu Ile Phe Gly Gly Gly Thr Arg Val Asp Val Lys
            100                 105
```

```
<210> SEQ ID NO 35
<211> LENGTH: 125
<212> TYPE: PRT
<213> ORGANISM: Homo sapiens

<400> SEQUENCE: 35

Gln Leu Val Gln Ser Gly Gly Gly Val Arg Arg Pro Gly Ala Ser Val
1               5                   10                  15

Lys Ile Ser Cys Glu Thr Pro Glu Tyr Thr Phe Thr Lys Tyr Trp Leu
            20                  25                  30

His Trp Leu Arg Gln Ala Pro Gly Arg Gly Leu Glu Trp Met Gly Val
            35                  40                  45

Val Ser Pro His Gly Gly Arg Pro Met Phe Ala Phe Glu Phe Arg Asp
        50                  55                  60

Arg Leu Thr Leu Thr Arg Asp Ile His Thr Thr Thr His Tyr Met Glu
65                  70                  75                  80

Leu Arg Gly Leu Thr Ser Asp Asp Thr Ala Val Tyr Phe Cys Ala Arg
                85                  90                  95

Asp Ser Phe Gly Glu Thr Phe Arg Gly His Asp Gln Pro Tyr Gln Met
            100                 105                 110

Asp Val Trp Gly Gly Gly Thr Thr Val Val Val Ser Ser
        115                 120                 125
```

```
<210> SEQ ID NO 36
<211> LENGTH: 109
<212> TYPE: PRT
<213> ORGANISM: Homo sapiens

<400> SEQUENCE: 36

Glu Pro Val Leu Thr Gln Ser Pro Gly Thr Leu Ser Leu Ser Pro Gly
1               5                   10                  15

Glu Gly Ala Thr Leu Ser Cys Arg Ala Arg Gln Gly Phe Ser Ala Asp
            20                  25                  30

His Val Ala Trp Phe Gln Lys Lys Pro Gly Arg Pro Pro Arg Leu Leu
            35                  40                  45

Ile Phe Glu Ala Ser Arg Arg Ala Ser Gly Thr Pro Glu Arg Phe Ser
        50                  55                  60

Gly Gly Gly Ser Gly Pro Glu Tyr Thr Leu Thr Ile Thr Arg Val Glu
65                  70                  75                  80

Pro Glu Asp Phe Ala Val Tyr Tyr Cys Gln Ser Tyr Gly Ser Ile Thr
                85                  90                  95

Pro Leu Val Phe Gly Gly Gly Thr Arg Val Asp Val Lys
            100                 105
```

```
<210> SEQ ID NO 37
<211> LENGTH: 125
<212> TYPE: PRT
<213> ORGANISM: Homo sapiens

<400> SEQUENCE: 37

Gln Leu Val Gln Ser Gly Gly Gly Val Arg Arg Pro Gly Ala Ser Val
1               5                   10                  15

Lys Val Ser Cys Glu Thr Pro Glu Tyr Thr Phe Thr Lys Tyr Trp Leu
            20                  25                  30

His Trp Leu Arg Gln Ala Pro Gly Arg Gly Leu Glu Trp Met Gly Val
        35                  40                  45

Val Ser Pro His Gly Gly Arg Pro Met Phe Ala Phe Glu Phe Arg Asp
    50                  55                  60

Arg Leu Thr Leu Thr Arg Asp Ile His Thr Thr Thr His Tyr Met Glu
65                  70                  75                  80

Leu Arg Gly Leu Thr Ser Asp Asp Thr Ala Val Tyr Phe Cys Ala Arg
                85                  90                  95

Asp Ser Phe Gly Glu Thr Phe Arg Gly His Asp Gln Pro Tyr Gln Met
            100                 105                 110

Asp Leu Trp Gly Gly Gly Thr Thr Val Val Val Ser Ser
        115                 120                 125

<210> SEQ ID NO 38
<211> LENGTH: 109
<212> TYPE: PRT
<213> ORGANISM: Homo sapiens

<400> SEQUENCE: 38

Glu Pro Val Leu Thr Gln Ser Pro Gly Thr Leu Ser Leu Ser Pro Gly
1               5                   10                  15

Glu Gly Val Thr Leu Ser Cys Arg Ala Arg Gln Gly Phe Ser Ala Asp
            20                  25                  30

His Val Ala Trp Phe Gln Lys Lys Pro Gly Arg Pro Pro Arg Leu Leu
        35                  40                  45

Ile Phe Glu Thr Ser Arg Arg Ala Ser Gly Thr Pro Glu Arg Phe Ser
    50                  55                  60

Gly Gly Gly Ser Gly Pro Glu Tyr Thr Leu Thr Ile Thr Arg Val Glu
65                  70                  75                  80

Pro Glu Asp Phe Ala Val Tyr Tyr Cys Gln Ser Tyr Gly Ser Ile Thr
                85                  90                  95

Pro Leu Val Phe Gly Gly Gly Thr Arg Val Asp Val Lys
            100                 105

<210> SEQ ID NO 39
<211> LENGTH: 125
<212> TYPE: PRT
<213> ORGANISM: Homo sapiens

<400> SEQUENCE: 39

Gln Leu Val Gln Ser Gly Gly Gly Val Arg Arg Pro Gly Ala Ser Val
1               5                   10                  15

Lys Ile Ser Cys Glu Thr Pro Glu Asp Thr Phe Thr Lys Tyr Trp Leu
            20                  25                  30

His Trp Leu Arg Gln Ala Pro Gly Gln Gly Leu Glu Trp Met Gly Val
        35                  40                  45
```

-continued

```
Val Ser Pro His Gly Gly Arg Pro Met Phe Ala Phe Glu Phe Arg Asp
    50              55              60

Arg Leu Thr Leu Thr Arg Asp Ile His Thr Thr Thr His Phe Met Glu
65              70              75              80

Leu Arg Gly Leu Thr Ser Asp Asp Thr Ala Val Tyr Tyr Cys Ala Arg
                85              90              95

Asp Pro Phe Gly Glu Thr Phe Arg Gly His Asp Gln Pro Tyr Arg Met
            100             105             110

Asp Val Trp Gly Gly Gly Thr Thr Ile Val Val Ser Ser
        115             120             125

<210> SEQ ID NO 40
<211> LENGTH: 109
<212> TYPE: PRT
<213> ORGANISM: Homo sapiens

<400> SEQUENCE: 40

Glu Pro Val Leu Thr Gln Ser Pro Gly Thr Leu Ser Val Ser Pro Gly
1               5               10              15

Glu Gly Ala Thr Leu Ser Cys Arg Ala Arg Gln Gly Phe Ser Ala Asp
            20              25              30

His Val Ala Trp Phe Gln Lys Lys Pro Gly Arg Pro Pro Arg Leu Leu
        35              40              45

Ile Phe Glu Ala Ser Arg Arg Ala Ser Gly Thr Pro Glu Arg Phe Ser
    50              55              60

Gly Ser Gly Ser Gly Pro Glu Tyr Thr Leu Thr Ile Thr Arg Val Glu
65              70              75              80

Ala Glu Asp Phe Ala Val Tyr Tyr Cys Gln Ser Tyr Gly Ser Ile Thr
                85              90              95

Pro Leu Val Phe Gly Gly Gly Thr Arg Val Asp Val Lys
            100             105

<210> SEQ ID NO 41
<211> LENGTH: 125
<212> TYPE: PRT
<213> ORGANISM: Homo sapiens

<400> SEQUENCE: 41

Gln Leu Val Gln Ser Gly Gly Gly Val Lys Arg Pro Gly Ala Ser Val
1               5               10              15

Lys Ile Ser Cys Glu Thr Pro Glu Tyr Thr Phe Thr Lys Tyr Trp Leu
            20              25              30

His Trp Leu Arg Gln Ala Pro Gly Gln Gly Leu Glu Trp Met Gly Val
        35              40              45

Val Ser Pro His Gly Gly Arg Pro Met Phe Ala Phe Glu Phe Arg Asp
    50              55              60

Arg Leu Thr Leu Thr Arg Asp Ile His Thr Thr Thr His Tyr Met Glu
65              70              75              80

Leu Gly Gly Leu Thr Leu Asp Asp Thr Ala Val Tyr Tyr Cys Ala Arg
                85              90              95

Asp Pro Phe Gly Glu Thr Phe Arg Gly Arg Glu Gln Pro Tyr Gln Met
            100             105             110

Asp Val Trp Gly Gly Gly Thr Thr Ile Val Val Thr Ser
        115             120             125

<210> SEQ ID NO 42
<211> LENGTH: 109
```

```
<212> TYPE: PRT
<213> ORGANISM: Homo sapiens

<400> SEQUENCE: 42

Glu Ala Leu Leu Thr Gln Ser Pro Gly Thr Leu Ser Leu Ser Pro Gly
1               5                   10                  15

Glu Gly Ala Thr Leu Ser Cys Arg Ala Arg Gln Gly Phe Ser Ala Asp
                20                  25                  30

His Val Ala Trp Phe Gln Lys Lys Pro Gly Arg Pro Pro Arg Leu Leu
        35                  40                  45

Ile Phe Glu Ala Ser Arg Arg Ala Ser Gly Thr Pro Glu Arg Phe Ser
        50                  55                  60

Gly Ser Gly Ser Gly Pro Glu Tyr Thr Leu Thr Ile Thr Arg Val Glu
65                  70                  75                  80

Pro Glu Asp Phe Ala Val Tyr Tyr Cys Gln Ser Tyr Gly Ser Ile Thr
                85                  90                  95

Pro Leu Val Phe Gly Gly Gly Thr Arg Val Asp Val Lys
                100                 105

<210> SEQ ID NO 43
<211> LENGTH: 125
<212> TYPE: PRT
<213> ORGANISM: Homo sapiens

<400> SEQUENCE: 43

Gln Leu Val Gln Ser Gly Gly Gly Val Arg Arg Pro Gly Ala Ser Val
1               5                   10                  15

Lys Ile Ser Cys Glu Thr Pro Glu Asp Thr Phe Thr Lys Tyr Trp Leu
                20                  25                  30

His Trp Leu Arg Gln Ala Pro Gly Gln Gly Leu Glu Trp Met Gly Val
        35                  40                  45

Val Ser Pro His Gly Gly Arg Pro Met Phe Ala Phe Glu Phe Arg Asp
        50                  55                  60

Arg Leu Thr Leu Thr Arg Asp Ile His Thr Thr Thr His Phe Met Glu
65                  70                  75                  80

Leu Gly Gly Leu Thr Ser Asp Asp Thr Ala Val Tyr Tyr Cys Ala Arg
                85                  90                  95

Asp Pro Phe Gly Glu Thr Phe Arg Gly His Asp Gln Pro Tyr Arg Met
                100                 105                 110

Asp Val Trp Gly Gly Gly Thr Thr Ile Val Val Ser Ser
        115                 120                 125

<210> SEQ ID NO 44
<211> LENGTH: 109
<212> TYPE: PRT
<213> ORGANISM: Homo sapiens

<400> SEQUENCE: 44

Glu Pro Val Leu Thr Gln Ser Pro Gly Thr Leu Ser Val Ser Pro Gly
1               5                   10                  15

Glu Gly Ala Thr Leu Ser Cys Arg Ala Arg Gln Gly Phe Ser Ala Asp
                20                  25                  30

His Val Ala Trp Phe Gln Lys Lys Pro Gly Arg Pro Pro Arg Leu Leu
        35                  40                  45

Ile Phe Glu Ala Ser Arg Arg Ala Ser Gly Thr Pro Glu Arg Phe Ser
        50                  55                  60

Gly Ser Gly Ser Gly Pro Glu Tyr Thr Leu Thr Ile Thr Arg Val Glu
```

-continued

```
65              70              75              80

Pro Glu Asp Phe Ala Val Tyr Tyr Cys Gln Ser Tyr Gly Ser Ile Thr
                85              90              95

Pro Leu Val Phe Gly Gly Gly Thr Arg Val Asp Val Lys
            100             105

<210> SEQ ID NO 45
<211> LENGTH: 125
<212> TYPE: PRT
<213> ORGANISM: Homo sapiens

<400> SEQUENCE: 45

Gln Leu Val Gln Ser Gly Gly Gly Val Arg Arg Pro Gly Ala Ser Val
1               5               10              15

Lys Ile Ser Cys Glu Thr Pro Glu Tyr Thr Phe Thr Lys Tyr Trp Leu
            20              25              30

His Trp Leu Arg Gln Ala Pro Gly Arg Gly Leu Glu Trp Met Gly Val
        35              40              45

Val Ser Pro His Gly Gly Arg Pro Met Phe Ala Phe Glu Phe Arg Asp
    50              55              60

Arg Leu Thr Leu Thr Arg Asp Ile His Thr Thr Thr His Tyr Met Glu
65              70              75              80

Leu Gly Gly Leu Thr Ser Asp Asp Thr Ala Val Tyr Tyr Cys Ala Arg
                85              90              95

Asp Pro Phe Gly Glu Thr Phe Arg Gly His Asp Gln Pro Tyr Gln Met
            100             105             110

Asp Val Trp Gly Gly Gly Thr Thr Ile Val Val Ser Ser
        115             120             125

<210> SEQ ID NO 46
<211> LENGTH: 109
<212> TYPE: PRT
<213> ORGANISM: Homo sapiens

<400> SEQUENCE: 46

Glu Pro Val Leu Thr Gln Ser Pro Gly Thr Leu Ser Leu Ser Pro Gly
1               5               10              15

Glu Arg Ala Thr Leu Ser Cys Arg Ala Arg Gln Gly Phe Ser Ala Asp
            20              25              30

His Val Ala Trp Phe Gln Lys Lys Pro Gly Arg Pro Pro Arg Leu Leu
        35              40              45

Ile Phe Glu Ala Ser Arg Arg Ala Ser Gly Thr Pro Glu Arg Phe Ser
    50              55              60

Gly Ser Gly Ser Gly Pro Glu Tyr Thr Leu Thr Ile Thr Arg Val Glu
65              70              75              80

Pro Glu Asp Phe Ala Val Tyr Tyr Cys Gln Ser Tyr Gly Ser Ile Thr
                85              90              95

Pro Leu Val Phe Gly Gly Gly Thr Arg Val Asp Val Lys
            100             105

<210> SEQ ID NO 47
<211> LENGTH: 131
<212> TYPE: PRT
<213> ORGANISM: Homo sapiens
<220> FEATURE:
<221> NAME/KEY: SITE
<222> LOCATION: (2)..(4)
<223> OTHER INFORMATION: Xaa can indicate any amino acid or no amino
      acid
```

```
<220> FEATURE:
<221> NAME/KEY: SITE
<222> LOCATION: (9)..(9)
<223> OTHER INFORMATION: Xaa can indicate any amino acid or no amino
      acid
<220> FEATURE:
<221> NAME/KEY: SITE
<222> LOCATION: (11)..(11)
<223> OTHER INFORMATION: Xaa can indicate any amino acid or no amino
      acid
<220> FEATURE:
<221> NAME/KEY: SITE
<222> LOCATION: (19)..(19)
<223> OTHER INFORMATION: Xaa can indicate any amino acid or no amino
      acid
<220> FEATURE:
<221> NAME/KEY: SITE
<222> LOCATION: (39)..(39)
<223> OTHER INFORMATION: Xaa can indicate any amino acid or no amino
      acid
<220> FEATURE:
<221> NAME/KEY: SITE
<222> LOCATION: (50)..(50)
<223> OTHER INFORMATION: Xaa can indicate any amino acid or no amino
      acid
<220> FEATURE:
<221> NAME/KEY: SITE
<222> LOCATION: (61)..(61)
<223> OTHER INFORMATION: Xaa can indicate any amino acid or no amino
      acid
<220> FEATURE:
<221> NAME/KEY: SITE
<222> LOCATION: (71)..(71)
<223> OTHER INFORMATION: Xaa can indicate any amino acid or no amino
      acid
<220> FEATURE:
<221> NAME/KEY: SITE
<222> LOCATION: (84)..(84)
<223> OTHER INFORMATION: Xaa can indicate any amino acid or no amino
      acid
<220> FEATURE:
<221> NAME/KEY: SITE
<222> LOCATION: (87)..(87)
<223> OTHER INFORMATION: Xaa can indicate any amino acid or no amino
      acid
<220> FEATURE:
<221> NAME/KEY: SITE
<222> LOCATION: (90)..(91)
<223> OTHER INFORMATION: Xaa can indicate any amino acid or no amino
      acid
<220> FEATURE:
<221> NAME/KEY: SITE
<222> LOCATION: (93)..(94)
<223> OTHER INFORMATION: Xaa can indicate any amino acid or no amino
      acid
<220> FEATURE:
<221> NAME/KEY: SITE
<222> LOCATION: (97)..(97)
<223> OTHER INFORMATION: Xaa can indicate any amino acid or no amino
      acid
<220> FEATURE:
<221> NAME/KEY: SITE
<222> LOCATION: (101)..(101)
<223> OTHER INFORMATION: Xaa can indicate any amino acid or no amino
      acid
<220> FEATURE:
<221> NAME/KEY: SITE
<222> LOCATION: (109)..(111)
<223> OTHER INFORMATION: Xaa can indicate any amino acid or no amino
      acid
<220> FEATURE:
<221> NAME/KEY: SITE
<222> LOCATION: (116)..(116)
<223> OTHER INFORMATION: Xaa can indicate any amino acid or no amino
      acid
<220> FEATURE:
<221> NAME/KEY: SITE
<222> LOCATION: (123)..(123)
<223> OTHER INFORMATION: Xaa can indicate any amino acid or no amino
``` acid
<220> FEATURE:
<221> NAME/KEY: SITE
<222> LOCATION: (126)..(127)
<223> OTHER INFORMATION: Xaa can indicate any amino acid or no amino
      acid
<220> FEATURE:
<221> NAME/KEY: SITE
<222> LOCATION: (131)..(131)
<223> OTHER INFORMATION: Xaa can indicate any amino acid or no amino
      acid

<400> SEQUENCE: 47

Gln Xaa Xaa Xaa Phe Gln Ser Gly Xaa Glu Xaa Lys Arg Pro Gly Ala
1               5                   10                  15

Ser Val Xaa Ile Ser Cys Arg Ala Asp Asp Asp Pro Tyr Thr Asp Asp
            20                  25                  30

Asp Thr Phe Thr Lys Tyr Xaa Thr His Trp Ile Arg Gln Ala Pro Gly
        35                  40                  45

Gln Xaa Pro Glu Trp Leu Gly Val Ile Ser Pro His Xaa Ala Arg Pro
    50                  55                  60

Ile Tyr Ser Tyr Lys Phe Xaa Asp Arg Leu Thr Leu Thr Arg Asp Ser
65                  70                  75                  80

Ser Leu Thr Xaa Val Tyr Xaa Glu Leu Xaa Xaa Leu Xaa Xaa Asp Asp
            85                  90                  95

Xaa Gly Ile Tyr Xaa Cys Ala Arg Asp Pro Phe Gly Xaa Xaa Xaa Pro
            100                 105                 110

His Tyr Asn Xaa His Met Asp Val Trp Gly Xaa Gly Thr Xaa Xaa Ile
        115                 120                 125

Val Ser Xaa
    130

<210> SEQ ID NO 48
<211> LENGTH: 108
<212> TYPE: PRT
<213> ORGANISM: Homo sapiens
<220> FEATURE:
<221> NAME/KEY: SITE
<222> LOCATION: (2)..(2)
<223> OTHER INFORMATION: Xaa can indicate any amino acid or no amino
      acid
<220> FEATURE:
<221> NAME/KEY: SITE
<222> LOCATION: (13)..(13)
<223> OTHER INFORMATION: Xaa can indicate any amino acid or no amino
      acid
<220> FEATURE:
<221> NAME/KEY: SITE
<222> LOCATION: (20)..(21)
<223> OTHER INFORMATION: Xaa can indicate any amino acid or no amino
      acid
<220> FEATURE:
<221> NAME/KEY: SITE
<222> LOCATION: (24)..(24)
<223> OTHER INFORMATION: Xaa can indicate any amino acid or no amino
      acid
<220> FEATURE:
<221> NAME/KEY: SITE
<222> LOCATION: (30)..(33)
<223> OTHER INFORMATION: Xaa can indicate any amino acid or no amino
      acid
<220> FEATURE:
<221> NAME/KEY: SITE
<222> LOCATION: (41)..(41)
<223> OTHER INFORMATION: Xaa can indicate any amino acid or no amino
      acid
<220> FEATURE:
<221> NAME/KEY: SITE
<222> LOCATION: (46)..(46)

-continued

<223> OTHER INFORMATION: Xaa can indicate any amino acid or no amino
      acid
<220> FEATURE:
<221> NAME/KEY: SITE
<222> LOCATION: (49)..(49)
<223> OTHER INFORMATION: Xaa can be Leu or Ile
<220> FEATURE:
<221> NAME/KEY: SITE
<222> LOCATION: (51)..(52)
<223> OTHER INFORMATION: Xaa can indicate any amino acid or no amino
      acid
<220> FEATURE:
<221> NAME/KEY: SITE
<222> LOCATION: (54)..(54)
<223> OTHER INFORMATION: Xaa can indicate any amino acid or no amino
      acid
<220> FEATURE:
<221> NAME/KEY: SITE
<222> LOCATION: (64)..(64)
<223> OTHER INFORMATION: Xaa can indicate any amino acid or no amino
      acid
<220> FEATURE:
<221> NAME/KEY: SITE
<222> LOCATION: (66)..(66)
<223> OTHER INFORMATION: Xaa can indicate any amino acid or no amino
      acid
<220> FEATURE:
<221> NAME/KEY: SITE
<222> LOCATION: (69)..(70)
<223> OTHER INFORMATION: Xaa can indicate any amino acid or no amino
      acid
<220> FEATURE:
<221> NAME/KEY: SITE
<222> LOCATION: (77)..(78)
<223> OTHER INFORMATION: Xaa can indicate any amino acid or no amino
      acid
<220> FEATURE:
<221> NAME/KEY: SITE
<222> LOCATION: (81)..(81)
<223> OTHER INFORMATION: Xaa can indicate any amino acid or no amino
      acid
<220> FEATURE:
<221> NAME/KEY: SITE
<222> LOCATION: (92)..(92)
<223> OTHER INFORMATION: Xaa can indicate any amino acid or no amino
      acid
<220> FEATURE:
<221> NAME/KEY: SITE
<222> LOCATION: (94)..(94)
<223> OTHER INFORMATION: Xaa can indicate any amino acid or no amino
      acid
<220> FEATURE:
<221> NAME/KEY: SITE
<222> LOCATION: (104)..(104)
<223> OTHER INFORMATION: Xaa can indicate any amino acid or no amino
      acid
<220> FEATURE:
<221> NAME/KEY: SITE
<222> LOCATION: (107)..(108)
<223> OTHER INFORMATION: Xaa can indicate any amino acid or no amino
      acid

<400> SEQUENCE: 48

Glu Xaa Val Leu Thr Gln Ser Pro Ala Ile Leu Ser Xaa Ser Pro Gly
1               5                   10                  15

Asp Arg Val Xaa Xaa Ser Cys Xaa Ala Ser Glx Gly Leu Xaa Xaa Xaa
            20                  25                  30

Xaa Leu Ala Trp Tyr Arg Phe Lys Xaa Gly Gln Ile Pro Xaa Leu Val
        35                  40                  45

Xaa Phe Xaa Xaa Ser Xaa Arg Ala Arg Gly Thr Pro Asp Arg Phe Xaa
    50                  55                  60

Gly Xaa Gly Ser Xaa Xaa Asp Phe Thr Leu Thr Ile Xaa Xaa Val Glx
65                  70                  75                  80

-continued

```
Xaa Glu Asp Phe Ala Thr Tyr Tyr Cys Gln Arg Xaa Gly Xaa Thr Pro
            85                  90                  95

Ile Thr Phe Gly Gly Gly Thr Xaa Leu Asp Xaa Xaa
            100                 105

<210> SEQ ID NO 49
<211> LENGTH: 126
<212> TYPE: PRT
<213> ORGANISM: Homo sapiens
<220> FEATURE:
<221> NAME/KEY: SITE
<222> LOCATION: (3)..(3)
<223> OTHER INFORMATION: Xaa can indicate any amino acid or no amino
      acid
<220> FEATURE:
<221> NAME/KEY: SITE
<222> LOCATION: (5)..(5)
<223> OTHER INFORMATION: Xaa can indicate any amino acid or no amino
      acid
<220> FEATURE:
<221> NAME/KEY: SITE
<222> LOCATION: (10)..(11)
<223> OTHER INFORMATION: Xaa can indicate any amino acid or no amino
      acid
<220> FEATURE:
<221> NAME/KEY: SITE
<222> LOCATION: (17)..(18)
<223> OTHER INFORMATION: Xaa can indicate any amino acid or no amino
      acid
<220> FEATURE:
<221> NAME/KEY: SITE
<222> LOCATION: (21)..(22)
<223> OTHER INFORMATION: Xaa can indicate any amino acid or no amino
      acid
<220> FEATURE:
<221> NAME/KEY: SITE
<222> LOCATION: (25)..(25)
<223> OTHER INFORMATION: Xaa can indicate any amino acid or no amino
      acid
<220> FEATURE:
<221> NAME/KEY: SITE
<222> LOCATION: (31)..(31)
<223> OTHER INFORMATION: Xaa can indicate any amino acid or no amino
      acid
<220> FEATURE:
<221> NAME/KEY: SITE
<222> LOCATION: (32)..(32)
<223> OTHER INFORMATION: Xaa can be Leu or Ile
<220> FEATURE:
<221> NAME/KEY: SITE
<222> LOCATION: (35)..(35)
<223> OTHER INFORMATION: Xaa can indicate any amino acid or no amino
      acid
<220> FEATURE:
<221> NAME/KEY: SITE
<222> LOCATION: (41)..(41)
<223> OTHER INFORMATION: Xaa can indicate any amino acid or no amino
      acid
<220> FEATURE:
<221> NAME/KEY: SITE
<222> LOCATION: (43)..(43)
<223> OTHER INFORMATION: Xaa can indicate any amino acid or no amino
      acid
<220> FEATURE:
<221> NAME/KEY: SITE
<222> LOCATION: (46)..(46)
<223> OTHER INFORMATION: Xaa can indicate any amino acid or no amino
      acid
<220> FEATURE:
<221> NAME/KEY: SITE
<222> LOCATION: (48)..(48)
<223> OTHER INFORMATION: Xaa can indicate any amino acid or no amino
      acid
<220> FEATURE:
<221> NAME/KEY: SITE
<222> LOCATION: (57)..(61)
<223> OTHER INFORMATION: Xaa can indicate any amino acid or no amino
```

-continued

```
      acid
<220> FEATURE:
<221> NAME/KEY: SITE
<222> LOCATION: (68)..(68)
<223> OTHER INFORMATION: Xaa can indicate any amino acid or no amino
      acid
<220> FEATURE:
<221> NAME/KEY: SITE
<222> LOCATION: (71)..(71)
<223> OTHER INFORMATION: Xaa can indicate any amino acid or no amino
      acid
<220> FEATURE:
<221> NAME/KEY: SITE
<222> LOCATION: (74)..(74)
<223> OTHER INFORMATION: Xaa can indicate any amino acid or no amino
      acid
<220> FEATURE:
<221> NAME/KEY: SITE
<222> LOCATION: (78)..(78)
<223> OTHER INFORMATION: Xaa can indicate any amino acid or no amino
      acid
<220> FEATURE:
<221> NAME/KEY: SITE
<222> LOCATION: (80)..(80)
<223> OTHER INFORMATION: Xaa can indicate any amino acid or no amino
      acid
<220> FEATURE:
<221> NAME/KEY: SITE
<222> LOCATION: (82)..(82)
<223> OTHER INFORMATION: Xaa can indicate any amino acid or no amino
      acid
<220> FEATURE:
<221> NAME/KEY: SITE
<222> LOCATION: (85)..(87)
<223> OTHER INFORMATION: Xaa can indicate any amino acid or no amino
      acid
<220> FEATURE:
<221> NAME/KEY: SITE
<222> LOCATION: (89)..(91)
<223> OTHER INFORMATION: Xaa can indicate any amino acid or no amino
      acid
<220> FEATURE:
<221> NAME/KEY: SITE
<222> LOCATION: (93)..(93)
<223> OTHER INFORMATION: Xaa can indicate any amino acid or no amino
      acid
<220> FEATURE:
<221> NAME/KEY: SITE
<222> LOCATION: (98)..(99)
<223> OTHER INFORMATION: Xaa can indicate any amino acid or no amino
      acid
<220> FEATURE:
<221> NAME/KEY: SITE
<222> LOCATION: (102)..(112)
<223> OTHER INFORMATION: Xaa can indicate any amino acid or no amino
      acid
<220> FEATURE:
<221> NAME/KEY: SITE
<222> LOCATION: (115)..(115)
<223> OTHER INFORMATION: Xaa can indicate any amino acid or no amino
      acid
<220> FEATURE:
<221> NAME/KEY: SITE
<222> LOCATION: (120)..(123)
<223> OTHER INFORMATION: Xaa can indicate any amino acid or no amino
      acid
<220> FEATURE:
<221> NAME/KEY: SITE
<222> LOCATION: (125)..(125)
<223> OTHER INFORMATION: Xaa can indicate any amino acid or no amino
      acid
<220> FEATURE:
<221> NAME/KEY: SITE
<222> LOCATION: (125)..(125)
<223> OTHER INFORMATION: Xaa can indicate any amino acid or no amino
      acid

<400> SEQUENCE: 49
```

-continued

```
Gln Leu Xaa Gln Xaa Gly Gly Gly Val Xaa Xaa Pro Gly Ala Ser Val
1               5                   10                  15

Xaa Xaa Ser Cys Xaa Xaa Pro Glu Xaa Thr Phe Thr Lys Tyr Xaa Xaa
            20                  25                  30

His Trp Xaa Arg Gln Ala Pro Gly Xaa Gly Xaa Glu Trp Xaa Gly Xaa
        35                  40                  45

Val Ser Pro His Gly Gly Arg Pro Xaa Xaa Xaa Xaa Xaa Phe Arg Asp
    50                  55                  60

Arg Leu Thr Xaa Thr Arg Xaa Ile His Xaa Thr His Xaa Met Xaa
65                  70                  75                  80

Leu Xaa Gly Leu Xaa Xaa Xaa Asp Xaa Xaa Xaa Tyr Xaa Cys Ala Arg
            85                  90                  95

Asp Xaa Xaa Gly Glu Xaa Xaa Xaa Xaa Xaa Xaa Xaa Xaa Xaa Xaa Xaa
            100                 105                 110

Met Asp Xaa Trp Gly Gly Gly Xaa Xaa Xaa Xaa Val Xaa Ser
        115                 120                 125
```

```
<210> SEQ ID NO 50
<211> LENGTH: 111
<212> TYPE: PRT
<213> ORGANISM: Homo sapiens
<220> FEATURE:
<221> NAME/KEY: SITE
<222> LOCATION: (1)..(3)
<223> OTHER INFORMATION: Xaa can indicate any amino acid or no amino
      acid
<220> FEATURE:
<221> NAME/KEY: SITE
<222> LOCATION: (9)..(9)
<223> OTHER INFORMATION: Xaa can indicate any amino acid or no amino
      acid
<220> FEATURE:
<221> NAME/KEY: SITE
<222> LOCATION: (13)..(13)
<223> OTHER INFORMATION: Xaa can indicate any amino acid or no amino
      acid
<220> FEATURE:
<221> NAME/KEY: SITE
<222> LOCATION: (18)..(20)
<223> OTHER INFORMATION: Xaa can indicate any amino acid or no amino
      acid
<220> FEATURE:
<221> NAME/KEY: SITE
<222> LOCATION: (26)..(27)
<223> OTHER INFORMATION: Xaa can indicate any amino acid or no amino
      acid
<220> FEATURE:
<221> NAME/KEY: SITE
<222> LOCATION: (29)..(32)
<223> OTHER INFORMATION: Xaa can indicate any amino acid or no amino
      acid
<220> FEATURE:
<221> NAME/KEY: SITE
<222> LOCATION: (34)..(35)
<223> OTHER INFORMATION: Xaa can indicate any amino acid or no amino
      acid
<220> FEATURE:
<221> NAME/KEY: SITE
<222> LOCATION: (39)..(41)
<223> OTHER INFORMATION: Xaa can indicate any amino acid or no amino
      acid
<220> FEATURE:
<221> NAME/KEY: SITE
<222> LOCATION: (43)..(44)
<223> OTHER INFORMATION: Xaa can indicate any amino acid or no amino
      acid
<220> FEATURE:
<221> NAME/KEY: SITE
<222> LOCATION: (51)..(53)
<223> OTHER INFORMATION: Xaa can indicate any amino acid or no amino
      acid
```

```
<220> FEATURE:
<221> NAME/KEY: SITE
<222> LOCATION: (57)..(57)
<223> OTHER INFORMATION: Xaa can indicate any amino acid or no amino
      acid
<220> FEATURE:
<221> NAME/KEY: SITE
<222> LOCATION: (59)..(59)
<223> OTHER INFORMATION: Xaa can indicate any amino acid or no amino
      acid
<220> FEATURE:
<221> NAME/KEY: SITE
<222> LOCATION: (60)..(61)
<223> OTHER INFORMATION: Xaa can indicate any amino acid or no amino
      acid
<220> FEATURE:
<221> NAME/KEY: SITE
<222> LOCATION: (64)..(69)
<223> OTHER INFORMATION: Xaa can indicate any amino acid or no amino
      acid
<220> FEATURE:
<221> NAME/KEY: SITE
<222> LOCATION: (71)..(75)
<223> OTHER INFORMATION: Xaa can indicate any amino acid or no amino
      acid
<220> FEATURE:
<221> NAME/KEY: SITE
<222> LOCATION: (79)..(80)
<223> OTHER INFORMATION: Xaa can indicate any amino acid or no amino
      acid
<220> FEATURE:
<221> NAME/KEY: SITE
<222> LOCATION: (83)..(84)
<223> OTHER INFORMATION: Xaa can indicate any amino acid or no amino
      acid
<220> FEATURE:
<221> NAME/KEY: SITE
<222> LOCATION: (88)..(88)
<223> OTHER INFORMATION: Xaa can indicate any amino acid or no amino
      acid
<220> FEATURE:
<221> NAME/KEY: SITE
<222> LOCATION: (90)..(90)
<223> OTHER INFORMATION: Xaa can indicate any amino acid or no amino
      acid
<220> FEATURE:
<221> NAME/KEY: SITE
<222> LOCATION: (93)..(93)
<223> OTHER INFORMATION: Xaa can indicate any amino acid or no amino
      acid
<220> FEATURE:
<221> NAME/KEY: SITE
<222> LOCATION: (96)..(96)
<223> OTHER INFORMATION: Xaa can indicate any amino acid or no amino
      acid
<220> FEATURE:
<221> NAME/KEY: SITE
<222> LOCATION: (100)..(100)
<223> OTHER INFORMATION: Xaa can be Leu or Ile
<220> FEATURE:
<221> NAME/KEY: SITE
<222> LOCATION: (101)..(101)
<223> OTHER INFORMATION: Xaa can indicate any amino acid or no amino
      acid
<220> FEATURE:
<221> NAME/KEY: SITE
<222> LOCATION: (107)..(108)
<223> OTHER INFORMATION: Xaa can indicate any amino acid or no amino
      acid
<220> FEATURE:
<221> NAME/KEY: SITE
<222> LOCATION: (110)..(110)
<223> OTHER INFORMATION: Xaa can indicate any amino acid or no amino
      acid

<400> SEQUENCE: 50

Xaa Xaa Xaa Leu Thr Gln Ser Pro Xaa Thr Leu Ser Xaa Ser Pro Gly
1               5                   10                  15
```

-continued

```
Glu Xaa Xaa Xaa Leu Ser Cys Arg Ala Xaa Xaa Gly Xaa Xaa Xaa Xaa
        20                  25                  30

His Xaa Xaa Trp Phe Gln Xaa Xaa Xaa Gly Xaa Xaa Pro Arg Leu Leu
        35                  40                  45

Ile Phe Xaa Xaa Xaa Arg Arg Ala Xaa Gly Xaa Xaa Xaa Arg Phe Xaa
        50                  55                  60

Xaa Xaa Xaa Xaa Xaa Ser Xaa Xaa Xaa Xaa Xaa Leu Thr Ile Xaa Xaa
65                  70                  75                  80

Val Glu Xaa Xaa Asp Phe Ala Xaa Tyr Xaa Cys Gln Xaa Tyr Gly Xaa
                85                  90                  95

Ile Thr Pro Xaa Xaa Phe Gly Gly Gly Thr Xaa Xaa Asp Xaa Lys
            100                 105                 110
```

```
<210> SEQ ID NO 51
<211> LENGTH: 11
<212> TYPE: PRT
<213> ORGANISM: Human immunodeficiency virus type 1

<400> SEQUENCE: 51

Ser Glu Asn Phe Thr Asn Asn Ala Lys Thr Ile
1               5                   10
```

```
<210> SEQ ID NO 52
<211> LENGTH: 14
<212> TYPE: PRT
<213> ORGANISM: Human immunodeficiency virus type 1

<400> SEQUENCE: 52

Gly Gly Lys Asp Thr Asn Gly Thr Glu Ile Phe Arg Pro Gly
1               5                   10
```

```
<210> SEQ ID NO 53
<211> LENGTH: 6
<212> TYPE: PRT
<213> ORGANISM: Human immunodeficiency virus type 1

<400> SEQUENCE: 53

Phe Asn Ile Thr Thr Ser
1               5
```

```
<210> SEQ ID NO 54
<211> LENGTH: 19
<212> TYPE: PRT
<213> ORGANISM: Human immunodeficiency virus type 1

<400> SEQUENCE: 54

Asn Asn Thr Arg Lys Ser Ile Asn Ile Gly Pro Gly Arg Ala Leu Tyr
1               5                   10                  15

Thr Thr Gly
```

```
<210> SEQ ID NO 55
<211> LENGTH: 13
<212> TYPE: PRT
<213> ORGANISM: Human immunodeficiency virus type 1

<400> SEQUENCE: 55

Pro Ser Ser Gly Gly Asp Pro Glu Ile Val Thr His Ser
1               5                   10
```

```
<210> SEQ ID NO 56
<211> LENGTH: 9
```

<212> TYPE: PRT
<213> ORGANISM: Human immunodeficiency virus type 1

<400> SEQUENCE: 56

Asn Met Trp Gln Glu Val Gly Lys Ala
1               5

<210> SEQ ID NO 57
<211> LENGTH: 11
<212> TYPE: PRT
<213> ORGANISM: Human immunodeficiency virus type 1

<400> SEQUENCE: 57

Ser Glu Asn Phe Ile Lys Asn Ala Lys Thr Ile
1               5                   10

<210> SEQ ID NO 58
<211> LENGTH: 11
<212> TYPE: PRT
<213> ORGANISM: Human immunodeficiency virus type 1

<400> SEQUENCE: 58

Ser Glu Asn Phe Thr Asn Asn Thr Lys Thr Ile
1               5                   10

<210> SEQ ID NO 59
<211> LENGTH: 11
<212> TYPE: PRT
<213> ORGANISM: Human immunodeficiency virus type 1

<400> SEQUENCE: 59

Ser Glu Asn Phe Thr Asn Asn Asp Lys Thr Ile
1               5                   10

<210> SEQ ID NO 60
<211> LENGTH: 12
<212> TYPE: PRT
<213> ORGANISM: Human immunodeficiency virus type 1

<400> SEQUENCE: 60

Gly Asp Lys Asp Gly Thr Glu Ile Phe Arg Pro Glu
1               5                   10

<210> SEQ ID NO 61
<211> LENGTH: 14
<212> TYPE: PRT
<213> ORGANISM: Human immunodeficiency virus type 1

<400> SEQUENCE: 61

Gly Asp Lys Asp Thr Asn Gly Thr Glu Ile Phe Arg Pro Glu
1               5                   10

<210> SEQ ID NO 62
<211> LENGTH: 11
<212> TYPE: PRT
<213> ORGANISM: Human immunodeficiency virus type 1

<400> SEQUENCE: 62

Ser Glu Asn Phe Thr Asn Asn Ala Glu Thr Ile
1               5                   10

<210> SEQ ID NO 63
<211> LENGTH: 14
<212> TYPE: PRT
<213> ORGANISM: Human immunodeficiency virus type 1

<400> SEQUENCE: 63

Gly Asp Lys Asp Thr Asn Glu Thr Glu Ile Phe Arg Pro Gly
1               5                   10

<210> SEQ ID NO 64
<211> LENGTH: 14
<212> TYPE: PRT
<213> ORGANISM: Human immunodeficiency virus type 1

<400> SEQUENCE: 64

Gly Asp Lys Asp Thr Asn Gly Thr Glu Ile Phe Arg Pro Gly
1               5                   10

<210> SEQ ID NO 65
<211> LENGTH: 14
<212> TYPE: PRT
<213> ORGANISM: Human immunodeficiency virus type 1

<400> SEQUENCE: 65

Gly Glu Lys Asp Thr Asn Gly Thr Glu Ile Phe Arg Pro Gly
1               5                   10

<210> SEQ ID NO 66
<211> LENGTH: 11
<212> TYPE: PRT
<213> ORGANISM: Human immunodeficiency virus type 1

<400> SEQUENCE: 66

Ser Glu Asn Phe Thr Asn Asn Ala Arg Thr Ile
1               5                   10

<210> SEQ ID NO 67
<211> LENGTH: 11
<212> TYPE: PRT
<213> ORGANISM: Human immunodeficiency virus type 1

<400> SEQUENCE: 67

Ser Glu Asn Phe Thr Asn Asp Ala Lys Thr Ile
1               5                   10

<210> SEQ ID NO 68
<211> LENGTH: 14
<212> TYPE: PRT
<213> ORGANISM: Human immunodeficiency virus type 1

<400> SEQUENCE: 68

Gly Val Lys Asp Thr Asn Gly Thr Glu Ile Phe Arg Pro Gly
1               5                   10

<210> SEQ ID NO 69
<211> LENGTH: 14
<212> TYPE: PRT
<213> ORGANISM: Human immunodeficiency virus type 1

<400> SEQUENCE: 69

Gly Val Glu Asp Thr Asn Gly Thr Glu Ile Phe Arg Pro Gly
1               5                   10

<210> SEQ ID NO 70
<211> LENGTH: 11
<212> TYPE: PRT
<213> ORGANISM: Human immunodeficiency virus type 1

<400> SEQUENCE: 70

-continued

```
Ser Glu Asn Phe Thr Ser Asn Ala Lys Thr Ile
1               5                   10

<210> SEQ ID NO 71
<211> LENGTH: 14
<212> TYPE: PRT
<213> ORGANISM: Human immunodeficiency virus type 1

<400> SEQUENCE: 71

Gly Asp Lys Asp Thr Asn Gly Asn Glu Ile Phe Arg Pro Gly
1               5                   10

<210> SEQ ID NO 72
<211> LENGTH: 14
<212> TYPE: PRT
<213> ORGANISM: Human immunodeficiency virus type 1

<400> SEQUENCE: 72

Gly Asp Lys Asp Thr Asn Gly Asn Glu Ile Phe Arg Pro Glu
1               5                   10

<210> SEQ ID NO 73
<211> LENGTH: 11
<212> TYPE: PRT
<213> ORGANISM: Human immunodeficiency virus type 1

<400> SEQUENCE: 73

Ser Glu Asn Phe Thr Tyr Asn Ala Lys Thr Ile
1               5                   10

<210> SEQ ID NO 74
<211> LENGTH: 11
<212> TYPE: PRT
<213> ORGANISM: Human immunodeficiency virus type 1

<400> SEQUENCE: 74

Ser Glu Asn Phe Ala Asn Asn Thr Lys Thr Ile
1               5                   10

<210> SEQ ID NO 75
<211> LENGTH: 11
<212> TYPE: PRT
<213> ORGANISM: Human immunodeficiency virus type 1

<400> SEQUENCE: 75

Ser Glu Asn Phe Thr Lys Asn Ala Lys Thr Ile
1               5                   10

<210> SEQ ID NO 76
<211> LENGTH: 11
<212> TYPE: PRT
<213> ORGANISM: Human immunodeficiency virus type 1

<400> SEQUENCE: 76

Phe Glu Asn Phe Thr Asn Asn Ala Lys Thr Ile
1               5                   10

<210> SEQ ID NO 77
<211> LENGTH: 14
<212> TYPE: PRT
<213> ORGANISM: Human immunodeficiency virus type 1

<400> SEQUENCE: 77

Gly Asp Glu Asp Thr Asn Gly Thr Glu Ile Phe Arg Pro Gly
```

-continued

```
1               5                   10

<210> SEQ ID NO 78
<211> LENGTH: 11
<212> TYPE: PRT
<213> ORGANISM: Human immunodeficiency virus type 1

<400> SEQUENCE: 78

Tyr Glu Asn Phe Thr Asn Asn Ala Lys Thr Ile
1               5                   10

<210> SEQ ID NO 79
<211> LENGTH: 9
<212> TYPE: PRT
<213> ORGANISM: Human immunodeficiency virus type 1

<400> SEQUENCE: 79

Asn Ile Trp Gln Glu Val Gly Lys Ala
1               5

<210> SEQ ID NO 80
<211> LENGTH: 14
<212> TYPE: PRT
<213> ORGANISM: Human immunodeficiency virus type 1

<400> SEQUENCE: 80

Gly Gly Lys Asp Thr Asn Gly Thr Glu Ile Phe Arg Pro Arg
1               5                   10
```